US012760114B2

(12) United States Patent
Kawashima et al.

(10) Patent No.: US 12,760,114 B2
(45) Date of Patent: Oct. 13, 2026

(54) ANTI-GLYCAN ANTIBODY AND USE THEREOF

(71) Applicant: NATIONAL UNIVERSITY CORPORATION CHIBA UNIVERSITY, Chiba (JP)

(72) Inventors: Hiroto Kawashima, Chiba (JP); Ryuji Matsumura, Aichi (JP)

(73) Assignee: NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 702 days.

(21) Appl. No.: 18/030,368

(22) PCT Filed: Oct. 6, 2021

(86) PCT No.: PCT/JP2021/036893
§ 371 (c)(1),
(2) Date: Apr. 5, 2023

(87) PCT Pub. No.: WO2022/075337
PCT Pub. Date: Apr. 14, 2022

(65) Prior Publication Data
US 2023/0365706 A1 Nov. 16, 2023

(30) Foreign Application Priority Data
Oct. 7, 2020 (JP) ................................. 2020-169966

(51) Int. Cl.
*C07K 16/28* (2006.01)
*A61P 37/06* (2006.01)
*C12N 15/79* (2006.01)
*A61K 39/00* (2006.01)

(52) U.S. Cl.
CPC .......... *C07K 16/2896* (2013.01); *A61P 37/06* (2018.01); *C12N 15/79* (2013.01); *A61K 2039/505* (2013.01); *C07K 2317/24* (2013.01); *C07K 2317/55* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

2016/0244521 A1* 8/2016 White ................ C07K 16/2803

FOREIGN PATENT DOCUMENTS

EP 1726654 A2 * 11/2006 ............... C12N 9/13

OTHER PUBLICATIONS

Mitsuoka et al., J Biol Chem. May 1, 1998;273(18):11225-33. doi: 10.1074/jbc.273.18.11225. PMID: 9556613.*

Janeway et al., Immunobiology, 3rd edition, Garland Publishing Inc., 1997, pp. 3:1-3:11.*

Rudikoff et al., Proc Natl Acad Sci U S A. Mar. 1982;79(6):1979-83. doi: 10.1073/pnas.79.6.1979. PMID: 6804947.*

Edwards et al., J Mol Biol. Nov. 14, 2003;334(1):103-18. doi: 10.1016/j.jmb.2003.09.054. PMID: 14596803.*

Llyod et al., Protein Eng Des Sel. Mar. 2009;22(3):159-68. doi: 10.1093/protein/gzn058. Epub Oct. 29, 2008. PMID: 18974080.*

Goel et al., J Immunol. Dec. 15, 2004; 173(12):7358-67 PMID: 15585860 DOI: 10.4049/jimmunol. 173. 12.7358.*

Lescar et al., J Biol Chem. Jul. 28, 1995;270(30):18067-76. doi: 10.1074/jbc.270.30.18067. PMID: 7629116.*

Kanyavuz et al., Nat Rev Immunol. Jun. 2019;19(6):355-368. doi: 10.1038/S41577-019-0126-7. PMID: 30718829.*

Winkler et al., J Immunol. Oct. 15, 2000;165(8):4505-14. doi: 10.4049/jimmunol.165.8.4505. PMID: 11035090.*

Kipriyanov et al., Mol Biotechnol. Jan. 2004;26(1):39-60. doi: 10.1385/MB:26:1:39. PMID: 14734823.*

Hirakawa et al., "Analysis of lymphocyte disposition using novel anti-glycan monoclonal antibody," Journal of Japanese Biochemical Society, vol. 90, No. 2, 2018, pp. 221-224.

Kawashima et al., "N-acetylglucosamine-6-O-sulfotransferases 1 and 2 cooperatively control lymphocyte homing through L-selectin ligand biosynthesis in high endothelial venules," Nature Immunology, vol. 6, No. 11, Nov. 2005, pp. 1096-1104.

Streeter et al., "Immunohistologic and Functional Characterization of a Vascular Addressin Involved in Lymphocyte Homing into Peripheral Lymph Nodes," The Journal of Cell Biology, vol. 107, Nov. 1988, pp. 1853-1862.

Hirakawa et al., "Novel Anti-carbohydrate Antibodies Reveal the Cooperative Function of Sulfated NV- and O-Glycans in Lymphocyte Homing," The Journal of Biological Chemistry, vol. 285, No. 52, Dec. 24, 2010, pp. 40864-40878.

Matsumura et al., "Novel Antibodies Reactive with Sialyl Lewis X in Both Humans and Mice Define Its Critical Role in Leukocyte Trafficking and Contact Hypersensitivity Responses," The Journal of Biological Chemistry, vol. 290, No. 24, Jun. 12, 2015, pp. 15313-15326.

Mitsuoka et al., "Identification of a Major Carbohydrate Capping Group of the L-selectin Ligand on High Endothelial Venules in Human Lymph Nodes as 6-Sulfo Sialyl Lewis X," The Journal of Biological Chemistry, vol. 273, No. 18, May 1, 1998, pp. 11225-11233.

Matsuura et al., Abstract of The 135th Annual Meeting of the Pharmaceutical society of Japan, 2015, pp. ROMBUNNO. 27X-PM05S.

Kataoka et al., "The Nucleotide Sequences of Rearranged and Germline Immunoglobulin $V_H$ Genes of a Mouse Myeloma MC101 and Evolution of $V_H$ Genes in Mouse," The Journal of Biological Chemistry, vol. 257, No. 1, Jan. 10, 1982, pp. 277-285.

Kawashima, Hiroto, Collection of Research Reports of the Uehara Memorial Foundation, 32, 2018.

(Continued)

*Primary Examiner* — Michael Szperka
(74) *Attorney, Agent, or Firm* — Foley & Lardner LLP

(57) ABSTRACT

The present invention provides an antibody or a fragment thereof, which specifically binds to a 6-sulfosialyl Lewis X glycan, where the binding requires fucose, a sulfate group, and a sialic acid that form the 6-sulfosialyl Lewis X glycan.

27 Claims, 23 Drawing Sheets

Specification includes a Sequence Listing.

(56) References Cited

OTHER PUBLICATIONS

Rudikoff et al., "k chain joining segments and structural diversity of antibody combining sites," Proc. Natl. Acad. Sci. USA, vol. 77, No. 7, Jul. 1980, pp. 4270-4274.
European Extended Search Report issued in corresponding European Patent Application No. 21877636.7 dated Sep. 20, 2024 (16 pages).
Hirakawa et al., "Anti-sulfated-glycan monoclonal antibody S2 inhibits lymphocyte recruitment to nasal-associated lymphoid tissues and attenuates allergic rhinitis" The Journal of Immunology I American Association of Immunologists, The Journal of Immunology, XP093202647, vol. 200, No. 1, Supplement, May 1, 2018, pp. 102.8-102.8.
Hirakawa et al., "GLYCO 24 ED—Kanie Osamu", Glycoconjugate Journal, Chapman & Hall, Boston, XP036320693, vol. 34, No. 1, Jul. 27, 2017, pp. 1-120.
Kawashima et al., "Sulfated glycans control lymphocyte homing", Annals of the New York Academy of Sciences, New York Academy of Sciences, US, XP071408845, vol. 1253, No. 1, Jan. 30, 2012, pp. 112-121.
Liu et al., "A novel monoclonal antibody against 6-sulfo sialyl Lewis x glycans attenuates murine allergic rhinitis by suppressing Th2 immune responses", Scientific Reports, XP093202380, vol. 13, No. 1, Sep. 21, 2023, pp. 1-13.
Liu et al., "Prevention of experimental autoimmune encephalomyelitis by targeting 6-sulfo sialyl Lewis X glycans involved in lymphocyte homing", International Immunology Jun. 2010, XP093202381, vol. 36, No. 6, Feb. 22, 2024, pp. 303-316.
Ni et al., "The Monoclonal Antibody CHO-131 Identifies a Subset of Cutaneous Lymphocyte-Associated Antigen T Cells Enriched in p. Selectin-Binding Cells", The Journal of Immunology, XP093202994 vol. 177, No. 7, Oct. 1, 2006, pp. 4742-4748.
Wei et al., "Prevention of Collagen-Induced Arthritis by an Anti-Glycan Monoclonal Antibody Reactive with 6-Sulfo Sialyl Lewis x in DBA/1 Mice", Monoclonal Antibodies in Immunodiagnosis and Immunotherapy, XP093202493, vol. 43, No. 1, Feb. 1, 2024, pp. 3-9.

* cited by examiner

*FIG. 7*

| | CDR1 | CDR2 | CDR3 |
|---|---|---|---|
| **HEAVY CHAIN** | GFSLTSYA **(SEQ ID NO: 1)** | IWGGGST **(SEQ ID NO: 2)** | AKHEKLGRFPY **(SEQ ID NO: 3)** |
| **LIGHT CHAIN** | SSVSY **(SEQ ID NO: 4)** | EIS **(SEQ ID NO: 5)** | QQWNYPLAT **(SEQ ID NO: 6)** |

*FIG. 8*

SF1 HEAVY CHAIN VARIABLE REGION (SEQ ID NO: 13)

QVQLKESGPGLVAPSQSLSITCTVSGFSLTSYAVHWVRQP
PGKGLEWLGIIWGGGSTNYNSALMSRLSISKDNSKSQVFL
KMNSLQTDDTAMYYCAKHEKLGRFPYWGQGTLVTVSA

*FIG. 9*

SF1 LIGHT CHAIN VARIABLE REGION (SEQ ID NO: 14)

EIVLTQSPAITAASLGQKVTITCSASSSVSYMHWYQQKSG
TSPKPWIYEISKLASGVPARFSGSGSGTSYSLTISSMEAE
DAAIYYCQQWNYPLATFGGGTKLEIK

FIG. 21

HUMANIZED SF1 HEAVY CHAIN VARIABLE REGION H1 (SEQ ID NO: 15)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSS

HUMANIZED SF1 HEAVY CHAIN VARIABLE REGION H2 (SEQ ID NO: 16)

QVQLQESGPGLVKPSETLSLTCTVSGFSLTSYAVHWIRQP
PGKGLEWIGIIWGGGSTNYNSALKSRVTISKDNSKSQVSL
KLSSVTAADTAVYYCAKHEKLGRFPYWGQGTLVTVSS

HUMANIZED SF1 HEAVY CHAIN VARIABLE REGION H3 (SEQ ID NO: 17)

QVQLVESGGGVVQPGGSLRLSCAVSGFSLTSYAVHWVRQA
PGKGLEWLGIIWGGGSTNYNSAVKGRFTISKDNSKSSVYL
QMNSLRTEDTALYYCAKHEKLGRFPYWGQGTLVTVSS

HUMANIZED SF1 LIGHT CHAIN VARIABLE REGION L1 (SEQ ID NO: 18)

EIQLTQSPSSLSASVGDRVTITCRASSSVSYMHWYQQKPG
KAPKPLIYEISKLASGVPSRFSGSGSGTDYTLTISSLQPE
DFATYYCQQWNYPLATFGGGTKLEIK

HUMANIZED SF1 LIGHT CHAIN VARIABLE REGION L2 (SEQ ID NO: 19)

DIQLTQSPSSLSASVGDRVTITCRASSSVSYMHWYQQKPG
KAPKPLIYEISKLASGVPSRFSGSGSGTDYTLTISSLQPE
DFATYYCQQWNYPLATFGGGTKLEIK

HUMANIZED SF1 LIGHT CHAIN VARIABLE REGION L3 (SEQ ID NO: 20)

EIVLTQSPDFQSVTPKEKVTITCRASSSVSYMHWYQQKPD
QSPKPLIYEISKLASGVPSRFSGSGSGTDYTLTINSLEAE
DAATYYCQQWNYPLATFGGGTKLEIK

FIG. 22

HUMANIZED SF1-scFv-H1L1 (SEQ ID NO: 21)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSSGGG
GSGGGGSGGGGSEIQLTQSPSSLSASVGDRVTITCRASSS
VSYMHWYQQKPGKAPKPLIYEISKLASGVPSRFSGSGSGT
DYTLTISSLQPEDFATYYCQQWNYPLATFGGGTKLEIKGL
QQGGTHHHHHH

HUMANIZED SF1-scFv-H1L2 (SEQ ID NO: 22)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSSGGG
GSGGGGSGGGGSDIQLTQSPSSLSASVGDRVTITCRASSS
VSYMHWYQQKPGKAPKPLIYEISKLASGVPSRFSGSGSGT
DYTLTISSLQPEDFATYYCQQWNYPLATFGGGTKLEIKGL
QQGGTHHHHHH

HUMANIZED SF1-scFv-H2L1 (SEQ ID NO: 23)

QVQLQESGPGLVKPSETLSLTCTVSGFSLTSYAVHWIRQP
PGKGLEWIGIIWGGGSTNYNSALKSRVTISKDNSKSQVSL
KLSSVTAADTAVYYCAKHEKLGRFPYWGQGTLVTVSSGGG
GSGGGGSGGGGSEIQLTQSPSSLSASVGDRVTITCRASSS
VSYMHWYQQKPGKAPKPLIYEISKLASGVPSRFSGSGSGT
DYTLTISSLQPEDFATYYCQQWNYPLATFGGGTKLEIKGL
QQGGTHHHHHH

HUMANIZED SF1-scFv-H3L3 (SEQ ID NO: 24)

QVQLVESGGGVVQPGGSLRLSCAVSGFSLTSYAVHWVRQA
PGKGLEWLGIIWGGGSTNYNSAVKGRFTISKDNSKSSVYL
QMNSLRTEDTALYYCAKHEKLGRFPYWGQGTLVTVSSGGG
GSGGGGSGGGGSEIVLTQSPDFQSVTPKEKVTITCRASSS
VSYMHWYQQKPDQSPKPLIYEISKLASGVPSRFSGSGSGT
DYTLTINSLEAEDAATYYCQQWNYPLATFGGGTKLEIKGL
QQGGTHHHHHH

*FIG. 23*

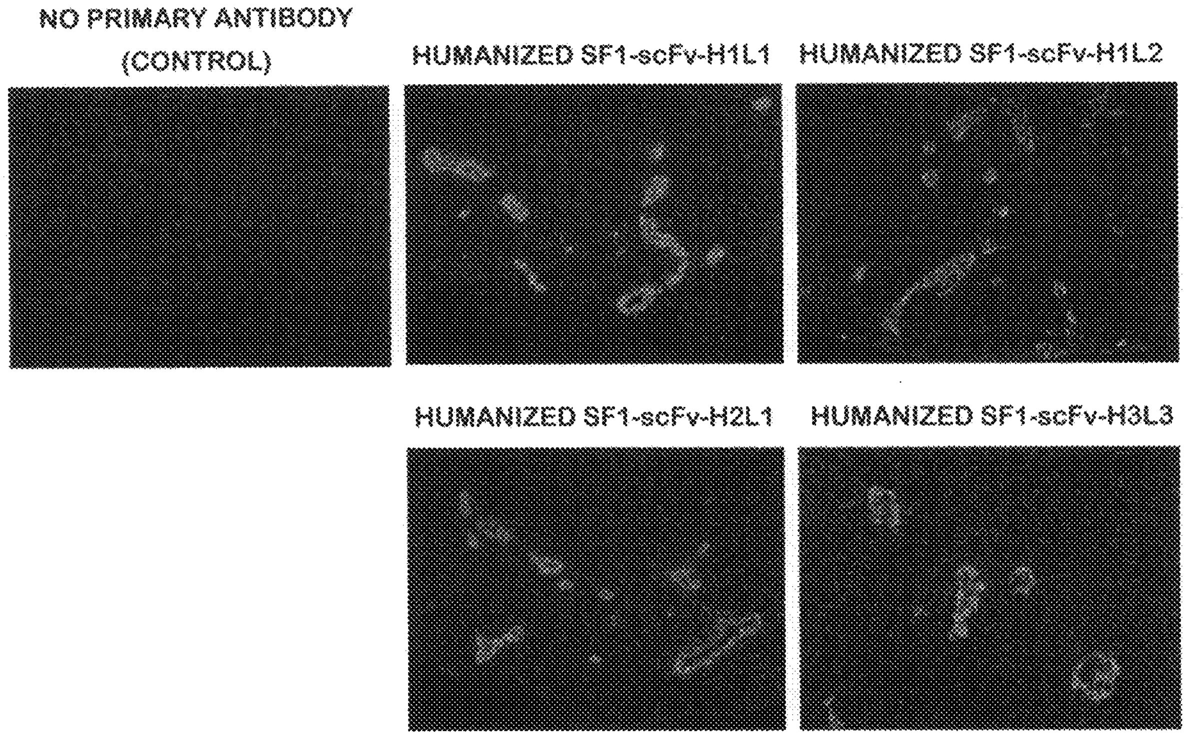

*FIG. 24*

HUMANIZED SF1 HEAVY CHAIN FULL LENGTH (SEQ ID NO: 25)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSSAST
KGPSVFPLAPSSKSTSGGTAALGCLVKDYFPEPVTVSWNS
GALTSGVHTFPAVLQSSGLYSLSSVVTVPSSSLGTQTYIC
NVNHKPSNTKVDKKVEPKSCDKTHTCPPCPAPELLGGPSV
FLFPPKPKDTLMISRTPEVTCVVVDVSHEDPEVKFNWYVD
GVEVHNAKTKPREEQYNSTYRVVSVLTVLHQDWLNGKEYK
CKVSNKALPAPIEKTISKAKGQPREPQVYTLPPSRDELTK
NQVSLTCLVKGFYPSDIAVEWESNGQPENNYKTTPPVLDS
DGSFFLYSKLTVDKSRWQQGNVFSCSVMHEALHNHYTQKS
LSLSPGK

HUMANIZED SF1 LIGHT CHAIN FULL LENGTH (SEQ ID NO: 26)

EIQLTQSPSSLSASVGDRVTITCRASSSVSYMHWYQQKPG
KAPKPLIYEISKLASGVPSRFSGSGSGTDYTLTISSLQPE
DFATYYCQQWNYPLATFGGGTKLEIKRTVAAPSVFIFPPS
DEQLKSGTASVVCLLNNFYPREAKVQWKVDNALQSGNSQE
SVTEQDSKDSTYSLSSTLTLSKADYEKHKVYACEVTHQGL
SSPVTKSFNRGEC

FIG. 29

HUMANIZED SF1 HEAVY CHAIN IgG1-LALA VARIANT FULL LENGTH (SEQ ID NO: 27)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSSAST
KGPSVFPLAPSSKSTSGGTAALGCLVKDYFPEPVTVSWNS
GALTSGVHTFPAVLQSSGLYSLSSVVTVPSSSLGTQTYIC
NVNHKPSNTKVDKKVEPKSCDKTHTCPPCPAPEAAGGPSV
FLFPPKPKDTLMISRTPEVTCVVVDVSHEDPEVKFNWYVD
GVEVHNAKTKPREEQYNSTYRVVSVLTVLHQDWLNGKEYK
CKVSNKALPAPIEKTISKAKGQPREPQVYTLPPSRDELTK
NQVSLTCLVKGFYPSDIAVEWESNGQPENNYKTTPPVLDS
DGSFFLYSKLTVDKSRWQQGNVFSCSVMHEALHNHYTQKS
LSLSPGK

FIG. 30

HUMANIZED SF1 HEAVY CHAIN IgG4-SPLE VARIANT FULL LENGTH (SEQ ID NO: 28)

QVQLQESGPGLVKPSETLSLTCTVSGFSLTSYAVHWVRQP
PGKGLEWLGIIWGGGSTNYNSALKSRVTISKDNSKSQVSL
KLSSVTAADTAVYYCAKHEKLGRFPYWGQGTLVTVSSAST
KGPSVFPLAPCSRSTSESTAALGCLVKDYFPEPVTVSWNS
GALTSGVHTFPAVLQSSGLYSLSSVVTVPSSSLGTKTYTC
NVDHKPSNTKVDKRVESKYGPPCPPCPAPEFEGGPSVFLF
PPKPKDTLMISRTPEVTCVVVDVSQEDPEVQFNWYVDGVE
VHNAKTKPREEQFNSTYRVVSVLTVLHQDWLNGKEYKCKV
SNKGLPSSIEKTISKAKGQPREPQVYTLPPSQEEMTKNQV
SLTCLVKGFYPSDIAVEWESNGQPENNYKTTPPVLDSDGS
FFLYSRLTVDKSRWQEGNVFSCSVMHEALHNHYTQKSLSL
SLGK

ANTI-GLYCAN ANTIBODY AND USE THEREOF

CROSS-REFERENCE TO RELATED APPLICATIONS

The present application claims priority under 35 U.S.C. § 371 to International Patent Application No. PCT/JP2021/036893, filed Oct. 6, 2021, which claims priority to and the benefit of Japanese Patent Application No. 2020-169966, filed on Oct. 7, 2020. The contents of these applications are hereby incorporated by reference in their entireties.

INCORPORATION OF SEQUENCE LISTING

The material in the accompanying sequence listing is hereby incorporated by reference into this application. The accompanying sequence listing ASCII file, named 135978-0102_ST25, was created on Mar. 30, 2026, and is 34,022 bytes in size.

TECHNICAL FIELD

The present invention broadly relates to a novel antibody targeting a glycan, particularly an antibody or a fragment thereof, which specifically binds to a 6-sulfosialyl Lewis X glycan, where the binding requires fucose, a sulfate group, and a sialic acid that form the 6-sulfosialyl Lewis X glycan, and use thereof, and the like.

BACKGROUND ART

The pathological mechanisms of many immune-related diseases are still unclear, and above all, an autoimmune disease is one of the diseases with high unmet medical needs. Among autoimmune diseases, regarding the treatment of multiple sclerosis, natalizumab, which is an antibody against VLA-4 integrin being an adhesion molecule that controls infiltration of inflammatory cells into the central nervous system, exhibits an effect of improving the pathology, but may cause progressive multifocal leukoencephalopathy due to JC virus infection. In addition, fingolimod (FTY720), which is a low-molecular weight drug, has been shown to be effective as a therapeutic agent for multiple sclerosis, but a side effect such as an infection or bradyarrhythmia is also known, and development of a novel therapeutic agent with a different mechanism of action has been demanded. The mechanism of action of FTY720 is to retain antigen-sensitized lymphocytes in lymph nodes, but it is considered that if the process of migration of lymphocytes into lymph nodes (lymphocyte homing) can be suppressed, antigen sensitization in lymph nodes is suppressed, which may lead to the fundamental treatment of various immune-related diseases including multiple sclerosis. However, to date, it is not clear whether an immune-related disease such as an autoimmune disease can be treated by inhibition of lymphocyte homing to lymph nodes.

In the immune system, a large number of immune cells circulate in the body via blood and lymph, and monitor foreign antigens. Above all, a phenomenon in which lymphocytes circulating in peripheral blood migrate to secondary lymphoid tissues is called lymphocyte homing, and is strictly controlled by a multistep adhesion molecule cascade. Therefore, it is important to understand such an adhesion molecule cascade for understanding the biokinetics and tissue tropism of lymphocytes.

The lymphocyte homing is a biological defense mechanism provided for efficiently inducing an immune response, and when lymphocytes migrate to a secondary lymphoid tissue such as a peripheral lymph node, a mesenteric lymph node, or a Peyer's patch, after adhering to a high endothelial venule (HEV) composed of an endothelial cell in a special dice shape, the lymphocytes infiltrate into the tissue.

It is considered that, if the specific adhesion between the lymphocyte and HEV can be suppressed by inhibiting lymphocyte homing, for example, the allergic response of the living body can be controlled, which may be useful in the treatment of various diseases. However, since various factors are involved in the onset of an immune-related disease such as an autoimmune disease or an allergic disease, it is not clear whether such an immune-related disease can be treated by inhibiting lymphocyte homing.

In the adhesion molecule cascade, 6-sulfosialyl Lewis X is responsible for initial adhesion to a high endothelial venule that mediates lymphocyte infiltration, and therefore is a glycan structure essential for lymphocyte homing. The present inventors produced a mouse deficient in a gene of a sulfotransferase that transfers a sulfate group to a glycan, and demonstrated that 6-sulfosialyl Lewis X, which is a sulfated glycan specifically expressed in HEV, plays an essential role in the homing of lymphocytes to a secondary lymphoid tissue and the onset of contact dermatitis (NPL 1: Kawashima et al., Nat. Immunol., 11:1096-1104, 2005).

An antibody that recognizes HEV is also known, but the amount of a glycan expressed in vivo is very small and its binding modes are diverse, so that the glycan structures recognized by the antibody differ. For example, MECA-79 (NPL 2: Streeter et al., J. Cell Biol., 107:1853-1862, 1988), which specifically stains HEV in a peripheral lymph node recognizes 6-sulfosialyl Lewis X only when it is present on a special O-linked glycan called extended core 1 structure. In addition, for the recognition thereof, a sulfate group in 6-sulfosialyl Lewis X is required, but in the glycan that forms 6-sulfosialyl Lewis X, fucose and a sialic acid, which play an important role in lymphocyte homing, are not required. Further, an S1 antibody and an S2 antibody (NPL 3: Hirakawa et al., J. Biol. Chem., 285:40864-40878, 2010) also recognize 6-sulfosialyl Lewis X, and for the recognition thereof, a sulfate group and a sialic acid in 6-sulfosialyl Lewis X are required, but fucose is not required. Therefore, it cannot be denied that these antibodies bind not only to HEV but also to a tissue expressing a 6-sulfosialyl LacNAc glycan lacking fucose, and may cause an unexpected side effect other than inhibition of lymphocyte homing in vivo. Moreover, an F1 antibody and an F2 antibody, which are anti-sialyl Lewis X monoclonal antibodies (NPL 4: Matsumura et al., J. Biol. Chem., 290:15313-15326, 2015) also recognize 6-sulfosialyl Lewis X, but for the recognition thereof, a sulfate group in 6-sulfosialyl Lewis X is not required, and they recognize unsulfated sialyl Lewis X. Therefore, these antibodies not only bind to HEV to inhibit lymphocyte homing, but also bind to a leukocyte expressing sialyl Lewis X to inhibit also P-selectin- or E-selectin-dependent leukocyte rolling.

The S1 antibody and S2 antibody are both IgM class antibodies, and therefore, it is difficult to prepare them in a large amount with high purity, so that it is difficult to verify the therapeutic effect on an immune-related disease such as an autoimmune disease that requires frequent administration, and the therapeutic effect on an immune-related disease such as an autoimmune disease is unknown.

In addition, other than the S1 antibody and the S2 antibody, antibodies having binding affinity for 6-sulfosialyl Lewis X are known (NPLs 2, 4, 5, and 6), but the therapeutic effect of these antibodies on an immune-related disease such as an autoimmune disease is also unknown.

CITATION LIST

Non Patent Literature

NPL 1: Kawashima et al., Nat. Immunol., 11:1096-1104, 2005
NPL 2: Streeter et al., J. Cell Biol., 107:1853-1862, 1988
NPL 3: Hirakawa et al., J. Biol. Chem., 285:40864-40878, 2010
NPL 4: Matsumura et al., J. Biol. Chem., 290:15313-15326, 2015
NPL 5: Mitsuoka et al., J. Biol. Chem., 273:11225-11233, 1998
NPL 6: Hiroaki Matsuura et al., Abstracts of 135th Annual Meeting of Pharmaceutical Society of Japan (CD-ROM), page: ROMBUNNO. 27X-PM05S, 2015

SUMMARY OF INVENTION

Technical Problem

An object of the invention is to discover a glycan to serve as an effective therapeutic target for an immune-related disease such as multiple sclerosis, and also to provide a novel antibody targeting the glycan, particularly an antibody or a fragment thereof, which specifically binds to a 6-sulfosialyl Lewis X glycan, where the binding requires fucose, a sulfate group, and a sialic acid that form the 6-sulfosialyl Lewis X glycan, and use thereof and the like.

Solution to Problem

The present inventor produced a plurality of antibodies using a method invented by the present inventors, in which a glycan synthase-deficient mouse is immunized with a cell made to overexpress the glycan synthase. Among the antibodies, by an immunohistochemical study, an IgG1 class anti-glycan monoclonal antibody (SF1 antibody) that specifically binds to HEV expressing a 6-sulfosialyl Lewis X glycan was selected, and its binding specificity and sequence were analyzed. As a result, it was revealed that the obtained anti-glycan antibody has a novel sequence, recognizes 6-sulfosialyl Lewis X, and simultaneously requires the following three members: fucose, a sulfate group, and a sialic acid that form a 6-sulfosialyl Lewis X glycan for the recognition, and strictly distinguishes 6-sulfosialyl Lewis X from other glycan structures. As a result of an analysis by biolayer interferometry, it was shown that the $K_D$ value for the binding of the SF1 antibody to 6-sulfosialyl Lewis X is $6.09\times10^{-9}$ (M).

The present inventor revealed that the SF1 antibody inhibits the binding of L-selectin, which is a lymphocyte homing receptor, to HEV and has the activity of inhibiting the L-selectin-dependent rolling of lymphocytes on 6-sulfosialyl Lewis X-expressing cells, and is effective in inhibiting lymphocyte homing.

Subsequently, the present inventor focused on the possibility that a glycan involved in lymphocyte homing can serve as an effective therapeutic target for an immune-related disease such as multiple sclerosis, and performed an analysis of experimental autoimmune encephalomyelitis using a sulfotransferase GlcNAc6ST-1/2 double-deficient mouse in which lymphocyte homing is markedly reduced due to defective synthesis of a 6-sulfosialyl Lewis X glycan involved in lymphocyte homing. As a result, it was found that the 6-sulfosialyl Lewis X glycan synthesized by GlcNAc6ST-1/2 serves as a therapeutic target for an immune-related disease such as multiple sclerosis.

Therefore, the present inventor multilaterally studied the therapeutic effect of the SF1 antibody on an immune-related disease by a non-clinical study using an animal model. As a result, it was found that the antibody has significant preventive and therapeutic effects on experimental autoimmune encephalomyelitis. In addition, it was revealed that the antibody has a disease suppressive effect also in a rheumatoid arthritis model and an allergic rhinitis model. From the above, it was revealed that the SF1 antibody specifically binds to a 6-sulfosialyl Lewis X glycan and specifically inhibits lymphocyte homing to lymph nodes, so as to exhibit a remarkable therapeutic effect on an immune-related disease such as an autoimmune disease and an allergic disease.

The present inventor performed immunohistological staining of human normal tissues using the SF1 antibody and revealed that the SF1 antibody specifically binds to a human peripheral lymph node and tonsil HEV.

Since the SF1 antibody is a mouse antibody, humanization of the antibody is important for use in treatment of a human immune-related disease. Then, when the present inventor further produced a humanized single-chain SF1 antibody in which the sequence of a hypervariable region of the SF1 antibody was grafted into the frame sequence of a human antibody variable region, it was revealed that the antibody retains specific binding affinity for HEV. Then, when a completely humanized SF1 antibody in which the sequence of the variable region thereof was replaced with a human IgG1 heavy chain and a human k light chain was produced, it was revealed that the antibody exhibits specific binding affinity for HEV in a sulfate group- and fucose-dependent manner and retains specific binding specificity for a 6-sulfosialyl Lewis X glycan.

Subsequently, the present inventor revealed that the humanized SF1 antibody is effective in inhibiting lymphocyte homing and suppressing the onset of experimental autoimmune encephalomyelitis in the same manner as the mouse SF1 antibody.

Further, the present inventor produced a humanized SF1 antibody in which the sequence of the Fc region was modified to a sequence known to reduce the effector activity mediated by the Fc region of the antibody and reduce the risk of side effects, and found that the antibody retains specific tissue binding affinity. It is considered that such a humanized SF1 antibody with a modified Fc region sequence is useful as a therapeutic antibody for an immune-related disease such as an autoimmune disease or an allergic disease.

That is, the invention of this application includes the following inventions.

[1]

An antibody or a fragment thereof, which specifically binds to a 6-sulfosialyl Lewis X glycan, where the binding requires fucose, a sulfate group, and a sialic acid that form the 6-sulfosialyl Lewis X glycan, wherein the antibody or the fragment thereof contains at least one or more CDRs selected from the group consisting of the following CDRs:

(a) CDRH1 including the amino acid sequence represented by SEQ ID NO: 1;
(b) CDRH2 including the amino acid sequence represented by SEQ ID NO: 2;
(c) CDRH3 including the amino acid sequence represented by SEQ ID NO: 3;

(d) CDRL1 including the amino acid sequence represented by SEQ ID NO: 4;
(e) CDRL2 including the amino acid sequence represented by SEQ ID NO: 5; and
(f) CDRL3 including the amino acid sequence represented by SEQ ID NO: 6, or
contains at least one or more CDRs, each including an amino acid sequence having deletion, substitution, or addition of one or several amino acids in the amino acid sequence of the corresponding CDR, or
contains at least one or more CDRs, each including an amino acid sequence having 80% or more identity to the amino acid sequence of the corresponding CDR.

[2]

The antibody or the fragment thereof according to [1], which includes a heavy chain variable region containing the following CDRs:
(a) CDRH1 including the amino acid sequence represented by SEQ ID NO: 1;
(b) CDRH2 including the amino acid sequence represented by SEQ ID NO: 2; and
(c) CDRH3 including the amino acid sequence represented by SEQ ID NO: 3, or
includes a heavy chain variable region containing CDRH1, CDRH2, and CDRH3, each including an amino acid sequence having deletion, substitution, or addition of one or several amino acids in the amino acid sequence of the corresponding CDR, or
includes a heavy chain variable region containing CDRH1, CDRH2, and CDRH3, each including an amino acid sequence having 80% or more identity to the amino acid sequence of the corresponding CDR.

[3]

The antibody or the fragment thereof according to [2], wherein the heavy chain variable region contains at least 90 consecutive amino acids in the amino acid sequence represented by any of SEQ ID NOS: 13, and 15 to 17.

[4]

The antibody or the fragment thereof according to [2] or [3], wherein the heavy chain variable region includes the amino acid sequence represented by any of SEQ ID NOS: 13, and 15 to 17, an amino acid sequence having deletion, substitution, or addition of one or several amino acids in the amino acid sequence represented by any of SEQ ID NOS: 13, and 15 to 17, or an amino acid sequence having 80% or more identity to the amino acid sequence represented by any of SEQ ID NOS: 13, and 15 to 17.

[5]

The antibody or the fragment thereof according to any one of [2] to [4], wherein the heavy chain includes the amino acid sequence represented by SEQ ID NO: 25, 27, or 28, an amino acid sequence having deletion, substitution, or addition of one or several amino acids in the amino acid sequence represented by SEQ ID NO: 25, 27, or 28, or an amino acid sequence having 80% or more identity to the amino acid sequence represented by SEQ ID NO: 25, 27, or 28.

[6]

The antibody or the fragment thereof according to any one of [1] to [5], which includes a light chain variable region containing the following CDRs:
(d) CDRL1 including the amino acid sequence represented by SEQ ID NO: 4;
(e) CDRL2 including the amino acid sequence represented by SEQ ID NO: 5; and
(f) CDRL3 including the amino acid sequence represented by SEQ ID NO: 6, or
includes a light chain variable region containing CDRL1, CDRL2, and CDRL3, each including an amino acid sequence having deletion, substitution, or addition of one or several amino acids in the amino acid sequence of the corresponding CDR, or
includes a light chain variable region containing CDRL1, CDRL2, and CDRL3, each including an amino acid sequence having 80% or more identity to the amino acid sequence of the corresponding CDR.

[7]

The antibody or the fragment thereof according to [6], wherein the light chain variable region contains at least 80 consecutive amino acids in the amino acid sequence represented by any of SEQ ID NOS: 14, and 18 to 20.

[8]

The antibody or the fragment thereof according to [6] or [7], wherein the light chain variable region includes the amino acid sequence represented by any of SEQ ID NOS: 14, and 18 to 20, an amino acid sequence having deletion, substitution, or addition of one or several amino acids in the amino acid sequence represented by any of SEQ ID NOS: 14, and 18 to 20, or an amino acid sequence having 80% or more identity to the amino acid sequence represented by any of SEQ ID NOS: 14, and 18 to 20.

[9]

The antibody or the fragment thereof according to any one of [6] to [8], wherein the light chain includes the amino acid sequence represented by SEQ ID NO: 26, an amino acid sequence having deletion, substitution, or addition of one or several amino acids in the amino acid sequence represented by SEQ ID NO: 26, or an amino acid sequence having 80% or more identity to the amino acid sequence represented by SEQ ID NO: 26.

[10]

The antibody or the fragment thereof according to any one of [1] to [9], which contains CDR containing the following CDRs:
(a) CDRH1 including the amino acid sequence represented by SEQ ID NO: 1;
(b) CDRH2 including the amino acid sequence represented by SEQ ID NO: 2;
(c) CDRH3 including the amino acid sequence represented by SEQ ID NO: 3;
(d) CDRL1 including the amino acid sequence represented by SEQ ID NO: 4;
(e) CDRL2 including the amino acid sequence represented by SEQ ID NO: 5; and
(f) CDRL3 including the amino acid sequence represented by SEQ ID NO: 6, or
contains CDRH1, CDRH2, and CDRH3 and CDRL1, CDRL2, and CDRL3, each including an amino acid sequence having deletion, substitution, or addition of one or several amino acids in the amino acid sequence of the corresponding CDR, or
contains CDRH1, CDRH2, and CDRH3 and CDRL1, CDRL2, and CDRL3, each including an amino acid sequence having 80% or more identity to the amino acid sequence of the corresponding CDR.

[11]

The antibody or the fragment thereof according to any one of [1] to [10], which inhibits binding of a high endothelial venule expressing a 6-sulfosialyl Lewis X glycan to L-selectin.

[12]

The antibody or the fragment thereof according to any one of [1] to [11], wherein a constant region is derived from a human.

[13]

The antibody or the fragment thereof according to any one of [1] to [12], which is humanized.

[14]

The antibody or the fragment thereof according to any one of [1] to [13], which is selected from the group consisting of Fab, F(ab')2, Fab', Fv, and a single-chain antibody.

[15]

The antibody or the fragment thereof according to [14], wherein the single-chain antibody includes an amino acid sequence at positions 1 to 117 and 133 to 238 in the amino acid sequence represented by any of SEQ ID NOS: 21 to 24, an amino acid sequence having deletion, substitution, or addition of one or several amino acids in an amino acid sequence at positions 1 to 117 and 133 to 238 in the amino acid sequence represented by any of SEQ ID NOS: 21 to 24, or an amino acid sequence having 80% or more identity to an amino acid sequence at positions 1 to 117 and 133 to 238 in the amino acid sequence represented by any of SEQ ID NOS: 21 to 24.

[16]

The antibody or the fragment thereof according to any one of [1] to [15], wherein the antibody or the fragment thereof exhibits a dissociation constant ($K_D$ value) of $1\times10^{-6}$ M or less for the 6-sulfosialyl Lewis X glycan.

[17]

A polynucleotide encoding the antibody or the fragment thereof according to any one of [1] to [16].

[18]

An expression vector, containing the polynucleotide according to [17].

[19]

A host cell transfected with the expression vector according to [18].

[20]

The host cell according to [19], which is a eukaryotic cell.

[21]

A hybridoma producing the antibody according to any one of [1] to [16].

[22]

A lymphocyte homing inhibitor, containing the antibody or the fragment thereof according to any one of [1] to [16], the polynucleotide according to [17], or the expression vector according to [18].

[23]

A pharmaceutical composition, containing the antibody or the fragment thereof according to any one of [1] to [16], the polynucleotide according to [17], or the expression vector according to [18].

[24]

The pharmaceutical composition according to [23], for treating or preventing a disease caused by an overactive immune response mediated by lymphocyte homing.

[25]

The pharmaceutical composition according to [24], wherein the disease caused by an overactive immune response mediated by lymphocyte homing is an immune-related disease.

[26]

The pharmaceutical composition according to [25], wherein the immune-related disease is an allergic disease or an autoimmune disease.

[27]

The pharmaceutical composition according to [26], wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

[28]

The pharmaceutical composition according to [26], wherein the immune-related disease is an autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenia purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; nonarticular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

[29]

The pharmaceutical composition according to [28], wherein the autoimmune disease is multiple sclerosis or a collagen disease.

[30]

The pharmaceutical composition according to [28] or [29], wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

[31]

The pharmaceutical composition according to any one of [24] to [30], further containing an agent for treating or preventing a disease caused by an overactive immune response mediated by lymphocyte homing.

[32]

A method for producing the antibody or the fragment thereof according to any one of [1] to [16], including a step of culturing the host cell according to [19] or [20], or the hybridoma according to [21].

[33]

A pharmaceutical composition for treating or preventing a disease caused by an overactive immune response mediated by lymphocyte homing, containing an antibody or a fragment thereof, which specifically binds to a 6-sulfosialyl Lewis X glycan, where the binding requires fucose, a sulfate group, and a sialic acid that form the 6-sulfosialyl Lewis X glycan, a polynucleotide encoding the antibody or the fragment thereof, or an expression vector containing the polynucleotide.

[34]

The pharmaceutical composition according to [33], wherein the disease caused by an overactive immune response mediated by lymphocyte homing is an immune-related disease.

[35]

The pharmaceutical composition according to [34], wherein the immune-related disease is an allergic disease or an autoimmune disease.

[36]

The pharmaceutical composition according to [35], wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

[37]

The pharmaceutical composition according to [35], wherein the immune-related disease is any autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopeniapurpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; nonarticular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

[38]

The pharmaceutical composition according to [37], wherein the autoimmune disease is multiple sclerosis or a collagen disease.

[39]

The pharmaceutical composition according to [38], wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

[40]

The pharmaceutical composition according to any one of [33] to [39], wherein the antibody or the fragment thereof inhibits binding of a high endothelial venule expressing a 6-sulfosialyl Lewis X glycan to L-selectin.

[41]

The pharmaceutical composition according to any one of [33] to [40], wherein the antibody or the fragment thereof is the antibody or the fragment thereof according to any one of [1] to [16].

[42]

A method for treating or preventing a disease caused by an overactive immune response mediated by lymphocyte homing in a subject, including a step of administering an effective amount of an antibody or a fragment thereof, which specifically binds to a 6-sulfosialyl Lewis X glycan, where the binding requires fucose, a sulfate group, and a sialic acid that form the 6-sulfosialyl Lewis X glycan, a polynucleotide encoding the antibody or the fragment thereof, or an expression vector containing the polynucleotide to the subject.

[43]

The method according to [42], wherein the disease caused by an overactive immune response mediated by lymphocyte homing is an immune-related disease.

[44]

The method according to [43], wherein the immune-related disease is an allergic disease or an autoimmune disease.

[45]

The method according to [44], wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

[46]

The method according to [44], wherein the immune-related disease is any autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenia purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; non-articular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

[47]

The method according to [46], wherein the autoimmune disease is multiple sclerosis or a collagen disease.

[48]

The method according to [46] or [47], wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

[49]

The method according to any one of [42] to [48], wherein the antibody or the fragment thereof is the antibody or the fragment thereof according to any one of [1] to [16].

[50]

The method according to any one of [42] to [49], further including a step of administering an agent for treating or preventing a disease caused by an overactive immune response mediated by lymphocyte homing.

[51]

The antibody or the fragment thereof according to any one of [1] to [16], for use in treatment or prevention of a disease caused by an overactive immune response mediated by lymphocyte homing.

[52]

The antibody or the fragment thereof according to [51], wherein the disease caused by an overactive immune response mediated by lymphocyte homing is an immune-related disease.

[53]

The antibody or the fragment thereof according to [52], wherein the immune-related disease is an allergic disease or an autoimmune disease.

[54]

The antibody or the fragment thereof according to [53], wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

[55]

The antibody or the fragment thereof according to [53], wherein the immune-related disease is an autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenia purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; nonarticular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

[56]

The antibody or the fragment thereof according to [55], wherein the autoimmune disease is multiple sclerosis or a collagen disease.

[57]

The antibody or the fragment thereof according to [55] or [56], wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

[58]

Use of the antibody or the fragment thereof according to any one of [1] to for producing a medicine for treating or preventing a disease caused by an overactive immune response mediated by lymphocyte homing.

[59]

The use according to [58], wherein the disease caused by an overactive immune response mediated by lymphocyte homing is an immune-related disease.

[60]

The use according to [59], wherein the immune-related disease is an allergic disease or an autoimmune disease.

[61]

The use according to [59], wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

[62]

The use according to [59], wherein the immune-related disease is an autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenic purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; nonarticular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

[63]

The use according to [62], wherein the autoimmune disease is multiple sclerosis or a collagen disease.

[64]

The use according to or [63], wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

Advantageous Effects of Invention

According to the anti-glycan antibody of the invention, the binding of L-selectin expressed on a lymphocyte to a glycan on a high endothelial venule (HEV) is inhibited, and treatment of an immune-related disease (for example, an autoimmune disease such as multiple sclerosis) by the inhibition of lymphocyte homing can be achieved.

BRIEF DESCRIPTION OF DRAWINGS

FIG. 7 shows the amino acid sequences of the hypervariable regions of the heavy chain and light chain variable regions of SF1 antibody.

FIG. 8 shows the amino acid sequence of the heavy chain variable region of SF1 antibody.

FIG. 9 shows the amino acid sequence of the light chain variable region of SF1 antibody.

FIG. 21 shows the amino acid sequences of the heavy chain variable regions and the light chain variable regions of humanized SF1 antibodies.

FIG. 22 shows the amino acid sequences of humanized SF1 single-chain antibodies (scFvs).

FIG. 23 shows the results of fluorescent immunostaining of mouse lymph nodes with the humanized SF1 single-chain antibodies (scFvs).

FIG. 24 shows the full-length amino acid sequence of the heavy chain of the humanized SF1 antibody.

FIG. 29 shows the full-length amino acid sequence of a heavy chain IgG1-LALA variant of the humanized SF1 antibody.

FIG. 30 shows the full-length amino acid sequence of a heavy chain IgG4-SPLE variant of the humanized SF1 antibody.

DESCRIPTION OF EMBODIMENTS (Anti-Glycan Antibody)

Figure 1:
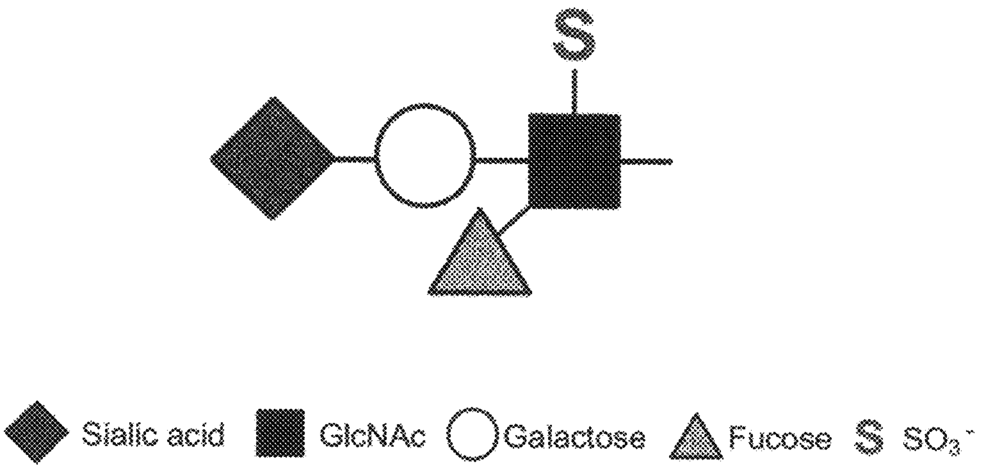
FIG. 1 is a schematic diagram of the structure of a 6-sulfosialyl Lewis X glycan.

In a first embodiment, an antibody or a fragment thereof, which specifically binds to a 6-sulfosialyl Lewis X glycan, where the binding requires fucose, a sulfate group, and a sialic acid that form the 6-sulfosialyl Lewis X glycan is provided. In the present description, this antibody is hereinafter also simply referred to as the anti-glycan antibody. As used herein, the description that the binding to 6-sulfosialyl Lewis X or the recognition of 6-sulfosialyl Lewis X "requires fucose, a sulfate group, and a sialic acid that form the 6-sulfosialyl Lewis X glycan" means that the antibody requires three members: fucose, a sulfate group, and a sialic acid for binding to 6-sulfosialyl Lewis X, and the binding activity to a glycan lacking even any one of fucose, a sulfate group, and a sialic acid from the 6-sulfosialyl Lewis X glycan decreases as compared to the binding activity to 6-sulfosialyl Lewis X.

The reactivity of the 6-sulfosialyl Lewis X glycan and the antibody can be measured by a conventional method, and for example, the measurement can be performed using a glycan array with glycans immobilized onto a substrate. The glycan array can be achieved, for example, using the Glycan Array of the US Consortium for Functional Glycomics. The reactivity of the 6-sulfosialyl Lewis X glycan and the antibody can also be evaluated using surface plasmon resonance or isothermal titration calorimetry.

In one embodiment, the dissociation constant ($K_D$ value) for the binding affinity of the antibody or the fragment thereof of the invention for the 6-sulfosialyl Lewis X glycan in the antigen-antibody reaction is generally $1\times10^{-6}$ M or less (for example, $1\times10^{-7}$ M or less, $1\times10^{-8}$ M or less, $1\times10^{-9}$ M or less, $1\times10^{-10}$ M or less, or $1\times10^{-11}$ M or less).

In one embodiment, the $K_D$ value for the binding affinity of the antibody or the fragment thereof of the invention for a glycan obtained by deleting at least one of fucose, a sulfate group, or a sialic acid from the 6-sulfosialyl Lewis X glycan (for example, 6-sulfo Lewis X, 6-sulfosialyl LacNAc, or sialyl Lewis X) is generally 10 times or more (for example, 102 times or more, 103 times or more, 104 times or more, or 105 times or more) greater than the $K_D$ value for the 6-sulfosialyl Lewis X glycan.

In one embodiment, the $K_D$ value for the binding affinity of the antibody or the fragment thereof of the invention for each of 6-sulfo Lewis X, 6-sulfosialyl LacNAc, and sialyl Lewis X is generally 10 times or more (for example, 102 times or more, 103 times or more, 104 times or more, or 105 times or more) greater than the $K_D$ value for the 6-sulfosialyl Lewis X glycan.

The $K_D$ value for the binding affinity of the antibody or the fragment thereof for a glycan antigen can be measured by analyzing the binding property of the antibody or the fragment thereof to a biotinylated glycan bound to a streptavidin biosensor through biolayer interferometry using Octet RED96 (manufactured by Pall-Fortebio LLC) in accordance with the below-mentioned Examples.

6-sulfosialyl Lewis X is a glycan in which a sialic acid, fucose, and a sulfate group are added to an N-acetyllactosamine (LacNAc) structure composed of galactose and N-acetylglucosamine (GlcNAc) (FIG. 1). Biosynthesis of 6-sulfosialyl Lewis X requires sulfation at the 6-position of N-acetylglucosamine, and N-acetylglucosamine-6-O-sulfotransferase (GlcNAc6ST)-1 to GlcNAc6ST-4 have been cloned in mice as a sulfotransferase (ST) that catalyzes sulfation.

In lymphocyte homing, lymphocytes infiltrate in lymph nodes through rolling (lymphocyte rolling) on high endothelial venules (HEV) via the specific binding of L-selectin expressed on the lymphocytes to 6-sulfosialyl Lewis X expressed in the HEV lumen. In this manner, the 6-sulfosialyl Lewis X, which is a sulfated glycan, is responsible for initial adhesion to HEV that mediates lymphocyte infiltration and therefore is a glycan structure essential for lymphocyte homing.

Fucose, a sulfate group, and a sialic acid are involved in the binding of L-selectin to the 6-sulfosialyl Lewis X glycan. Fucose, a sulfate group, and a sialic acid play an important role in lymphocyte homing, and therefore, the anti-glycan antibody or the fragment thereof that simultaneously recognizes the three members: fucose, a sulfate group, and a sialic acid highly efficiently inhibits lymphocyte homing, particularly lymphocyte homing from a cell expressing a 6-sulfosialyl Lewis X glycan, for example, a lymph node such as a peripheral lymph node or a mesenteric lymph node, or a high endothelial venule of a tonsil, and as a result, it is thought to be effective in the treatment or prevention of a disease caused by an overactive immune response mediated by lymphocyte homing. In a preferred embodiment, the anti-glycan antibody or the fragment thereof inhibits L-selectin-dependent lymphocyte rolling in the homing process.

The antibody, which specifically binds to a 6-sulfosialyl Lewis X glycan, where the binding requires fucose, a sulfate group, and a sialic acid that form the 6-sulfosialyl Lewis X glycan can be produced, for example, using a hybridoma obtained by immunizing a mouse deficient in sulfotransferases, GlcNAc6ST-1 and GlcNAc6ST-2, that are responsible for sulfation of sialyl Lewis X expressed in HEV (hereinafter also referred to as sulfotransferase double-deficient mouse or DKO mouse) with a cell made to express a sulfated glycan by introducing a fucosyltransferase gene and a sulfotransferase gene, and fusing an antibody-producing cell with a myeloma. The sulfotransferase double-deficient mouse can be produced using a method known to those skilled in the art, for example, a method described in Kawashima et al. (mentioned above). The produced antibody may be further subjected to an additional step such as a purification step prior to recovery, and for example, in order to increase the purity, it is preferred to perform salting out, filter filtration, clarification using centrifugation, affinity-based recovery, intermediate purification by ion exchange, and final purification by gel filtration.

As an example of the thus obtained anti-glycan antibody, an antibody having a complementarity determining region (CDR) that recognizes 6-sulfosialyl Lewis X, for example, an antibody that contains at least one or more CDRs selected from the group consisting of the following CDRs:

(a) CDRH1 including the amino acid sequence (GFSLTSYA) represented by SEQ ID NO: 1;

(b) CDRH2 including the amino acid sequence (IWGGGST) represented by SEQ ID NO: 2;

(c) CDRH3 including the amino acid sequence (AKHEKLGRFPY) represented by SEQ ID NO: 3;

(d) CDRL1 including the amino acid sequence (SSVSY) represented by SEQ ID NO: 4;

(e) CDRL2 including the amino acid sequence (EIS) represented by SEQ ID NO: 5; and (f) CDRL3 including the amino acid sequence (QQWNYPLAT) represented by SEQ ID NO: 6, preferably contains all six CDRs is exemplified. The antibody generally has a structure in which two heavy chains and two light chains are covalently bound via a disulfide bond, and each heavy chain is divided into a heavy chain variable region and a heavy chain constant region, and each light chain is divided into a light chain variable region and a light chain constant region. Three CDRs are contained in each variable region. Here, CDRH1, CDRH2, and CDRH3 denote the complementarity determining regions of the heavy chain in order from the amino terminal side of the heavy chain amino acid sequence, and CDRL1, CDRL2, and CDRL3 denote the complementarity determining regions of the light chain in order from the amino terminal side of the light chain amino acid sequence.

Therefore, the anti-glycan antibody or the fragment thereof preferably includes a heavy chain variable region containing (a) CDRH1 including the amino acid sequence (GFSLTSYA) represented by SEQ ID NO: 1, (b) CDRH2 including the amino acid sequence (IWGGGST) represented by SEQ ID NO: 2, and (c) CDRH3 including the amino acid sequence (AKHEKLGRFPY) represented by SEQ ID NO: 3, and/or includes a light chain variable region containing (d) CDRL1 including the amino acid sequence (SSVSY) represented by SEQ ID NO: 4, (e) CDRL2 including the amino acid sequence (EIS) represented by SEQ ID NO: 5, and (f) CDRL3 including the amino acid sequence (QQWNYPLAT) represented by SEQ ID NO: 6.

The amino acid sequence of each CDR may have deletion, substitution, or addition of one or several amino acids as long as the anti-glycan antibody or the fragment thereof specifically binds to a 6-sulfosialyl Lewis X glycan, and the binding requires fucose, a sulfate group, and a sialic acid that form the 6-sulfosialyl Lewis X glycan. As used herein, the term "several" varies depending on the length of the sequence, but refers to 2 to 10, preferably 2 to 5, and more preferably 2 or 3.

The amino acid after substitution is desirably an amino acid that conserves the properties of the original amino acid side chain as classified below. However, the amino acid substitution is not limited to conservative substitution.

hydrophobic amino acids (A, I, L, M, F, P, W, Y, V);
hydrophilic amino acids (R, D, N, C, E, Q, G, H, K, S, T);
amino acids having an aliphatic side chain (G, A, V, L, I, P);
amino acids having a hydroxy group-containing side chain (S, T, Y);
amino acids having a sulfur atom-containing side chain (C, M);
amino acids having a carboxylic acid and amide-containing side chain (D, N, E, Q);
amino acids having a base-containing side chain (R, K, H);
amino acids having an aromatic-containing side chain (H, F, Y, W)

In one embodiment, the amino acid substitution may be performed with an amino acid present at a corresponding position in a natural human antibody.

In one embodiment, the amino acid substitution may be present outside the complementarity determining region (CDR).

In one embodiment, the amino acid substitution may be present in the heavy chain variable region or the light chain variable region.

Alternatively, the amino acid sequence of each CDR may include an amino acid sequence having 80% or more homology, preferably 80% or more identity to the sequence represented by the corresponding SEQ ID NO as long as it specifically binds to a 6-sulfosialyl Lewis X glycan, and the binding requires fucose, a sulfate group, and a sialic acid that form the 6-sulfosialyl Lewis X glycan. The sequence homology or identity is preferably 81%, 82%, 83%, 84%, 85%, 86%, 87%, 88%, 89%, 90%, 91%, 92%, 93%, 94%, 95%, 96%, 97%, 98%, or 99% or more, and more preferably 99% or more.

In one embodiment, the anti-glycan antibody may be an antibody or a fragment thereof that binds to an epitope bound by an antibody or a fragment thereof, which includes a variable region containing at least one or more CDRs selected from the group consisting of the following CDRs:

(a) CDRH1 including the amino acid sequence represented by SEQ ID NO: 1;
(b) CDRH2 including the amino acid sequence represented by SEQ ID NO: 2;
(c) CDRH3 including the amino acid sequence represented by SEQ ID NO: 3;
(d) CDRL1 including the amino acid sequence represented by SEQ ID NO: 4;
(e) CDRL2 including the amino acid sequence represented by SEQ ID NO: 5; and
(f) CDRL3 including the amino acid sequence represented by SEQ ID NO: 6, or includes at least one or more variable regions containing a CDR including an amino acid sequence having deletion, substitution, or addition of one or several amino acids in the amino acid sequence of the corresponding CDR, or includes at least one or more variable regions containing a CDR including an amino acid sequence having 80% or more identity to the amino acid sequence of the corresponding CDR.

As used herein, the "epitope" means a partial structure of a 6-sulfosialyl Lewis X glycan bound by an antibody or a fragment thereof, which specifically binds to a 6-sulfosialyl Lewis X glycan, where the binding requires fucose, a sulfate group, and a sialic acid that form the 6-sulfosialyl Lewis X glycan. When the epitope is a conformational epitope, the epitope can be identified by analyzing the structure of the 6-sulfosialyl Lewis X glycan bound to the antibody by X-ray crystallography or the like.

In one embodiment, the anti-glycan antibody may be an antibody or a fragment thereof, which includes a heavy chain variable region containing the following CDRs:

(a) CDRH1 including the amino acid sequence represented by SEQ ID NO: 1;
(b) CDRH2 including the amino acid sequence represented by SEQ ID NO: 2; and
(c) CDRH3 including the amino acid sequence represented by SEQ ID NO: 3, or includes a heavy chain variable region containing CDRH1, CDRH2, and CDRH3, each including an amino acid sequence having deletion, substitution, or addition of one or several amino acids in the amino acid sequence of the corresponding CDR, or includes a heavy chain variable region containing CDRH1, CDRH2, and CDRH3, each including an amino acid sequence having 80% or more identity to the amino acid sequence of the corresponding CDR.

In one embodiment, the heavy chain variable region in the anti-glycan antibody or the fragment thereof may contain at least 90 consecutive amino acids in the amino acid sequence represented by any of SEQ ID NOS: 13, and 15 to 17.

As used herein, the phrase "at least 90 consecutive amino acids in the amino acid sequence represented by any of SEQ ID NOS: 13, and 15 to 17" means 90, 91, 92, 93, 94, 95, 96, 97, 98, 99, 100, 101, 102, 103, 104, 105, 106, 107, 108, 109, 110, 111, 112, 113, 114, 115, 116, or 117 consecutive amino acids in the amino acid sequence represented by any of SEQ ID NOS: 13, and 15 to 17. Such consecutive amino acids preferably include CDRH1, CDRH2, and CDRH3 represented by amino acids at positions 26 to 33, amino acids at positions 51 to 57, and amino acids at positions 96 to 106 in order.

In one embodiment, the heavy chain variable region in the anti-glycan antibody or the fragment thereof may include the amino acid sequence represented by any of SEQ ID NOS: 15 to 17, an amino acid sequence having deletion, substitution, or addition of one or several amino acids in the amino acid sequence represented by any of SEQ ID NOS: 15 to 17, or an amino acid sequence having 80% or more identity to the amino acid sequence represented by any of SEQ ID NOS: 15 to 17.

In one embodiment, the heavy chain in the anti-glycan antibody or the fragment thereof may include the amino acid sequence represented by SEQ ID NO: 25, 27, or 28, an amino acid sequence having deletion, substitution, or addition of one or several amino acids in the amino acid sequence represented by SEQ ID NO: 25, 27, or 28, or an amino acid sequence having 80% or more identity to the amino acid sequence represented by SEQ ID NO: 25.

In one embodiment, the anti-glycan antibody may be an antibody or a fragment thereof, which includes a light chain variable region containing the following CDRs:

(d) CDRL1 including the amino acid sequence represented by SEQ ID NO: 4;
(e) CDRL2 including the amino acid sequence represented by SEQ ID NO: 5; and (f) CDRL3 including the amino acid sequence represented by SEQ ID NO: 6, or includes a light chain variable region containing CDRL1, CDRL2, and CDRL3, each including an amino acid sequence having deletion, substitution, or addition of one or several amino acids in the amino acid sequence of the corresponding CDR, or includes a light chain variable region containing CDRL1, CDRL2, and CDRL3, each including an amino acid sequence having 80% or more identity to the amino acid sequence of the corresponding CDR.

In one embodiment, the anti-glycan antibody may be an antibody or a fragment thereof, which includes a variable region containing the following CDRs:

(a) CDRH1 including the amino acid sequence represented by SEQ ID NO: 1;

(b) CDRH2 including the amino acid sequence represented by SEQ ID NO: 2;

(c) CDRH3 including the amino acid sequence represented by SEQ ID NO: 3;

(d) CDRL1 including the amino acid sequence represented by SEQ ID NO: 4;

(e) CDRL2 including the amino acid sequence represented by SEQ ID NO: 5; and (f) CDRL3 including the amino acid sequence represented by SEQ ID NO: 6, or includes a variable region containing CDRH1, CDRH2, and CDRH3 and CDRL1, CDRL2, and CDRL3, each including an amino acid sequence having deletion, substitution, or addition of one or several amino acids in the amino acid sequence of the corresponding CDR, or includes a variable region containing CDRH1, CDRH2, and CDRH3 and CDRL1, CDRL2, and CDRL3, each including an amino acid sequence having 80% or more identity to the amino acid sequence of the corresponding CDR.

In one embodiment, the light chain variable region in the anti-glycan antibody or the fragment thereof may contain at least 80 consecutive amino acids in the amino acid sequence represented by any of SEQ ID NOS: 14, and 18 to 20.

As used herein, the phrase "at least 80 consecutive amino acids in the amino acid sequence represented by any of SEQ ID NOS: 14, and 18 to 20" means 80, 81, 82, 83, 84, 85, 86, 87, 88, 89, 90, 91, 92, 93, 94, 95, 96, 97, 98, 99, 100, 101, 102, 103, 104, 105, or 106 consecutive amino acids in the amino acid sequence represented by any of SEQ ID NOS: 14, and 18 to 20. Such consecutive amino acids preferably include CDRL1, CDRL2, and CDRL3 represented by amino acids at positions 27 to 31, amino acids at positions 49 to 51, and amino acids at positions 88 to 96 in order.

In one embodiment, the light chain variable region in the anti-glycan antibody or the fragment thereof may include the amino acid sequence represented by any of SEQ ID NOS: 14, and 18 to 20, an amino acid sequence having deletion, substitution, or addition of one or several amino acids in the amino acid sequence represented by any of SEQ ID NOS: 14, and 18 to 20, or an amino acid sequence having 80% or more identity to the amino acid sequence represented by any of SEQ ID NOS: 14, and 18 to 20.

In one embodiment, the light chain in the anti-glycan antibody or the fragment thereof may include the amino acid sequence represented by SEQ ID NO: 26, an amino acid sequence having deletion, substitution, or addition of one or several amino acids in the amino acid sequence represented by SEQ ID NO: 26, or an amino acid sequence having 80% or more identity to the amino acid sequence represented by SEQ ID NO: 26.

As long as the anti-glycan antibody has the above-mentioned CDRs, other structures, for example, the structures of variable regions and constant regions other than CDRs are not particularly limited, but examples of the amino acid sequence encoding the heavy chain variable region containing CDRH1, CDRH2, and CDRH3 and the amino acid sequence encoding the light chain variable region containing CDRL1, CDRL2, and CDRL3 include the amino acid sequences of SEQ ID NOS: 13, 15, 16, and 17, and the amino acid sequences of SEQ ID NOS: 14, 18, 19, and 20, respectively.

In a preferred embodiment, the anti-glycan antibody or the fragment thereof may include a heavy chain variable region including the amino acid sequence of any of SEQ ID NOS: 13, 15, 16, or 17, and a light chain variable region including the amino acid sequence of any of SEQ ID NOS: 14, 18, 19, or 20.

In a preferred embodiment, a humanized anti-glycan antibody or a fragment thereof may include a heavy chain variable region including the amino acid sequence of any of SEQ ID NOS: 15, 16, or 17, and a light chain variable region including the amino acid sequence of any of SEQ ID NOS: 18, 19, or 20.

(Examples of combinations: SEQ ID NO: 15 and SEQ ID NO: 18, SEQ ID NO: 15 and SEQ ID NO: 19, SEQ ID NO: 15 and SEQ ID NO: 20, SEQ ID NO: 16 and SEQ ID NO: 18, SEQ ID NO: 16 and SEQ ID NO: 19, SEQ ID NO: 16 and SEQ ID NO: 20, SEQ ID NO: 17 and SEQ ID NO: 18, SEQ ID NO: 17 and SEQ ID NO: 19, and SEQ ID NO: 17 and SEQ ID NO: 20)

In a more preferred embodiment, the anti-glycan antibody or the fragment thereof may include any of the following combinations of a heavy chain variable region and a light chain variable region:

a heavy chain variable region including the amino acid sequence represented by SEQ ID NO: 13 and a light chain variable region including an amino acid sequence (SEQ ID NO: 4) represented by SEQ ID NO: 14 (SF1);

a heavy chain variable region (H1) including the amino acid sequence represented by SEQ ID NO: 15 and a light chain variable region (L1) including the amino acid sequence represented by SEQ ID NO: 18;

a heavy chain variable region (H1) including the amino acid sequence represented by SEQ ID NO: 15 and a light chain variable region (L2) including the amino acid sequence represented by SEQ ID NO: 19;

a heavy chain variable region (H2) including the amino acid sequence represented by SEQ ID NO: 16 and a light chain variable region (L1) including the amino acid sequence represented by SEQ ID NO: 18; and a heavy chain variable region (H3) including the amino acid sequence represented by SEQ ID NO: 17 and a light chain variable region (L3) including the amino acid sequence represented by SEQ ID NO: 20.

As used herein, "antibody" means a natural one or an artificial immunoglobulin or a fragment thereof produced by synthesis in whole or in part. The antibody can be of any isotype of IgG, IgM, IgA, IgE, and IgD. As human immunoglobulins, nine classes (isotypes) including IgG1, IgG2, IgG3, IgG4, IgA1, IgA2, IgD, IgE, and IgM are known.

The origin of the antibody does not matter, and may be any mammal, for example, a human, or a non-human animal such as a mouse, a rat, a guinea pig, a hamster, a rabbit, a goat, a sheep, or a camel. Not only a human antibody, but also a recombinant antibody such as a humanized antibody or a chimeric antibody can also be used. As used herein, "humanized antibody" is an antibody in which a CDR of a human antibody is replaced with a CDR derived from a non-human animal antibody. In addition to the CDR, some amino acid residues in the framework may be grafted into a human antibody. When a CDR derived from a non-human animal antibody is used for a human, it is preferably combined with a constant region of a human antibody. The antibody may be a polyclonal antibody or a monoclonal antibody, but is preferably a monoclonal antibody, particularly a mammal-derived monoclonal antibody.

The anti-glycan antibody may be subjected to chemical or biological modification as long as the desired effect is exhibited. A chemically modified variant includes a variant having an amino acid skeleton conjugated with a chemical moiety, a variant having a chemically modified N-linked or O-linked carbohydrate chain, and the like. A biologically modified variant may include a variant that has undergone post-translational modification (for example, N-linked or O-linked glycosylation, N-terminal or C-terminal processing, deamidation, isomerization of aspartic acid, or oxidation of methionine), a variant with a methionine residue added to the N-terminus by expression using a prokaryotic host cell, and the like.

Such a modified variant may further be a deletion variant in which one or two amino acids are deleted at the carboxyl terminus of the heavy chain, a variant obtained by amidating the deletion variant (for example, a heavy chain with an amidated proline residue in the carboxyl-terminal portion), or the like.

It is known that the amino acids Leu234-Leu235 of IgG1 according to the Eu numbering (Kabat Eu numbering) are a portion that affects the expression of effector activity through binding of the antibody to an Fc receptor and a complement. By substituting Leu contained in this region of IgG1 with Ala (the resulting variant is referred to as "IgG1-LALA variant"), the effector activity mediated by the Fc region of the antibody is reduced, so that the risk of side effects can sometimes be reduced (U.S. Patent Publication No. U.S. Pat. No. 5,885,573), and such a modification may be made to the Fc region of the antibody as needed. In addition to such a mutation, by substituting Pro329 with Gly (the resulting variant is referred to as "IgG1-P329G LALA variant"), the effector activity mediated by the Fc region of the antibody is reduced, so that the risk of side effects can sometimes be further reduced (U.S. Patent Publication No. U.S. Pat. No. 8,969,526, Protein Eng. Des Sel., 29:457-466, 2016), and such a modification may be made to the Fc region of the antibody as needed. Examples of the heavy chain of the IgG1-LALA variant include a heavy chain including the amino acid sequence represented by SEQ ID NO: 27.

It is known that substitution of Ser228 in IgG4 according to the Eu numbering with Pro inhibits separation of IgG4 into half antibodies. In addition, it is known that by substituting Leu235 in IgG4 with Glu, the expression of effector activity through binding of the antibody to an Fc receptor is reduced. By substituting Ser228 and Leu235 contained in this region of IgG4 with Pro and Glu, respectively (the resulting variant is referred to as "IgG4-SPLE variant"), the effector activity mediated by the Fc region of the antibody is reduced, so that the risk of side effects can sometimes be reduced (Newman et al., Clin. Immunol., 98:164-174, 2001), and such a modification may be made to the Fc region of the antibody as needed. Examples of the heavy chain of the IgG4-SPLE variant include a heavy chain including the amino acid sequence represented by SEQ ID NO: 28.

In another embodiment, another amino acid substitution or deletion (for example, according to the Eu numbering, substitution of Asp265 with Ala, deletion of Glu294, substitution of Asn297 with Ala, substitution of Lys322 with Ala, substitution of Ala330 with Leu, or substitution of Pro331 with Ser) known to reduce the expression of effector activity mediated by the Fc region of the antibody may be made to the Fc region of the antibody.

The two heavy chains that constitute the anti-glycan antibody may be formed of a combination of any one type of heavy chain selected from the group consisting of the full length and deletion variants described above, or a combination of any two types. The amount ratio of each deletion variant can be affected by the type of cultured mammalian cell that produces the anti-glycan antibody and the culture conditions, but as a main component of the anti-glycan antibody, a case where one amino acid residue at the carboxyl terminus is deleted in both two heavy chains can be exemplified.

As used herein, "fragment" of the antibody means a functional fragment that performs at least a part of the function performed by the antibody prior to fragmentation. Examples thereof include Fab, F(ab') 2, scFv, Fab', and a single-chain antibody (scFv). The fragment is not limited to these molecules, and may be any fragment as long as it specifically binds to a 6-sulfosialyl Lewis X glycan and the binding requires fucose, a sulfate group, and a sialic acid that form the 6-sulfosialyl Lewis X glycan. For example, the anti-glycan antibody may be an antibody that has a single heavy chain variable region but does not have a light chain sequence such as a single domain antibody or a nanobody.

Examples of a conceivable function of the anti-glycan antibody include recognition of a 6-sulfosialyl Lewis X glycan and inhibition of lymphocyte homing. The antibody or the fragment thereof may be a multispecific antibody having specificity for additional one or more antigens other than the 6-sulfosialyl Lewis X glycan. In addition to imparting multiple specificities, it is also possible to modify the anti-glycan antibody with an anticancer agent or the like, or impart multivalency to the anti-glycan antibody with the aim of improving the binding affinity according to the desired application.

The anti-glycan antibody may contain a linker such as a sequence obtained by repeating Gly-Gly-Gly-Gly-Ser (SEQ ID NO: 29) three times according to the intended purpose, and for example, when multiple variable regions that form an antigen binding site of an antibody are linked together as in the case of a single-chain antibody or the like, a linker may be interposed therebetween. For example, by linking a heavy chain variable region and a light chain variable region via a linker, a single-chain antibody is obtained. The sequence of the linker can be appropriately determined by those skilled in the art.

Examples of the single-chain antibody including an amino acid sequence encoding the heavy chain variable region containing CDRH1, CDRH2, and CDRH3 and the light chain variable region containing CDRL1, CDRL2, and CDRL3 include an antibody including an amino acid sequence at positions 1 to 117 and at positions 133 to 238 in the amino acid sequence represented by SEQ ID NO: 21, 22, 23, or 24. The single-chain antibody includes, for example, the amino acid sequence represented by SEQ ID NO: 21, 22, 23, or 24.

The fragment of the anti-glycan antibody can be obtained by treating the full-length molecule of the antibody protein with an enzyme such as papain or pepsin. Alternatively, it may be produced by expressing a gene encoding the desired fragment in a suitable host cell. When transforming the host cell, the heavy chain sequence gene and the light chain sequence gene can be inserted into the same expression vector, or can be inserted into separate expression vectors. The host cell may be either a prokaryotic cell or a eukaryotic cell. Examples of the prokaryotic cell include bacterial cells such as *E. coli* and *Bacillus subtilis*. When using a eukaryotic cell as the host, an animal cell, a plant cell, or a eukaryotic microorganism can be used. An animal cell, a plant cell, or a fungal cell can be used. Examples of the animal cell include the following cells.

(1) Mammalian cells: CHO, COS, myeloma, BHK (baby hamster kidney), Hela, Vero, HEK 293, Ba/F3, HL-60, Jurkat, SK-HEP1, etc.

(2) Amphibian cells: *Xenopus laevis* oocyte, etc.

(3) Insect cells: sf9, sf21, Tn5, etc.

In a preferred embodiment, the anti-glycan antibody may include any of the following combinations of a heavy chain and a light chain:

a heavy chain including the amino acid sequence represented by SEQ ID NO: 25 and a light chain including the amino acid sequence represented by SEQ ID NO: 26;

a heavy chain including the amino acid sequence represented by SEQ ID NO: 27 and a light chain including the amino acid sequence represented by SEQ ID NO: 26; and a heavy chain including the amino acid sequence represented by SEQ ID NO: 28 and a light chain including the amino acid sequence represented by SEQ ID NO: 26.

(Polynucleotide)

In a second embodiment, a polynucleotide encoding the anti-glycan antibody or the fragment thereof of the invention (polynucleotide of the invention) is provided.

The polynucleotide of the invention may be a single-stranded or double-stranded polynucleotide (DNA (such as cDNA), RNA (such as mRNA or cRNA)) including a nucleotide sequence encoding the amino acid sequence of the anti-glycan antibody or the fragment thereof and/or a complementary strand thereof.

The heavy chain variable region (or heavy chain) and the light chain variable region (or light chain) of the anti-glycan antibody or the fragment thereof may be encoded on the same polynucleotide, or may be encoded on separate polynucleotides and provided as a combination thereof. A combination of a polynucleotide encoding the heavy chain variable region (or heavy chain) and a polynucleotide encoding the light chain variable region (or light chain) is also included in the "polynucleotide encoding the anti-glycan antibody or the fragment thereof".

Examples of the polynucleotide encoding the anti-glycan antibody or the fragment thereof include a polynucleotide including at least one or more nucleotide sequences encoding a CDR selected from the group consisting of the following nucleotide sequences, preferably all six nucleotide sequences encoding a CDR:

(a) a nucleotide sequence that encodes CDRH1 including the amino acid sequence represented by SEQ ID NO: 1;

(b) a nucleotide sequence that encodes CDRH2 including the amino acid sequence represented by SEQ ID NO: 2;

(c) a nucleotide sequence that encodes CDRH3 including the amino acid sequence represented by SEQ ID NO: 3;

(d) a nucleotide sequence that encodes CDRL1 including the amino acid sequence represented by SEQ ID NO: 4;

(e) a nucleotide sequence that encodes CDRL2 including the amino acid sequence represented by SEQ ID NO: 5; and (f) a nucleotide sequence that encodes CDRL3 including the amino acid sequence represented by SEQ ID NO: 6.

Examples of the nucleotide sequences (a) to (f) are represented by SEQ ID NOS: 7 to 12 in order. The polynucleotide encoding the gene of the antibody or the fragment thereof may have a nucleotide sequence substantially identical to the nucleotide sequence represented by any of SEQ ID NOS: 7 to 12. The nucleotide sequence substantially identical to the nucleotide sequence represented by any of SEQ ID NOS: 7 to 12 is a polynucleotide including a sequence having 80% or more homology, preferably 80% or more identity, for example, 81%, 82%, 83%, 84%, 85%, 86%, 87%, 88%, 89%, 90%, 91%, 92%, 93%, 94%, 95%, 96%, 97%, 98%, or 99% or more, preferably 99% or more identity to the nucleotide sequence represented by any of SEQ ID NOS: 7 to 12, or alternatively, a polynucleotide that can hybridize with a polynucleotide including a sequence complementary to the nucleotide sequence represented by any of SEQ ID NOS: 7 to 12 under stringent conditions, and a protein encoded by the polynucleotide has a desired function, for example, specifically binds to a 6-sulfosialyl Lewis X glycan, where the binding requires fucose, a sulfate group, and a sialic acid that form the 6-sulfosialyl Lewis X glycan.

Here, the stringent conditions are hybridization conditions that are easily determined by those skilled in the art, and are generally empirical experimental conditions that depend on the nucleotide length of a nucleic acid, a washing temperature, and a salt concentration. In general, as the nucleotide becomes longer, the temperature for proper annealing becomes higher, and as the nucleotide becomes shorter, the temperature becomes lower. The formation of a hybrid generally depends on the ability of a complementary strand to reanneal in an environment slightly below the melting temperature thereof.

In one embodiment, the polynucleotide encoding the anti-glycan antibody or the fragment thereof may include the following nucleotide sequences:

(a) a nucleotide sequence that encodes CDRH1 including the amino acid sequence represented by SEQ ID NO: 1;

(b) a nucleotide sequence that encodes CDRH2 including the amino acid sequence represented by SEQ ID NO: 2; and (c) a nucleotide sequence that encodes CDRH3 including the amino acid sequence represented by SEQ ID NO: 3, or include nucleotide sequences that encode CDRH1, CDRH2, and CDRH3, and each include a nucleotide sequence having deletion, substitution, or addition of one or several nucleotides in the nucleotide sequence encoding the corresponding CDR, or include nucleotide sequences that encode CDRH1, CDRH2, and CDRH3, and each include a nucleotide sequence having 80% or more identity to the nucleotide sequence encoding the corresponding CDR.

In one embodiment, the polynucleotide encoding the anti-glycan antibody or the fragment thereof may include the following nucleotide sequences:

(d) a nucleotide sequence that encodes CDRL1 including the amino acid sequence represented by SEQ ID NO: 4;

(e) a nucleotide sequence that encodes CDRL2 including the amino acid sequence represented by SEQ ID NO: 5; and (f) a nucleotide sequence that encodes CDRL3 including the amino acid sequence represented by SEQ ID NO: 6, or include nucleotide sequences that encode CDRL1, CDRL2, and CDRL3, and each include a nucleotide sequence having deletion, substitution, or addition of one or several nucleotides in the nucleotide sequence encoding the corresponding CDR, or include nucleotide sequences that encode CDRL1, CDRL2, and CDRL3, and each include a nucleotide sequence having 80% or more identity to the nucleotide sequence encoding the corresponding CDR.

In one embodiment, the polynucleotide encoding the anti-glycan antibody or the fragment thereof may include the following nucleotide sequences:

(a) a nucleotide sequence that encodes CDRH1 including the amino acid sequence represented by SEQ ID NO: 1;

(b) a nucleotide sequence that encodes CDRH2 including the amino acid sequence represented by SEQ ID NO: 2;

(c) a nucleotide sequence that encodes CDRH3 including the amino acid sequence represented by SEQ ID NO: 3;

(d) a nucleotide sequence that encodes CDRL1 including the amino acid sequence represented by SEQ ID NO: 4;

(e) a nucleotide sequence that encodes CDRL2 including the amino acid sequence represented by SEQ ID NO: 5; and (f) a nucleotide sequence that encodes CDRL3 including the amino acid sequence represented by SEQ ID NO: 6, or include nucleotide sequences that encode CDRH1, CDRH2, and CDRH3 and CDRL1, CDRL2, and CDRL3, and each include a nucleotide sequence having deletion, substitution, or addition of one or several nucleotides in the nucleotide sequence encoding the corresponding CDR, or include nucleotide sequences that encode CDRH1, CDRH2, and CDRH3 and CDRL1, CDRL2, and CDRL3, and each include a nucleotide sequence having 80% or more identity to the nucleotide sequence encoding the corresponding CDR.

(Vector and Host Cell)

In a third embodiment, an expression vector containing the polynucleotide encoding the anti-glycan antibody or the fragment thereof, and a host cell transfected with the expression vector are provided. The host cell transfected with the expression vector can produce the anti-glycan antibody or the fragment thereof.

The polynucleotide encoding the heavy chain variable region (or heavy chain) of the anti-glycan antibody or the fragment thereof, and the polynucleotide encoding the light chain variable region (or light chain) of the anti-glycan antibody or the fragment thereof may be incorporated into the same expression vector, or may be incorporated into separate expression vectors and provided as a combination thereof. A combination of an expression vector containing the polynucleotide encoding the heavy chain variable region (or heavy chain) (the expression vector for the heavy chain variable region (or heavy chain)) and an expression vector containing the polynucleotide encoding the light chain variable region (or light chain) (the expression vector for the light chain variable region (or light chain)) is also included in the "expression vector containing the polynucleotide encoding the anti-glycan antibody or the fragment thereof".

The expression vector containing the polynucleotide encoding the anti-glycan antibody or the fragment thereof and the host cell transfected with the expression vector can be obtained by a method known to those skilled in the art. For example, a polynucleotide or the like encoding a single-chain anti-glycan antibody is incorporated into a vector suitable for the expression thereof, and the vector is introduced into a host, thereby expressing the anti-glycan antibody or the fragment thereof. The expression vector preferably contains a promoter, a terminator, etc. suitable for the expression of the anti-glycan antibody or the fragment thereof in the host cell. The expression vector can further contain another appropriate control sequence such as an enhancer.

The vector can be appropriately selected from expression vectors well known to those skilled in the art in consideration of the type of host cell, the expression efficiency of the anti-glycan antibody or the fragment thereof, and the like, and the type may be a plasmid vector or a viral vector derived from a retrovirus or an adenovirus.

The host cell is not limited as long as it can express the anti-glycan antibody or the fragment thereof from the expression vector, and may be a prokaryotic cell such as *E. coli*, or a mammal-derived cell such as CHO, COS, NIH3T3, HEK 293, HEK 293T, or COS-7, an insect-derived cell such as F9, or a eukaryotic cell such as a yeast cell. Examples of the mammal include primates such as a human and a chimpanzee, and rodents such as a mouse, a rat, and a hamster.

The transfection of the expression vector into the host cell can be carried out using, for example, a method well known to those skilled in the art such as an electroporation method, a calcium phosphate method, a lipofection method, or a DEAE dextran method, or a method using a commercially available reagent.

The host cell (transfectant) transfected with the expression vector containing the polynucleotide encoding the anti-glycan antibody or the fragment thereof include a transfectant that contains the expression vector and expresses the anti-glycan antibody or the fragment thereof; and a transfectant (stable transfectant) that expresses the anti-glycan antibody or the fragment thereof by incorporating the polynucleotide encoding the anti-glycan antibody or the fragment thereof into the chromosome of the host cell in an expressible manner.

The stable transfectant may or may not contain the expression vector containing the polynucleotide encoding the anti-glycan antibody or the fragment thereof. The transfectant is preferably a mammal-derived cell such as CHO, COS, NIH3T3, HEK 293, HEK 293T, or COS-7.

(Hybridoma)

In a fourth embodiment, a hybridoma that produces the anti-glycan antibody is provided.

The hybridoma that produces the anti-glycan antibody can be obtained by immunizing an immune animal through injection of a glycoprotein with a 6-sulfosialyl Lewis X glycan added thereto, or administration of a vector that encodes a 6-sulfosialyl Lewis X glycan and is designed so as to be able to express the 6-sulfosialyl Lewis X glycan in the immune animal and fusing an immune cell obtained from the immune animal with a known myeloma cell through a conventional cell fusion method. A cell that produces the anti-glycan antibody is screened from such hybridomas. Examples of the immune animal include rodents such as a mouse, a rat, a hamster, and a rabbit, and mammals such as a monkey.

In one embodiment, the hybridoma that produces the anti-glycan antibody is obtained by preparing spleen cells from a mouse obtained by immunizing a mouse deficient in sulfotransferases, GlcNAc6ST-1 and GlcNAc6ST-2, that are responsible for sulfation of 6-sulfosialyl Lewis X expressed in HEV with a cell made to express a 6-sulfosialyl Lewis X glycan by introducing genes of a fucosyltransferase and a sulfotransferase, and selecting a hybridoma that secretes an IgG class antibody specifically exhibiting binding affinity for wild-type mouse HEV from multiple hybridomas obtained by cell fusion of the spleen cells with myelomas through immunofluorescent staining of mouse peripheral lymph nodes using the culture supernatants of the hybridomas.

(Method for Producing Anti-Glycan Antibody)

In a fifth embodiment, a method for producing the anti-glycan antibody or the fragment thereof is provided. The production of the anti-glycan antibody or the fragment thereof may be performed by culturing the above-mentioned host cell, transfectant, or hybridoma, or may be performed using recombinant DNA technology.

Examples of the antibody produced as a recombinant protein by recombinant DNA technology include a chimeric antibody, a humanized antibody, and a human antibody. Such an antibody can be produced, for example, by culturing a host cell transformed with a recombinant vector encoding the antibody or its heavy chain or light chain. The recombinant antibody can also be produced using a transgenic animal obtained by introducing a gene encoding a desired antibody.

The culture conditions for the host cell, the transfectant, or the hybridoma can be appropriately determined by those skilled in the art according to the desired anti-glycan antibody or the fragment thereof or the type of host cell. The production method may further include a step of recovering the antibody or the fragment thereof, which specifically binds to a 6-sulfosialyl Lewis X glycan, where the binding requires fucose, a sulfate group, and a sialic acid that form the 6-sulfosialyl Lewis X glycan, from the culture obtained in the culturing step.

The produced antibody or the fragment thereof may be further subjected to an additional step such as a purification step prior to recovery, and for example, in order to increase the purity, it is preferred to perform salting out, filter filtration, clarification using centrifugation, recovery by affinity chromatography, intermediate purification by ion exchange, and final purification by gel filtration.

(Lymphocyte Homing Inhibitor)

In a sixth embodiment, a lymphocyte homing inhibitor containing the anti-glycan antibody or the fragment thereof is provided.

The lymphocyte homing is a biological defense mechanism provided for efficiently inducing an immune response, and lymphocyte homing to lymph nodes is controlled by the following three steps, that is, step 1: lymphocyte rolling via binding of L-selectin expressed on a lymphocyte to a sulfated glycan 6-sulfosialyl Lewis X expressed in the HEV lumen, step 2: activation of an adhesion molecule integrin by signal transduction via binding of a chemokine presented on heparan sulfate in the HEV lumen to a chemokine receptor, and step 3: strong adhesion between activated integrin and immunoglobulin superfamily adhesion molecules ICAM-1 (intercellular adhesion molecule-1) and VCAM-1 (vascular cell adhesion molecule-1) and infiltration into a lymphoid tissue, and through these three steps, a lymphocyte migrates into the lymphoid tissue parenchyma.

Among these, in the step 1, the sulfated glycan 6-sulfosialyl Lewis X expressed in the HEV lumen is responsible for an important function, and in the step 2, heparan sulfate is responsible for an important function. Therefore, a lymphocyte homing inhibitor is prepared by using, as an active ingredient, an antibody or a fragment thereof that specifically binds to fucose, a sulfate group, and a sialic acid that form a 6-sulfosialyl Lewis X glycan. The lymphocyte homing inhibitor particularly inhibits lymphocyte homing from a lymph node expressing a 6-sulfosialyl Lewis X glycan, for example, a peripheral lymph node, a mesenteric lymph node, or a high endothelial venule in a tonsil, more specifically, preferably inhibits L-selectin-dependent lymphocyte rolling.

(Pharmaceutical Composition)

In a seventh embodiment, pharmaceutical use of the anti-glycan antibody or the fragment thereof, for example, a pharmaceutical composition containing the anti-glycan antibody or the fragment thereof is provided.

As the pharmaceutical use of the anti-glycan antibody or the fragment thereof, treatment or prevention of a disease caused by an overactive immune response mediated by lymphocyte homing is exemplified. Specifically, a preventive effect on a disease by administration of the anti-glycan antibody or the fragment thereof before onset of the disease, a therapeutic effect on a disease by administration after onset of the disease, and a relapse prevention effect on a chronic disease that repeats relapse and remission are exemplified. Among the excessive immune responses mediated by lymphocyte homing, as a tissue where an immune response occurs and the administration of the anti-glycan antibody is considered to be particularly effective, a peripheral lymph node, a mesenteric lymph node, and a tonsil are exemplified. Examples of the disease caused by an overactive immune response beyond normal levels mediated by lymphocyte homing, particularly specific adhesion of a lymphocyte to HEV include an immune-related disease such as an autoimmune disease. The immune-related disease is, for example, an autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenia purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; nonarticular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; psoriasis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

The autoimmune disease may be multiple sclerosis or a collagen disease. The collagen disease may be, for example, rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, SAPHO syndrome, or the like. The autoimmune disease may be one or multiple diseases selected from the group consisting of other diseases in which an excessive immune response damages the self other than the above diseases.

Examples of the other diseases caused by an overactive immune response mediated by lymphocyte homing include an immune-related disease such as an allergic disease. The immune-related disease may be one or multiple diseases selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

The pharmaceutical composition may further contain an additional component, for example, a pharmaceutically acceptable diluent, a carrier, a solubilizer, an emulsifier, a preservative, an adjuvant, or the like according to the route of administration, an applicable disease, or the like in addition to the anti-glycan antibody or the fragment thereof as an active ingredient. The dose of the anti-glycan antibody can be appropriately determined according to the type of disease, the age, sex, and body weight of the patient, the degree of the disease and the treatment, or the like. The pharmaceutical composition may further contain an agent which is known to have a therapeutic or preventive effect on a disease caused by an overactive immune response mediated by lymphocyte homing other than the anti-glycan antibody.

The dosage form of the pharmaceutical composition includes a liquid, a lyophilized preparation, and the like, and examples of the administration route of the pharmaceutical composition include, but are not limited to, intravenous infusion, subcutaneous injection, and intramuscular injection.

In another embodiment, a method for treating or preventing a disease caused by an overactive immune response mediated by lymphocyte homing, particularly specific adhesion of a lymphocyte to HEV, including a step of administering the anti-glycan antibody or the fragment thereof to a subject who needs treatment or prevention is provided. The anti-glycan antibody or the fragment thereof may be used in combination with another agent which is known to have a therapeutic or preventive effect on a disease caused by an overactive immune response mediated by lymphocyte homing.

Hereinafter, the invention will be more specifically described with reference to Examples, but the invention is not limited thereto.

EXAMPLES

1. Production of Anti-Glycan Antibody

A monoclonal antibody against a 6-sulfosialyl Lewis X glycan was produced. First, by introducing genes encoding a fucosyltransferase FucT-VII and a sulfotransferase GlcNAc6ST-2, a Chinese hamster ovary (CHO) cell was made to express a 6-sulfosialyl Lewis X glycan. By using this CHO cell, a sulfotransferase double-deficient mouse deficient in sulfotransferases GlcNAc6ST-1 and GlcNAc6ST-2 (Kawashima et al. (mentioned above)) was immunized. The spleen cells were fused with P3X63Ag8.653 myeloma cells using polyethylene glycol, and a hybridoma that produces an anti-sulfated glycan monoclonal antibody SF1 (mouse IgG1, kappa) having reactivity with a high endothelial venule (HEV) of a wild-type (WT) mouse was established by screening with immunohistological staining. The obtained antibody has reactivity with a sulfated and fucosylated glycan as described later, and therefore was named SF1 antibody (S means that the clone recognizes sulfate group, and F means that the clone recognizes fucose.).

2. Analysis of Reactivity of SF1 Antibody with HEV

Figure 2:
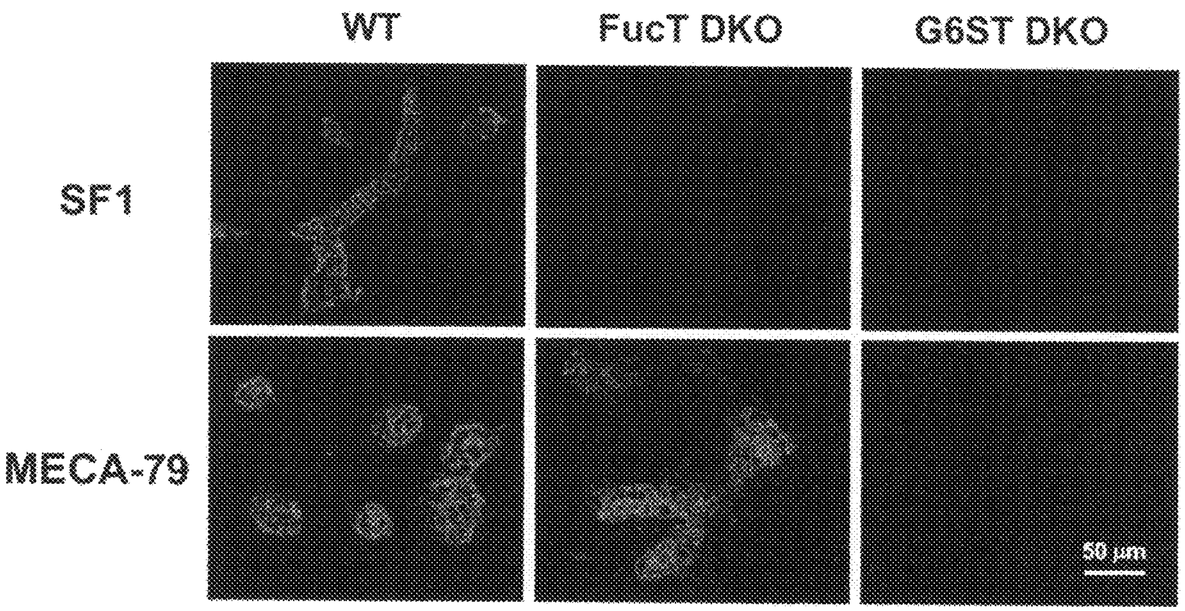
FIG. 2 shows immunostaining results obtained by analyzing the reactivity of SF1 antibody and MECA-79 antibody with a mouse lymph node high endothelial venule (HEV) by fluorescent immunostaining.

The SF1 antibody was purified and biotin-labeled according to a usual method, and lymph node frozen sections of a WT mouse, a fucosyltransferase (FucT)-IV and FucT-VII gene double-deficient mouse (FucT DKO), a sulfotransferase (GlcNAc6ST)-1 and GlcNAc6ST-2 double-deficient mouse (G6ST DKO) were incubated overnight at 4° C. After the sections were washed with PBS, fluorescent immunostaining was performed by further incubating AlexaFluor 594-labeled streptavidin, which is a fluorescent substance, at room temperature for 1 hour (FIG. 2).

As a result, the SF1 antibody strongly reacted with the lymph node HEV of the WT mouse, but did not react at all with the HEV of FucT DKO and G6ST DKO. This indicates that both fucose and a sulfate group are involved in the reaction of the SF1 antibody with the mouse lymph node. On the other hand, MECA-79 (Streeter et al. (mentioned above)), which is a known antibody, reacted with mouse lymph node HEV, but the reactivity did not disappear in FucT DKO, and therefore, fucose, which plays an important role in lymphocyte homing, is not involved in the reactivity.

Figure 3:
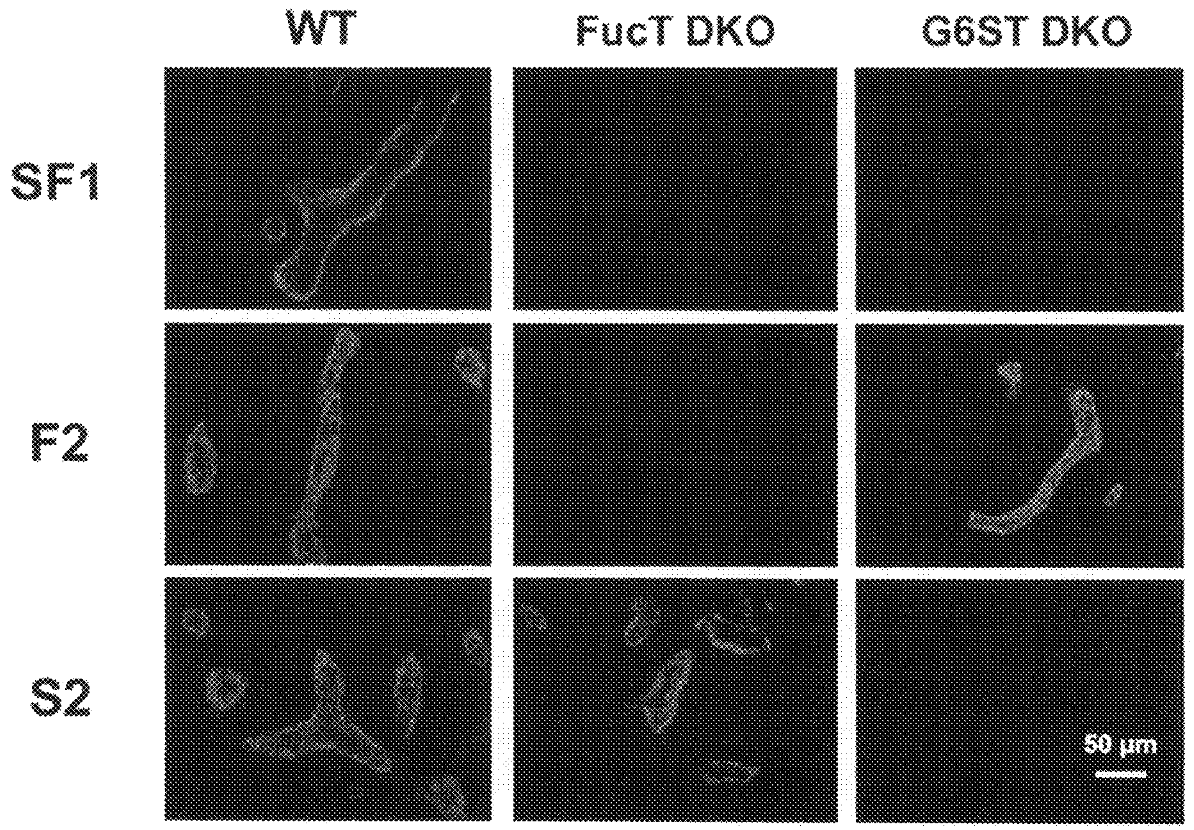
FIG. 3 shows immunostaining results obtained by analyzing the reactivity of SF1 antibody, F2 antibody, and S2 antibody with a mouse lymph node high endothelial venule (HEV) by fluorescent immunostaining.

In addition, fluorescent immunostaining was performed using antibodies that recognize other glycans on HEV. In the same manner as described above, the SF1 antibody strongly reacted with the lymph node HEV of the WT mouse, but did not react at all with the HEV of FucT DKO and G6ST DKO. On the other hand, an F2 antibody (Matsumura et al. (mentioned above)), which is a known antibody, reacted with the lymph node HEV of the WT mouse and did not react with FucT DKO, but the reactivity did not disappear in G6ST DKO, and therefore, a sulfate group, which plays an important role in lymphocyte homing, is not involved in the reactivity. In contrast, an S2 antibody (Hirakawa et al. (mentioned above)), which is a known antibody, reacted with the lymph node HEV of the WT mouse and did not react with G6ST DKO, but the reactivity did not disappear in FucT DKO, and therefore, fucose, which plays an important role in lymphocyte homing, is not involved in the reactivity. The results are shown in FIG. 3.

Figure 4:
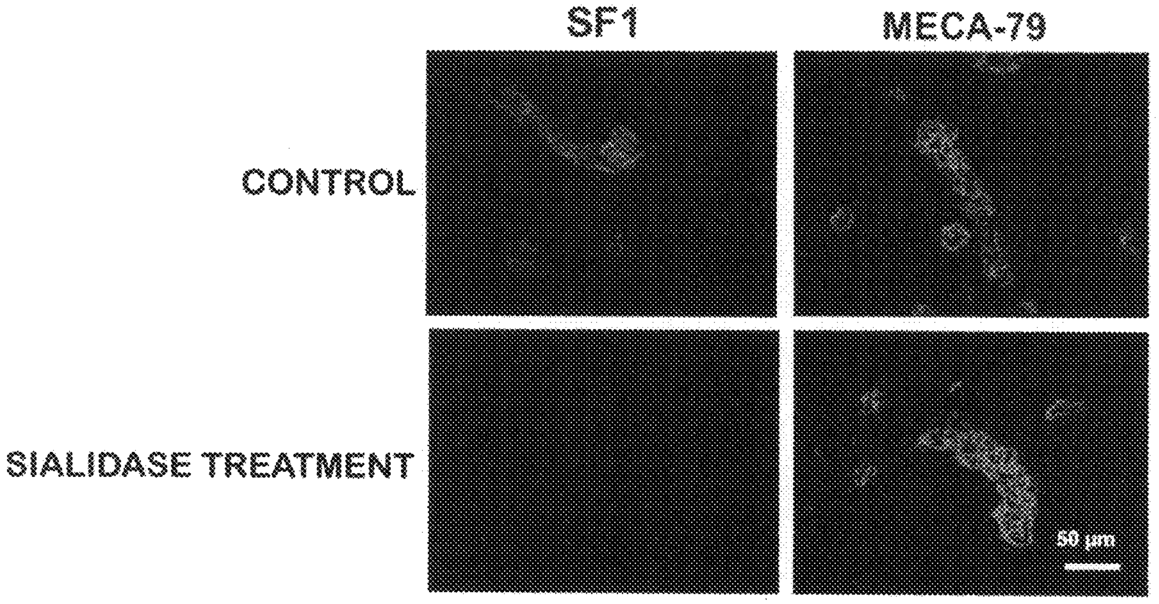
FIG. 4 shows immunostaining results obtained by analyzing the effect of a sialidase treatment on the reactivity of SF1 antibody with mouse lymph node HEV.

Subsequently, the involvement of a sialic acid in the reactivity with HEV was studied by treating a lymph node frozen section of a WT mouse with sialidase. The results are shown in FIG. 4.

By the treatment with sialidase, the reactivity of the SF1 antibody disappeared, and therefore, it is found that a sialic acid, which plays an important role in lymphocyte homing, is also involved in the reactivity of the SF1 antibody with mouse lymph nodes, in addition to fucose and a sulfate group. On the other hand, a sialic acid is not involved in the reactivity of the known anti-glycan monoclonal antibody MECA-79. From the above results of immunofluorescent staining, it is found that the SF1 antibody obtained in this study is an anti-glycan monoclonal antibody that specifically recognizes a glycan structure containing fucose, a sulfate group, and a sialic acid on mouse lymph node HEV.

3. Analysis of Reactivity of SF1 Antibody with Synthetic Glycans

Figure 5:
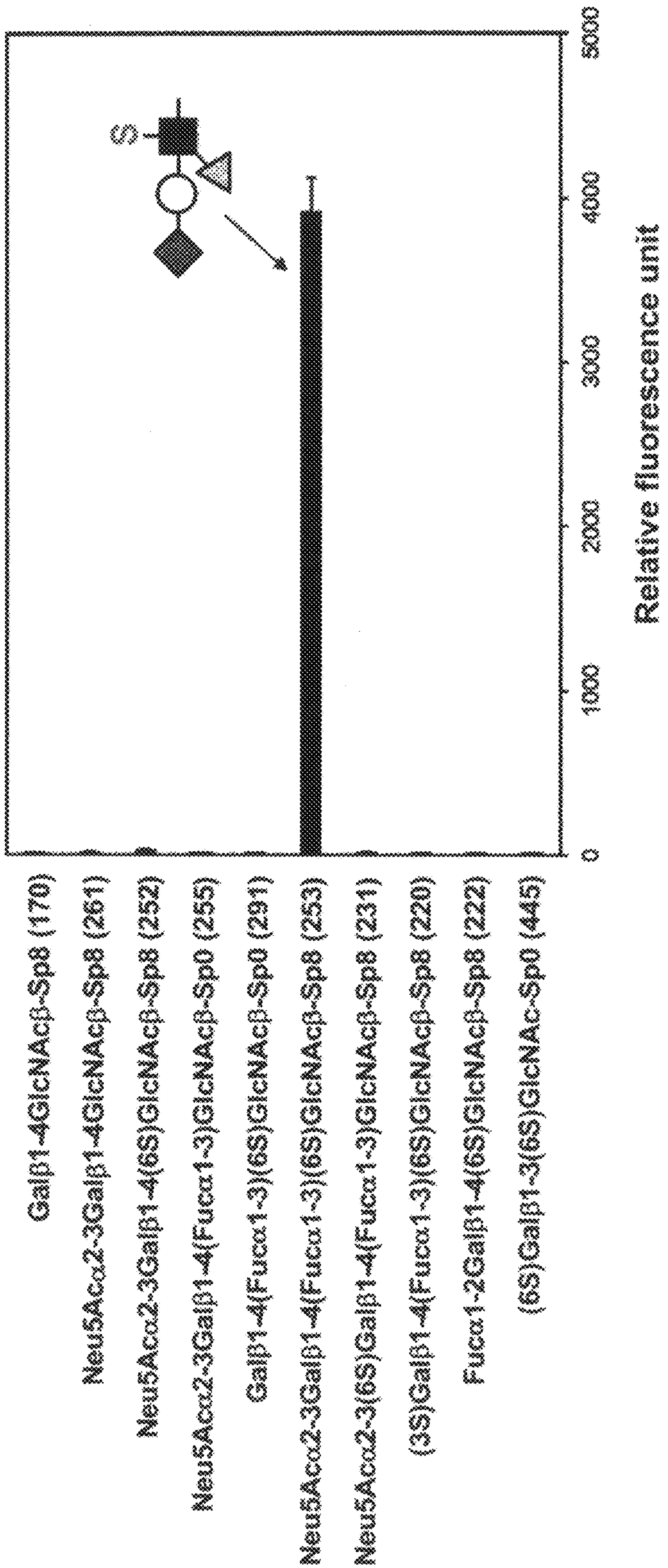
FIG. 5 shows results obtained by analyzing the reactivity of SF1 antibody with various types of glycans with a glycan array.

Next, the reactivity of the SF1 antibody with various types of glycans was analyzed using the Glycan Array of the US Consortium for Functional Glycomics. As a result, the SF1 antibody specifically bound only to a 6-sulfosialyl Lewis X glycan among 611 types of glycans on the Glycan Array. FIG. 5 shows an excerpt of the results of the 6-sulfosialyl Lewis X glycan and nine types of glycans having a partially similar structure to the 6-sulfosialyl Lewis X glycan present on the Glycan Array. The number in parentheses in the drawing indicates the ID number of each glycan in the Glycan Array. From FIG. 5, it can be seen that the SF1 antibody does not bind at all to LacNAc (ID No. 170) or sialyl LacNAc (ID No. 261). In addition, it can be seen that the SF1 antibody does not bind to any of 6-sulfosialyl LacNAc (ID No. 252) in which fucose is removed from the 6-sulfosialyl Lewis X glycan, sialyl Lewis X (ID No. 255) in which a sulfate group is removed from the 6-sulfosialyl Lewis X glycan, and 6-sulfo Lewis X (ID No. 291) in which a sialic acid is removed from the 6-sulfosialyl Lewis X glycan, but specifically binds to 6-sulfosialyl Lewis X (ID No. 253). Further, the SF1 antibody did not bind to any of 6'-sulfosialyl Lewis X (ID No. 231) in which a sulfate group is added to galactose instead of GlcNAc, a glycan (ID No. 220) in which a sulfate group is added to the 3-position of galactose in place of the terminal $\alpha$2-3-linked sialic acid (Neu5Ac) of 6-sulfosialyl Lewis X, a glycan (ID No. 222) in which fucose is added to galactose via an $\alpha$1-2 linkage in place of $\alpha$2-3 linked Neu5Ac, and 6,6'-disulfo LacNAc (ID No. 445) sulfated at both the 6-position of galactose and the 6-position of GlcNAc. From the above, it was found that the SF1 antibody specifically binds to the 6-sulfosialyl Lewis X glycan.

Figure 6:
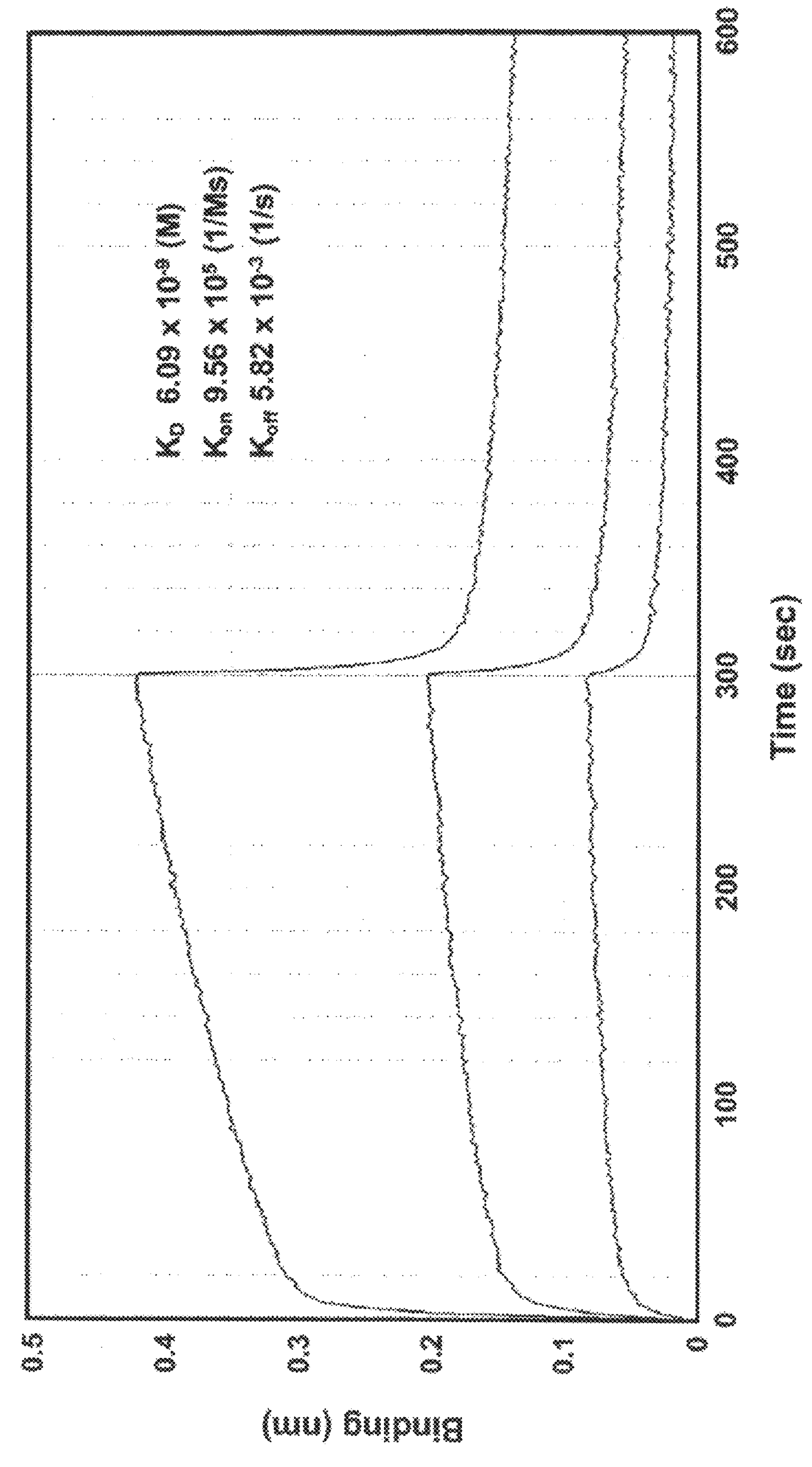
FIG. 6 shows results obtained by measuring the dissociation constant for the binding of SF1 antibody to 6-sulfosialyl Lewis X by biolayer interferometry.

4. Determination of Dissociation Constant for Binding of SF1 Antibody to 6-Sulfosialyl Lewis X Next, the dissociation constant ($K_D$) for binding of the SF1 antibody to 6-sulfosialyl Lewis X was measured by biolayer interferometry using Octet RED96 (manufactured by Pall-Fortebio LLC). After binding biotin-labeled 6-sulfosialyl Lewis X to a streptavidin biosensor, binding and dissociation of the SF1 antibody were analyzed in real time. The results are shown in FIG. 6.

As a result, it was found that the $K_D$ value for binding of the SF1 antibody to 6-sulfosialyl Lewis X is $6.09\times10^{-9}$ (M). When biotin-labeled sialyl LacNAc was used as a negative control, no binding was observed.

5. Determination of Amino Acid Sequence of Anti-Glycan Antibody

Next, the antibody gene was obtained from the hybridoma that produces the SF1 antibody, the nucleotide sequence thereof was analyzed, and the amino acid sequences of the hypervariable regions of the heavy chain and light chain variable regions of the SF1 antibody were determined. CDR1, CDR2 and CDR3 of the heavy chain of the SF1 antibody are represented by SEQ ID NO: 1 (CDRH1), SEQ ID NO: 2 (CDRH2), and SEQ ID NO: 3 (CDRH3), respectively, and CDR1, CDR2 and CDR3 of the light chain of the SF1 antibody are represented by SEQ ID NO: 4 (CDRL1), SEQ ID NO: 5 (CDRL2), and SEQ ID NO: 6 (CDRL3), respectively, and shown in FIG. 7. Since no antibody with such hypervariable regions has been reported so far, it is found to be an antibody having a novel sequence.

The full amino acid sequence of the heavy chain variable region of the SF1 antibody is represented by SEQ ID NO: 13 and shown in FIG. 8. The sequences of CDRH1, CDRH2, and CDRH3 are shown in bold.

The full amino acid sequence of the light chain variable region of the SF1 antibody is represented by SEQ ID NO: 14 and shown in FIG. 9. The sequences of CDRL1, CDRL2, and CDRL3 are shown in bold.

Figure 10:
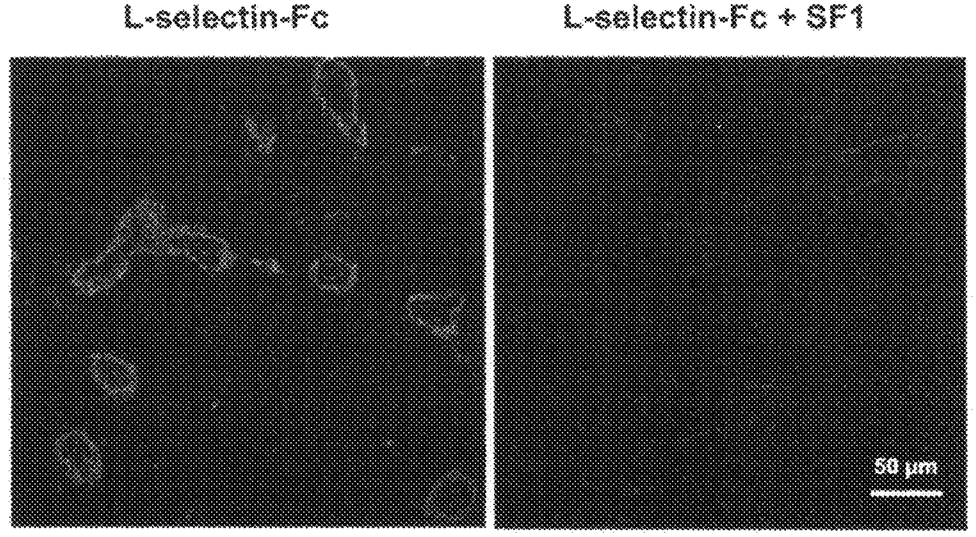
FIG. 10 shows the inhibitory effect of SF1 antibody on the binding of L-selectin-Fc to mouse lymph node HEV.

6. Analysis of Inhibitory Effect of SF1 Antibody on Binding of L-Selectin to HEV A mouse lymph node frozen section was incubated at room temperature for 2 hours together with a buffer A (0.1% BSA, 20 mM HEPES-NaOH, 0.15 M NaCl, 1 mM $CaCl_2$), 1 mM $MgCl_2$, pH 7.4) alone or together with the SF1 antibody dissolved in the buffer A at room temperature for 2 hours, and thereafter incubated overnight at 4° C. together with a fusion protein of L-selectin and human IgG (L-selectin-Fc) dissolved in the buffer A. Then, the section was washed with the buffer A, and thereafter incubated at room temperature for 2 hours together with a biotin-labeled anti-human IgG antibody. The section was washed with the buffer A, and thereafter, fluorescent immunostaining was performed by further incubating AlexaFluor 594-labeled streptavidin, which is a fluorescent substance, at room temperature for 1 hour (FIG. 10).

As a result, the SF1 antibody strongly inhibited the binding of L-selectin-Fc to HEV. This indicates that the SF1 antibody inhibits the interaction between the L-selectin, which is a lymphocyte homing receptor, and a ligand expressed on HEV.

Figure 11:
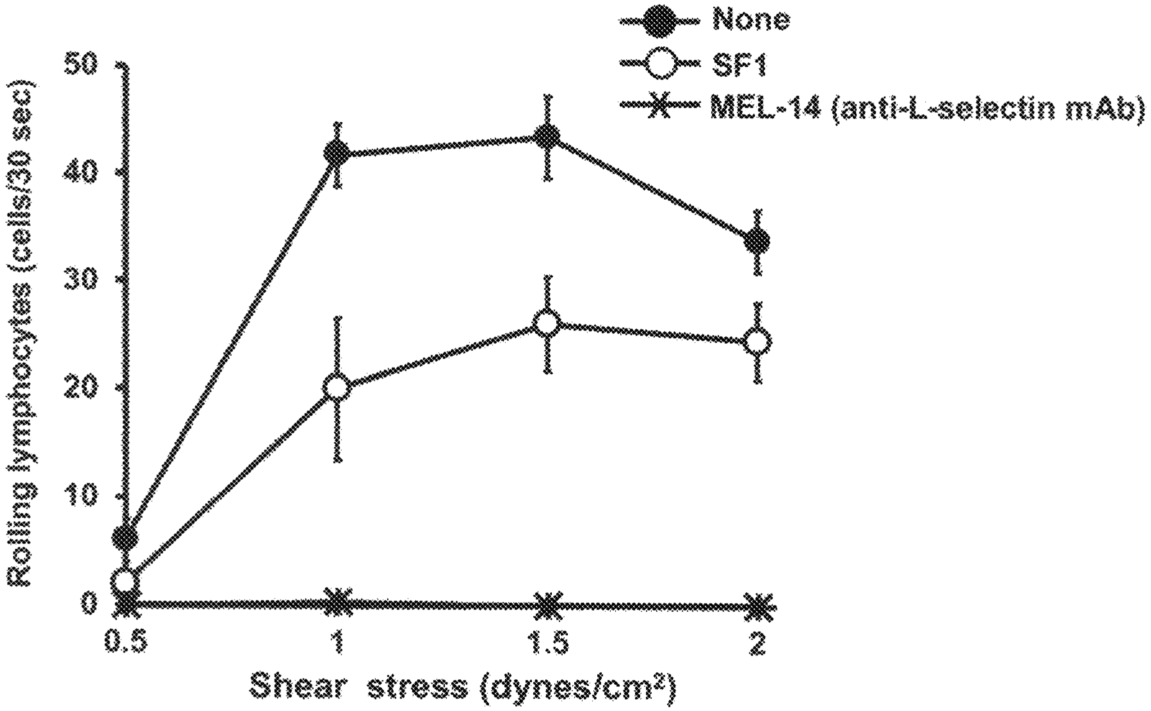
FIG. 11 shows the inhibitory effect of SF1 antibody on L-selectin-dependent lymphocyte rolling.

7. Analysis of Inhibitory Effect of SF1 Antibody on L-Selectin-Dependent Lymphocyte Rolling CHO cells, which stably express a core protein CD34 and a 6-sulfosialyl Lewis X glycan, and in which a ligand for L-selectin expressed on HEV was reconstituted, were cultured in a plate, and the plate was placed in a flow chamber. Subsequently, lymphocytes prepared from the mouse spleen were allowed to flow under various shear stress levels (0.5, 1.0, 1.5, and 2.0 dynes/$cm^2$), and the number of rolling cells on cells in which the ligand for L-selectin was reconstituted was measured. At that time, the measurement was performed by dividing the cells into three groups: an untreated group (None in the drawing), a group in which the cells in which the ligand for L-selectin was reconstituted were previously incubated with the SF1 antibody (SF1 in the drawing), and a group in which the lymphocytes were previously incubated with the anti-L-selectin antibody (MEL-14 in the drawing). The results are shown in FIG. 11.

As a result, since the observed rolling was inhibited by the anti-L-selectin antibody, it was confirmed that the rolling is dependent on L-selectin, and it was found that the SF1 antibody has an effect of suppressing L-selectin-dependent rolling.

8. Analysis of Inhibitory Effect of SF1 Antibody on Lymphocyte Homing

Figure 12:
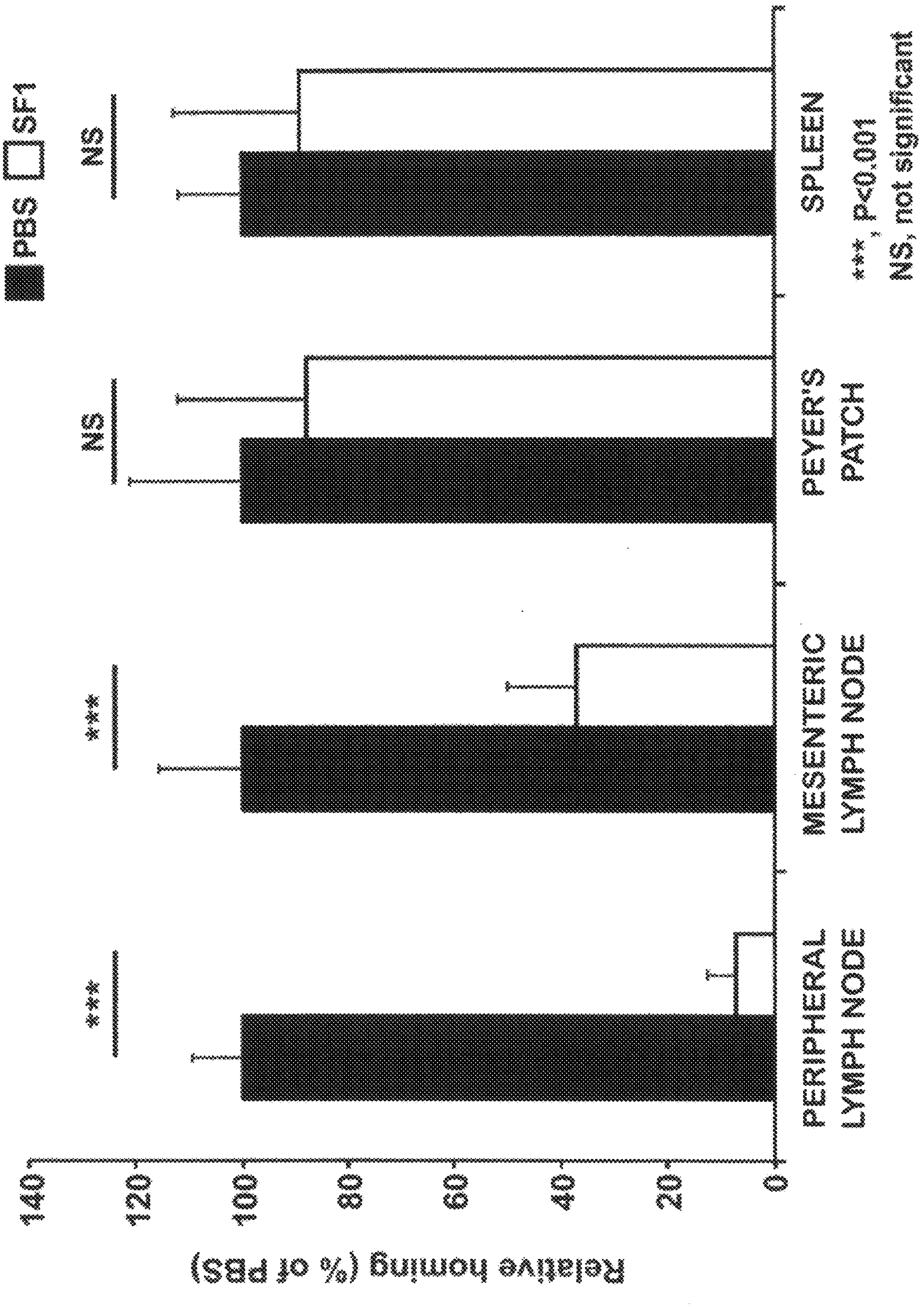
FIG. 12 shows results obtained by analyzing the inhibitory effect of SF1 antibody on lymphocyte homing.

A WT mouse was intravenously injected with the SF1 antibody or PBS through the tail vein, and then intravenously injected with lymphocytes (derived from mesenteric lymph nodes and spleen) labeled with a fluorescent substance CFSE through the tail vein. After 2 hours, each lymph tissue was collected, and the number of CFSE-labeled lymphocytes infiltrating (homing) into each tissue was examined (FIG. 12).

As a result, it was found that the SF1 antibody is an antibody having activity of suppressing lymphocyte homing to mouse peripheral lymph nodes by 90% or more. In addition, the SF1 antibody suppressed homing to mesenteric lymph nodes by about 60%. On the other hand, it was found that the SF1 antibody is an antibody with high specificity such that it does not exhibit a significant inhibitory effect on homing to a Peyer's patch, which expresses a glycan recognized by the SF1 antibody only in 5% or less of HEV, and the spleen, which does not express such a glycan at all. In the Peyer's patch, an intestinal immune response occurs against a microorganism in the intestinal tract and a food-derived antigen, and in the spleen, an immune response occurs against a foreign substance that has invaded into the blood, and therefore, it was expected that the SF1 antibody is useful for treating or preventing an immune-related disease caused by an excessive immune response in peripheral lymph nodes and mesenteric lymph nodes without causing a side effect caused by suppressing such normal immune responses in the Peyer's patch and the spleen.

9. Analysis of Effect of SF1 Antibody in EAE Model

Figure 13:
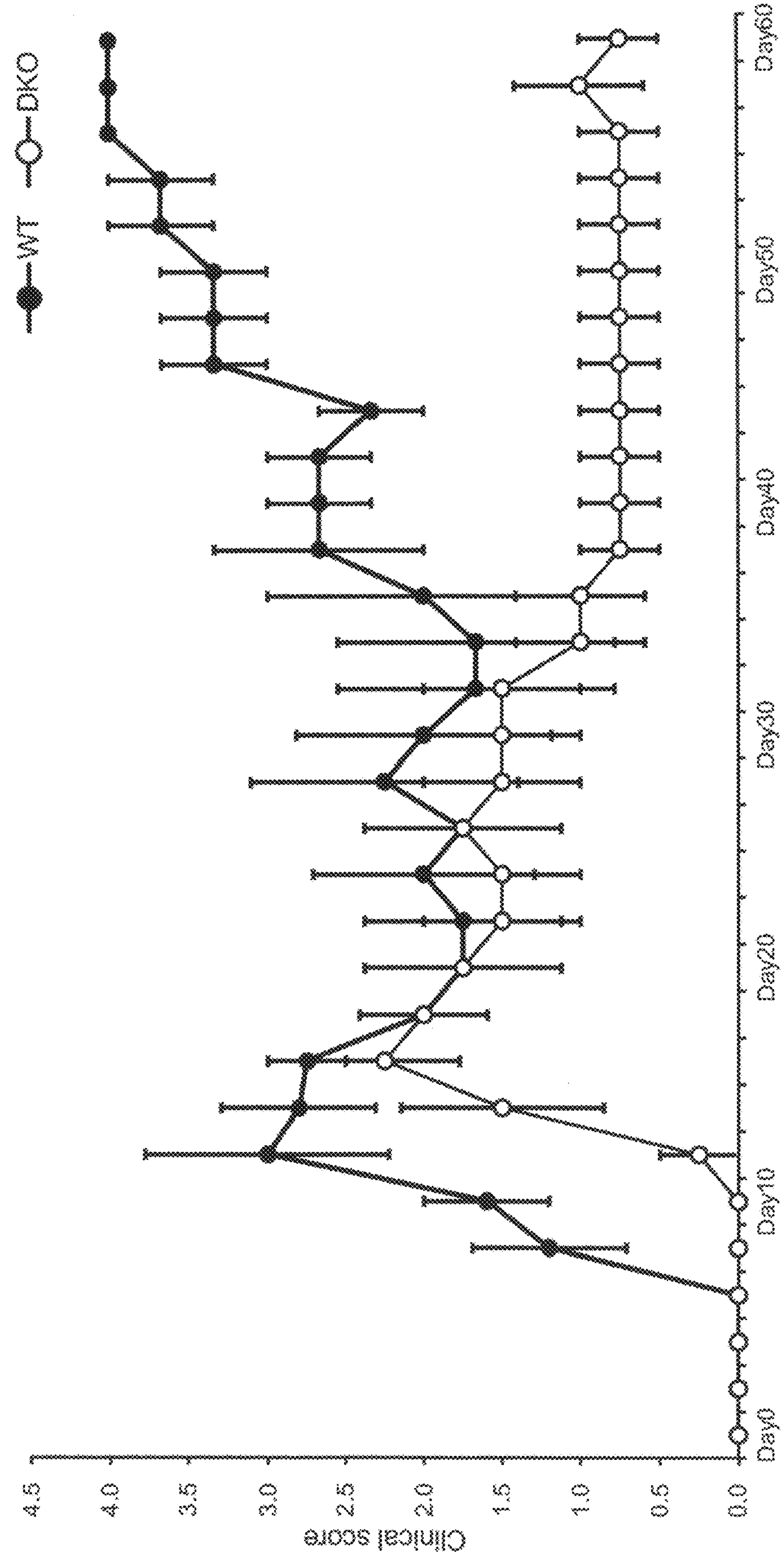
FIG. 13 is a graph obtained by comparing the EAE clinical scores of a GlcNAc6ST-1/2 double-deficient mouse and a wild-type mouse.

By using an experimental autoimmune encephalomyelitis (EAE) model known as an animal model of multiple sclerosis, which is a type of intractable autoimmune-related disease, the effect of the SF1 antibody on an immune-related disease was analyzed. In this model, immunization of a mouse with a myelin oligodendrocyte glycoprotein (MOG) peptide induces an immune response through lymphocyte homing to lymph nodes, resulting in the development of autoimmune encephalomyelitis. First, a comparative study of EAE symptoms was performed in WT mice and G6ST DKO mice (FIG. 13).

As a result, delay in onset, reduction in symptoms at peak, and reduction in symptoms at relapse were observed in the G6ST DKO mice. Therefore, it was found that a 6-sulfosialyl Lewis X glycan synthesized by GlcNAc6ST-1 and GlcNAc6ST-2 in HEV can serve as a therapeutic target for multiple sclerosis.

Figure 14:
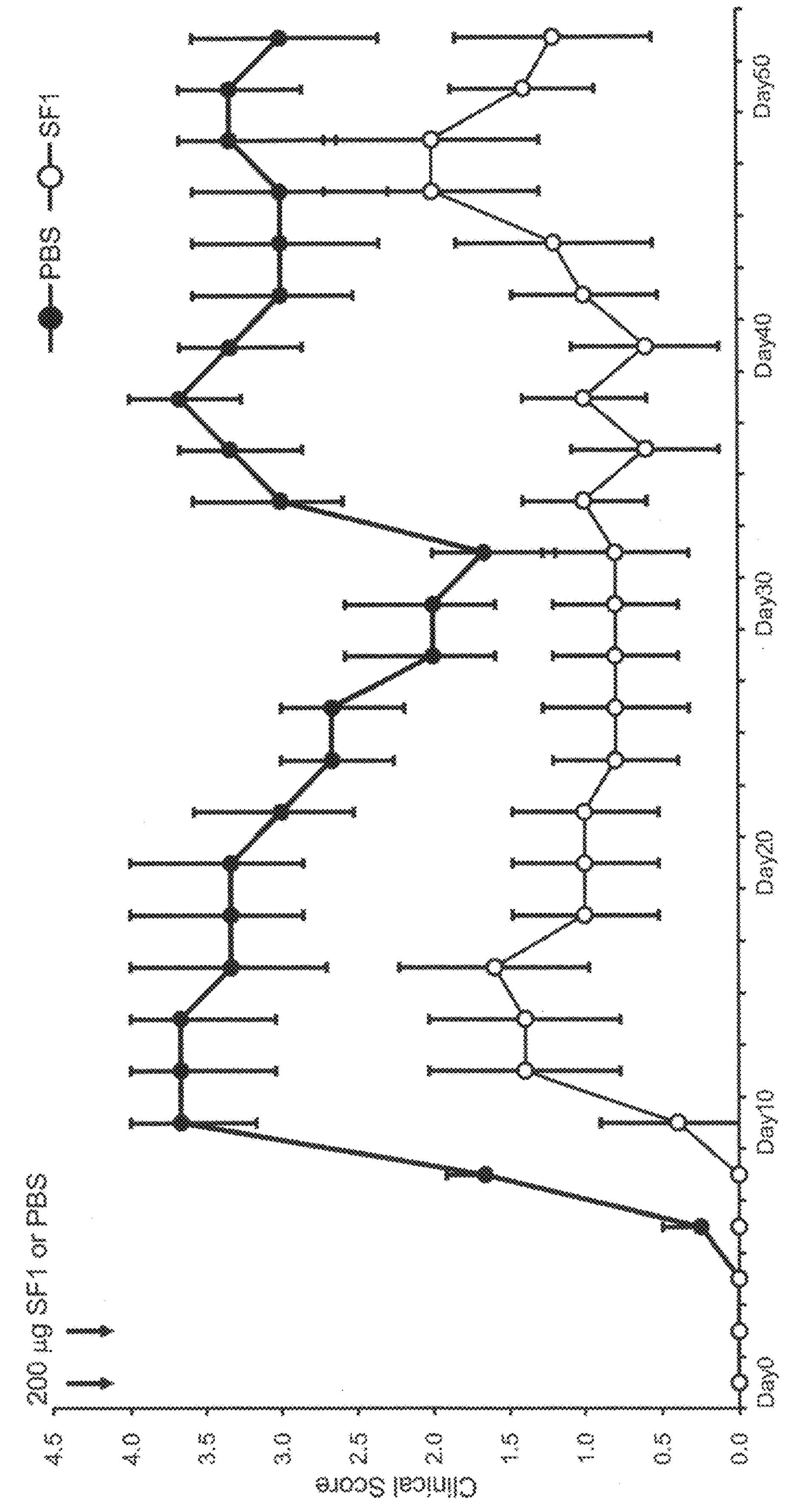
FIG. 14 is a graph showing the effect of administration of SF1 antibody during antigen sensitization on the EAE clinical score.

Therefore, an experiment of suppressing the onset of EAE by the SF1 antibody that specifically binds to the same glycan was performed. When the SF1 antibody was administered to EAE model mice twice on Day 0 and Day 2 after sensitization with the MOG peptide, delay in onset, reduction in symptoms at peak, and reduction in symptoms at relapse were observed in the same manner as in the above-mentioned DKO mice (FIG. 14).

From this, it was found that the SF1 antibody suppresses the onset of EAE.

Figure 15:
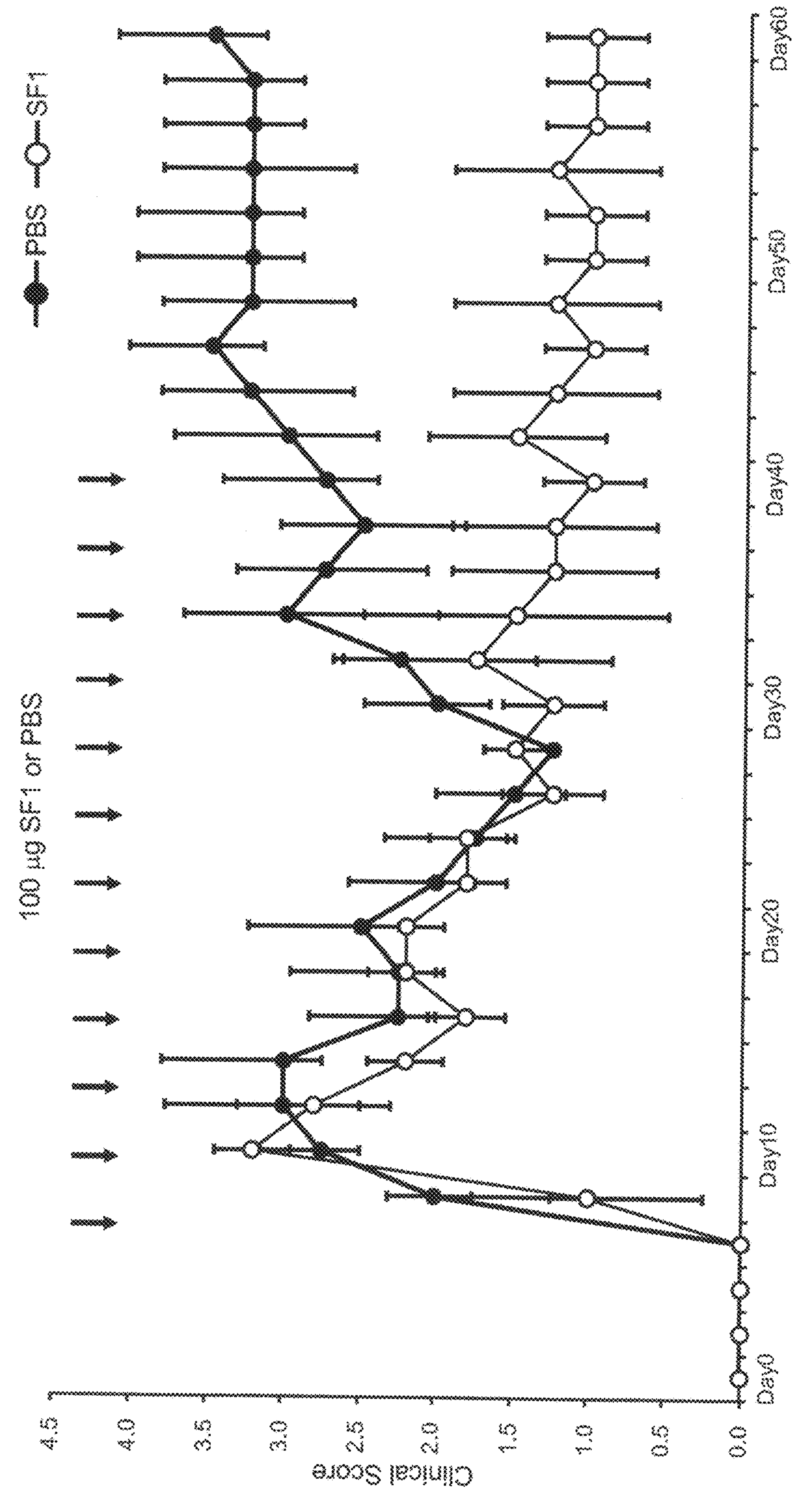
FIG. 15 is a graph showing the effect of administration of SF1 antibody after the onset of EAE (administration of the SF1 antibody from day 8 after initial antigen sensitization) on the EAE clinical score.
Figure 16:
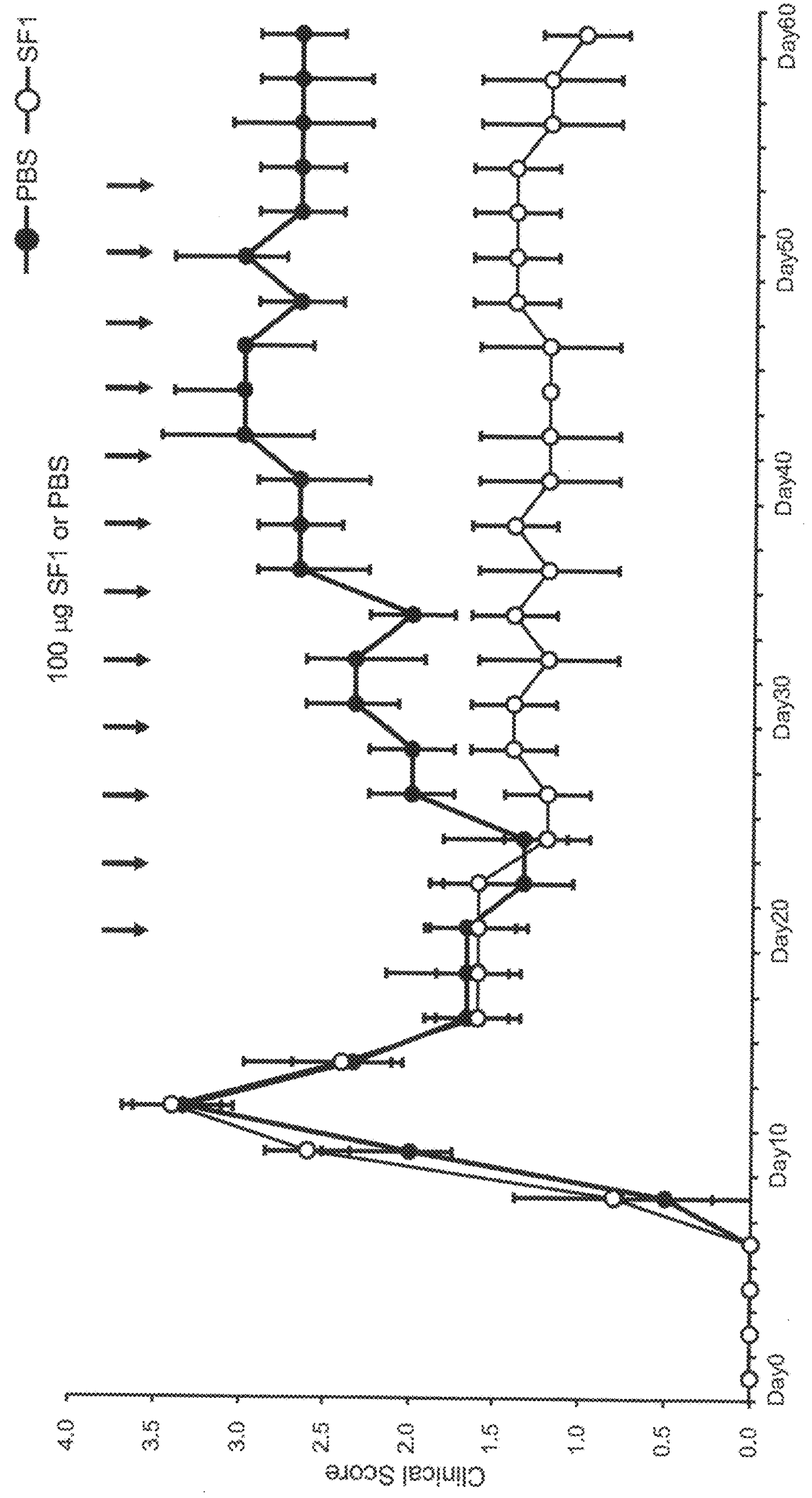
FIG. 16 is a graph showing the effect of administration of SF1 antibody after the onset of EAE (administration of SF1 antibody from day 21 after initial antigen sensitization) on the EAE clinical score.

Further, by administering the SF1 antibody 12 times every 3 days from day 8 after the initial antigen sensitization when the symptoms of EAE began to appear, the relapse seen after day 30 was remarkably suppressed, and even after day 42 when the antibody administration was discontinued, the state where the relapse was suppressed was maintained (FIG. 15). Similarly, by administering the SF1 antibody 12 times every 3 days from day 21 after the initial antigen sensitization when the first peak of EAE passed, the relapse seen after day 30 was remarkably suppressed, and even after day 54 when the antibody administration was discontinued, the state where the relapse was suppressed was maintained (FIG. 16).

Multiple sclerosis is known to repeat relapse and remission. From the above results, the SF1 antibody has an effect of suppressing relapse, and therefore is considered to be an antibody that can be applied to the treatment of multiple sclerosis.

10. Analysis of Effect of SF1 Antibody in Mouse Rheumatoid Arthritis Model

Figure 17:
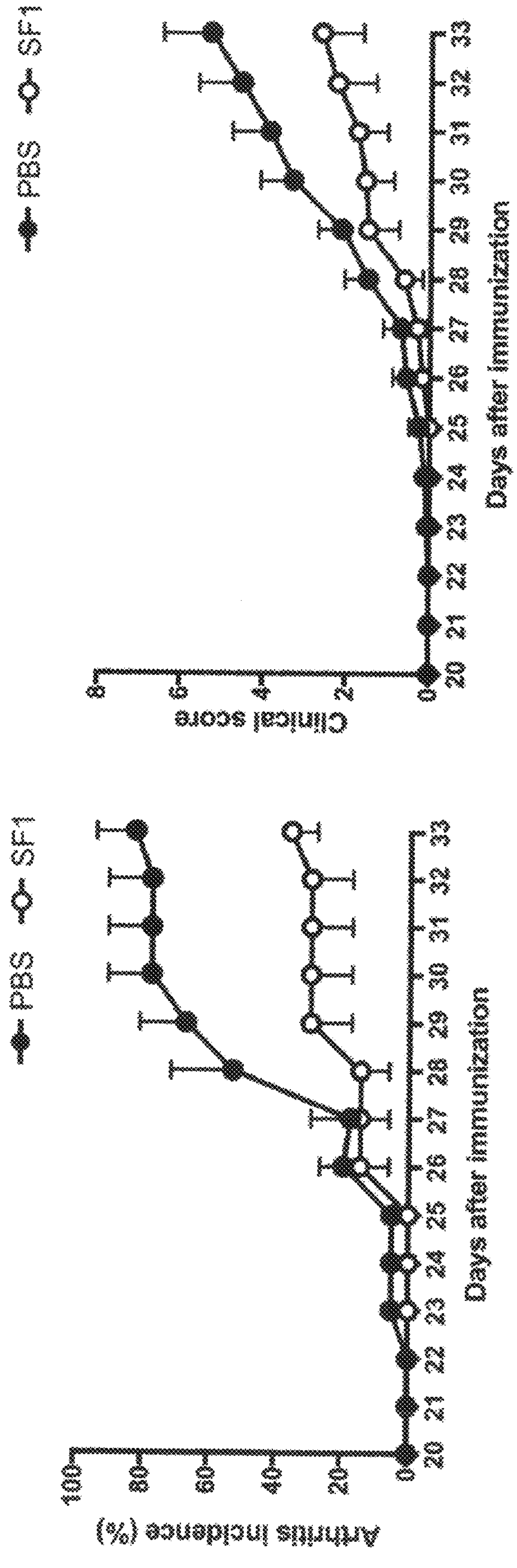
FIG. 17 shows graphs showing the effect of administration of SF1 antibody on the collagen-induced arthritis (CIA) incidence (left) and the clinical score (right).

Next, the effect of the SF1 antibody in a model of an autoimmune-related disease other than EAE was studied. Specifically, in a collagen-induced arthritis model, which is a mouse rheumatoid arthritis model, first subcutaneous antigen administration was performed on day 0, second subcutaneous antigen administration was performed on day 21, and PBS or SF1 was administered on days 24, 27, 30, and 33, and the study was performed (FIG. 17).

As a result, it was shown that both the incidence of arthritis symptoms and the clinical score are inhibited in the SF1 antibody administration group.

11. Analysis of Effect of SF1 Antibody in Mouse Allergic Rhinitis Model

Figure 18:
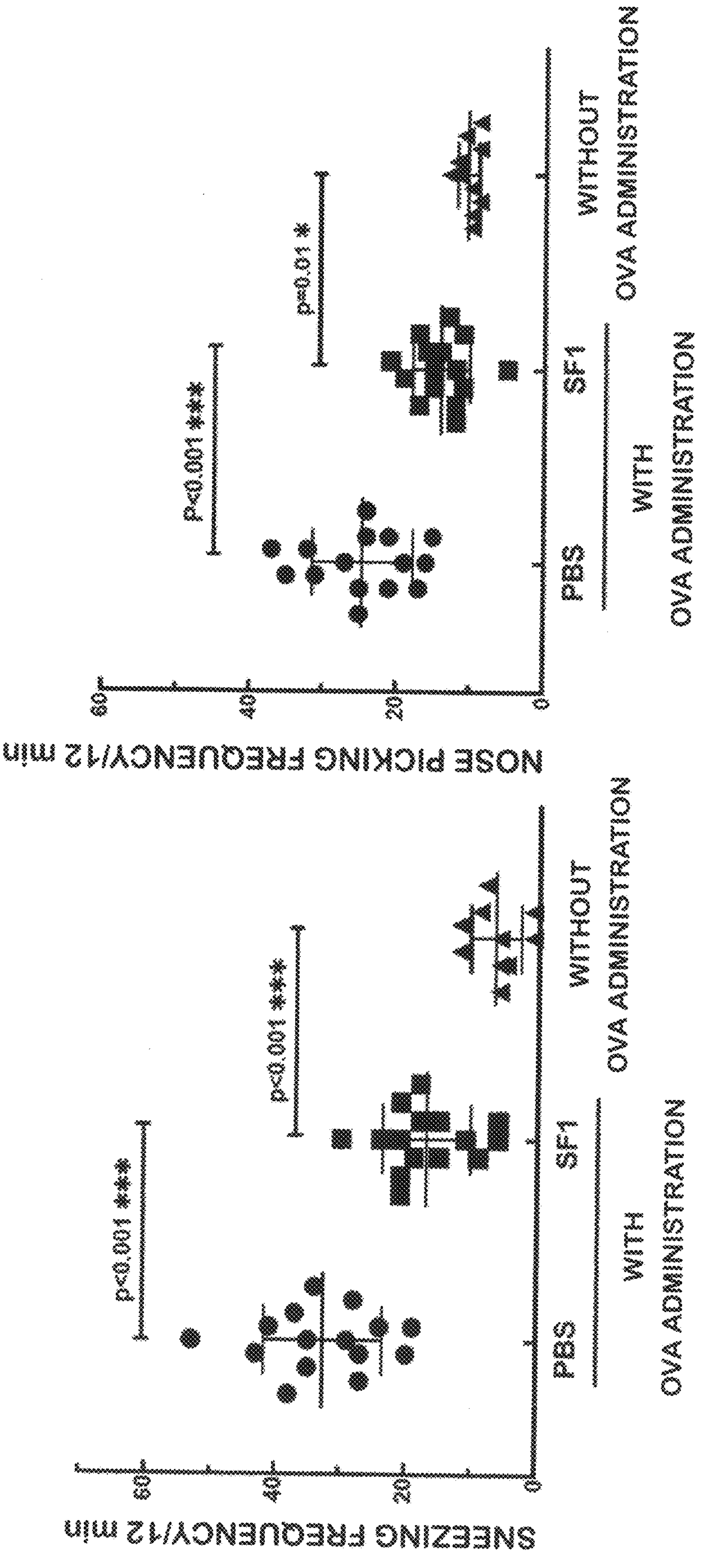
FIG. 18 shows graphs showing the suppressive effect of SF1 antibody on sneezing (left graph) and nose picking behavior (right graph) in a mouse allergic rhinitis model.

Next, the effect of the SF1 antibody in a mouse allergic rhinitis model was studied. Specifically, in a model of allergic rhinitis caused by intranasal administration of ovalbumin (OVA), which is an antigen, and cholera toxin (CT), which has an adjuvant action, to mice four times every other week, PBS or the SF1 antibody was intraperitoneally administered twice in a week, and the study was performed (FIG. 18).

As a result, the sneezing frequency and the nose picking frequency in mice observed for 12 minutes immediately after the fourth intranasal administration of OVA and CT were significantly inhibited in the SF1 antibody administration group.

12. Immunostaining of Normal Human Tissues with SF1 Antibody

Figure 19:
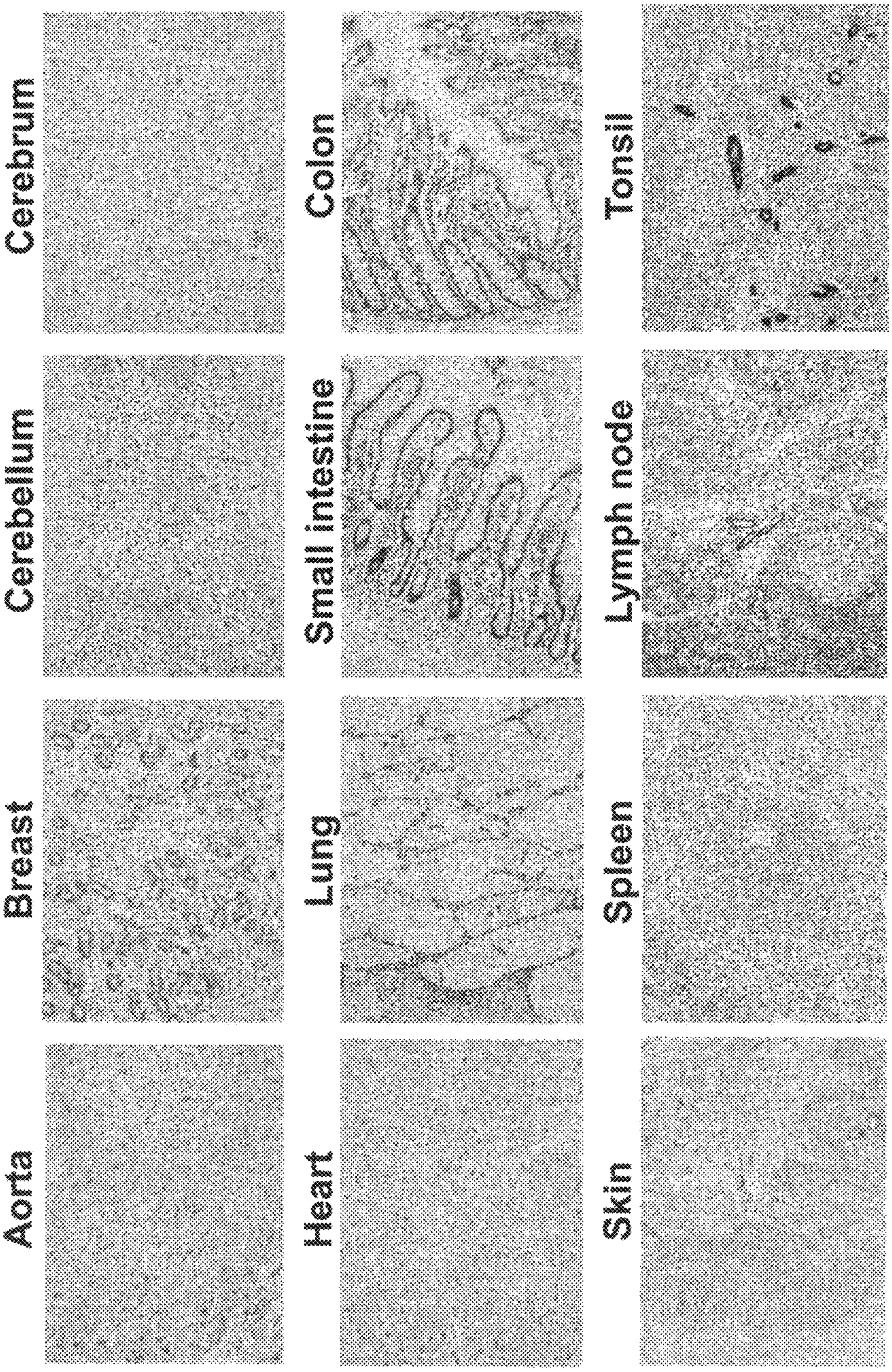
FIG. 19 shows the results of immunostaining of normal human tissues with SF1 antibody.
Figure 20:
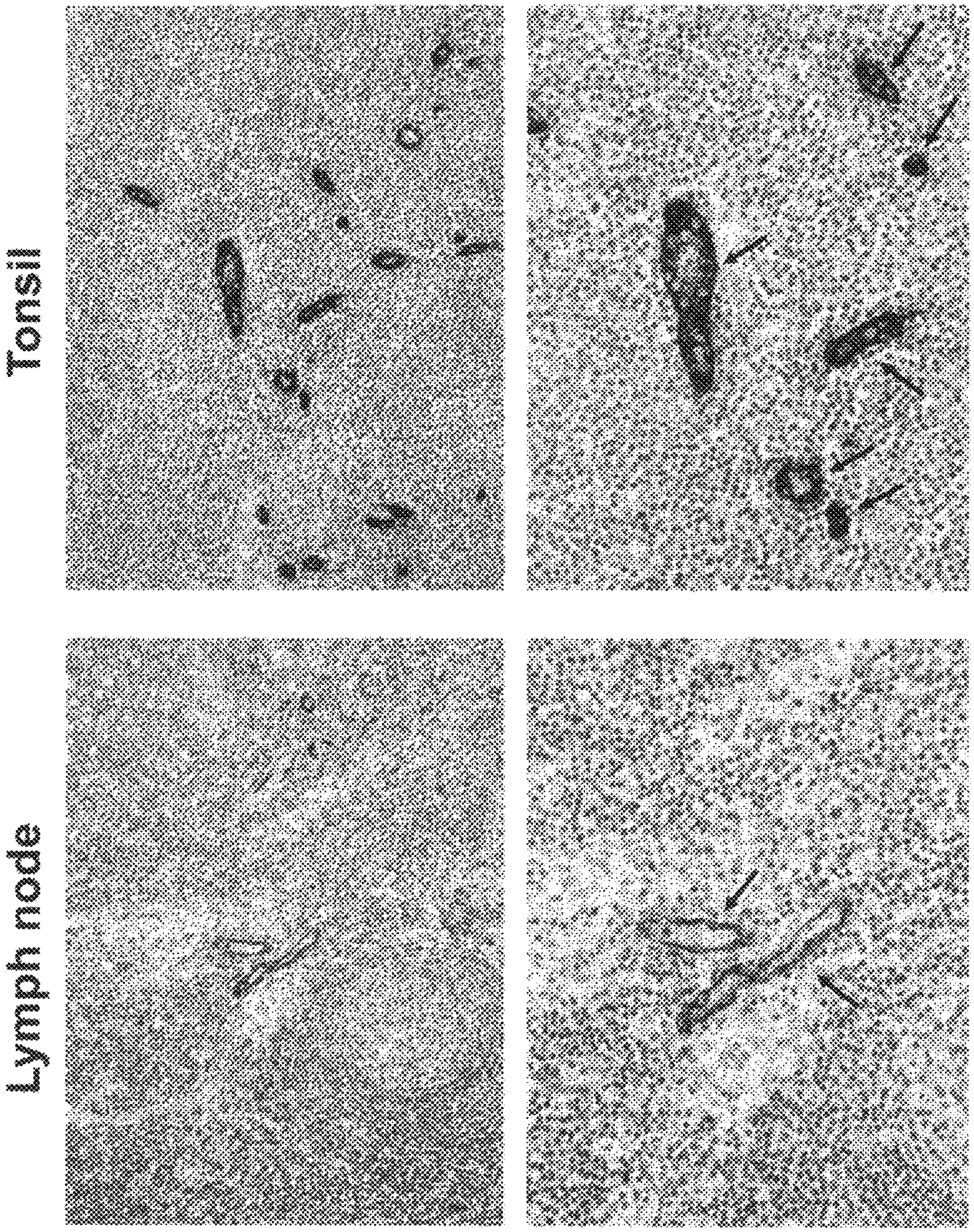
FIG. 20 shows enlarged photographs of the results of lymph nodes and tonsils in the immunostaining photographs in FIG. 19.

When immunohistological staining of normal human tissues with the SF1 antibody was performed, no staining was observed in the aorta, mammary gland, cerebellum, cerebrum, heart, lung, small intestine, large intestine, skin, or spleen, but staining was observed in the lymph node and tonsil (FIGS. 19 and 20).

From the enlarged photographs in FIG. 20, it was found that the SF1 antibody specifically binds to high endothelial venule HEV (arrows in the drawings), which is a blood vessel through which lymphocytes migrate to these lymphoid tissues.

13. Preparation of Humanized Single-Chain SF1 Antibody and Immunostaining Using the Same As a result of trial and error, it was found that the activity was well maintained when using IGHV4-59 among the human antibody heavy chain variable region frame sequences that are highly homologous to the heavy chain variable region frame sequence of the mouse SF1 antibody shown in FIG. 8. Specifically, humanized sequence SF1 heavy chain variable region sequences H1 and H2 in which the heavy chain hypervariable region sequence of the SF1 antibody shown in FIG. 7 was grafted into IGHV4-59 were designed and used for activity evaluation. The sequence of H1 is a sequence in which amino acids at two sites in the human heavy chain variable region frame sequence portion in the sequence of H2 were mutated back to those of the mouse SF1 antibody. As a result of further trial and error, as an example of another sequence, it was found that also when IGHV3-43 was used among the human antibody heavy chain variable region frame sequences that are highly homologous to the heavy chain variable region frame sequence of the SF1 antibody shown in FIG. 8, and amino acids at two sites thereof were mutated back to those of the mouse SF1 antibody, the activity was well maintained. Specifically, a humanized sequence SF1 heavy chain variable region sequence H3 in which the heavy chain hypervariable region sequence shown in FIG. 7 was grafted into IGHV3-43 having such a heavy chain variable region frame sequence was designed and used for activity evaluation.

Similarly, as a result of trial and error, it was found that the activity was well maintained when using IGKV1-39 among the human antibody light chain variable region frame sequences that are highly homologous to the light chain variable region frame sequence of the mouse SF1 antibody shown in FIG. 9. Specifically, humanized sequence SF1 light chain variable region sequences L1 and L2 in which the light chain hypervariable region sequence of the SF1 antibody shown in FIG. 7 was grafted into IGKV1-39 were designed and used for activity evaluation. The sequence of L1 is a sequence in which an amino acid at one site in the human light chain variable region frame sequence portion in the sequence of L2 was mutated back to that of the mouse SF1 antibody. As a result of further trial and error, as an example of another sequence, it was found that also when IGKV6-21 was used among the human antibody light chain variable region frame sequences that are highly homologous to the light chain variable region frame sequence of the SF1 antibody shown in FIG. 9, and an amino acid at one site thereof was mutated back to that of the mouse SF1 antibody, the activity was well maintained. Specifically, a humanized sequence SF1 light chain variable region sequence L3 in which the light chain hypervariable region sequence shown in FIG. 7 was grafted into IGKV6-21 having such a light chain variable region frame sequence was designed and used for activity evaluation.

The amino acid sequences of the above humanized SF1 heavy chain variable regions H1, H2, H3 and humanized SF1 light chain variable regions L1, L2, L3 are shown in FIG. 21. The sequences of CDRH1, CDRH2, CDRH3, CDRL1, CDRL2, and CDRL3 are shown in bold.

Subsequently, by using a cell-free protein synthesis system using a wheat germ extract, humanized SF1 single-chain antibodies (scFvs) containing any of the humanized SF1 heavy chain variable regions H1 to H3 and any of the humanized SF1 light chain variable regions L1 to L3 shown in FIG. 21 in various combinations were produced. The full amino acid sequences of the produced various humanized SF1 scFvs are shown in FIG. 22. The underlined sequence obtained by repeating Gly-Gly-Gly-Gly-Ser (GGGGS) 3 (SEQ ID NO: 29) times (G4S linker) is a linker sequence between the heavy chain and the light chain, and the double-underlined Gly-Leu-Gln-Gln-Gly-Gly-Thr-His-His-His-His-His-His (GLQQGGTHHHHHH) (SEQ ID NO: 30) sequence on the C-terminal side is a tag sequence for binding to a biotinylated anti-$(His)_6$ (SEQ ID NO: 31) antibody. The sequences in bold indicate the sequences of CDRH1, CDRH2, CDRH3, CDRL1, CDRL2, and CDRL3, respectively, from the N-terminal side. The humanized SF1-scFv-H1L1 is a sequence including the humanized SF1 heavy chain variable region H1 and the humanized SF1 light chain variable region L1, the humanized SF1-scFv-H1L2 is a sequence including the humanized SF1 heavy chain variable region H1 and the humanized SF1 light chain variable region L2, the humanized SF1-scFv-H2L1 is a sequence including the humanized SF1 heavy chain variable region H2 and the humanized SF1 light chain variable region L1, and the humanized SF1-scFv-H3L3 is a sequence including the humanized SF1 heavy chain variable region H3 and the humanized SF1 light chain variable region L3.

The humanized SF1-scFv made to form a complex by pre-incubation with a biotinylated anti-$(His)_6$ (SEQ ID NO: 31) antibody was incubated overnight at 4° C. with a mouse lymph node frozen section, and the section was washed with PBS, and thereafter, fluorescent immunostaining was performed by further incubating AlexaFluor 594-labeled streptavidin, which is a fluorescent substance, at room temperature for 1 hour. As a result, the humanized SF1-scFvs produced by any combination showed specific stainability to HEV (FIG. 23). From the above, it was found that the sequence of the hypervariable region of the SF1 antibody shown in FIG. 7 is a versatile sequence that has activity even when it is linked to various variable region frame sequences of a human antibody and a mouse antibody.

14. Preparation of Humanized SF1 antibody and Immunostaining Using the Same

Figures 25, 26:
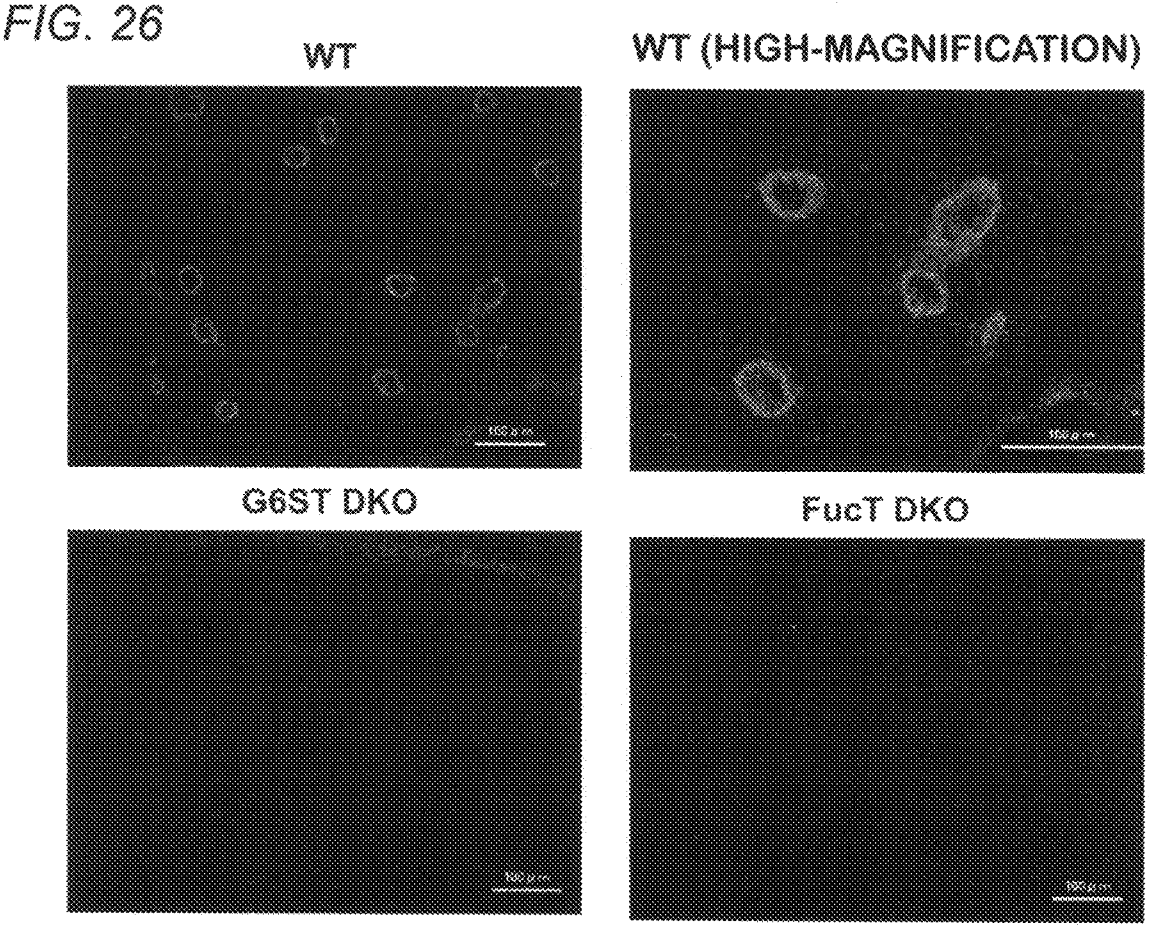
FIG. 25 shows the full-length amino acid sequence of the light chain of the humanized SF1 antibody.
FIG. 26 shows the results of fluorescent immunostaining of mouse lymph nodes with the humanized SF1 antibody composed of the heavy chain and the light chain of the humanized SF1 antibody shown in FIGS. 24 and 25.

A humanized SF1 heavy chain full length amino acid sequence was designed by linking the humanized SF1 heavy chain variable region sequence H1 shown in FIG. 21 to the human antibody heavy chain IgG1 constant region (FIG. 24). Similarly, a humanized SF1 light chain full length amino acid sequence was designed by linking the humanized SF1 light chain variable region sequence L1 shown in FIG. 21 to a k chain constant region, which is a human antibody light chain (FIG. 25). Genes encoding the humanized SF1 heavy chain full length amino acid sequence and the humanized SF1 light chain full length amino acid sequence were introduced into an HEK 293T cell, which is a human-derived cell line, thereby producing a humanized SF1 antibody.

The full amino acid sequence of the heavy chain of the humanized SF1 antibody is represented by SEQ ID NO: 25 and shown in FIG. 24. The sequences of CDRH1, CDRH2, and CDRH3 are shown in bold.

The full amino acid sequence of the light chain variable region of the humanized SF1 antibody is represented by SEQ ID NO: 26 and shown in FIG. 25. The sequences of CDRL1, CDRL2, and CDRL3 are shown in bold.

When fluorescent immunostaining of mouse lymph nodes was performed using the humanized SF1 antibody, the humanized SF1 antibody specifically bound to a high endothelial venule of a wild-type (WT) mouse and did not react at all with a G6ST DKO mouse deficient in a sulfate group of 6-sulfosialyl Lewis X and FucT DKO deficient in fucose. (FIG. 26). This indicates that the specificity of the humanized SF1 antibody for 6-sulfosialyl Lewis X is high.

From the above results, it was confirmed that the humanized antibody including the hypervariable region amino acid sequences of the heavy chain and light chain variable regions of the SF1 antibody retains specific sugar binding specificity for 6-sulfosialyl Lewis X in the same manner as the mouse SF1 antibody.

Figure 27:
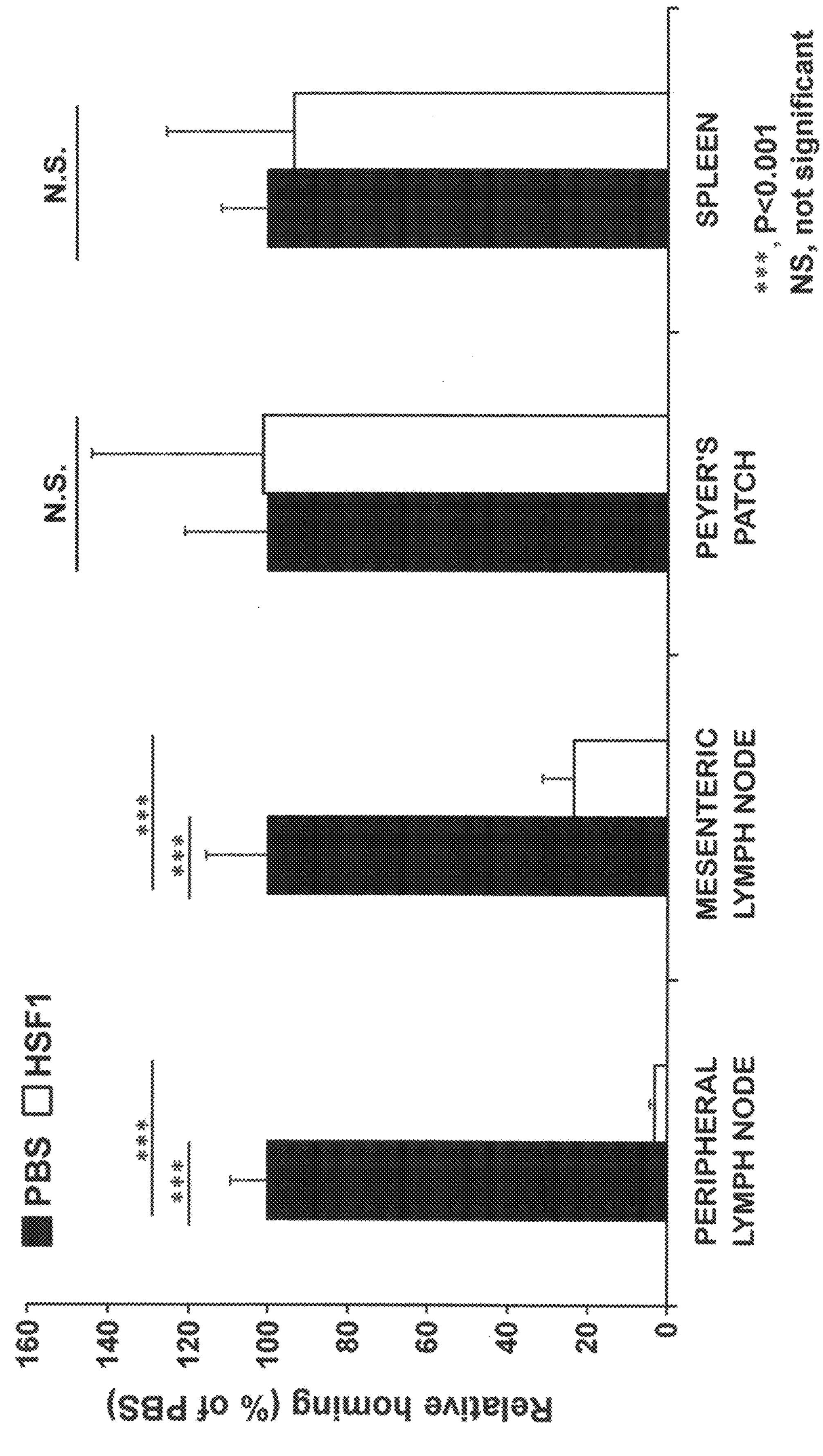
FIG. 27 shows results obtained by analyzing the inhibitory effect of the humanized SF1 antibody (HSF1 antibody) on lymphocyte homing.

15. Analysis of Inhibitory Effect of Humanized SF1 Antibody on Lymphocyte Homing Next, a WT mouse was intravenously injected with the humanized SF1 antibody or PBS through the tail vein, and then intravenously injected with lymphocytes (derived from mesenteric lymph nodes and spleen) labeled with a fluorescent substance CFSE through the tail vein. After 2 hours, each lymph tissue was collected, and the number of CFSE-labeled lymphocytes homing to each tissue was examined (FIG. 27).

As a result, the humanized SF1 antibody suppressed lymphocyte homing to mouse peripheral lymph nodes by about 90% or more in the same manner as the mouse SF1 antibody. In addition, the humanized SF1 antibody suppressed homing to mesenteric lymph nodes by about 70%. On the other hand, the humanized SF1 antibody did not show a significant inhibitory effect on homing to the Peyer's patch or spleen.

16. Analysis of Effect of Humanized SF1 Antibody in EAE Model

Figure 28:
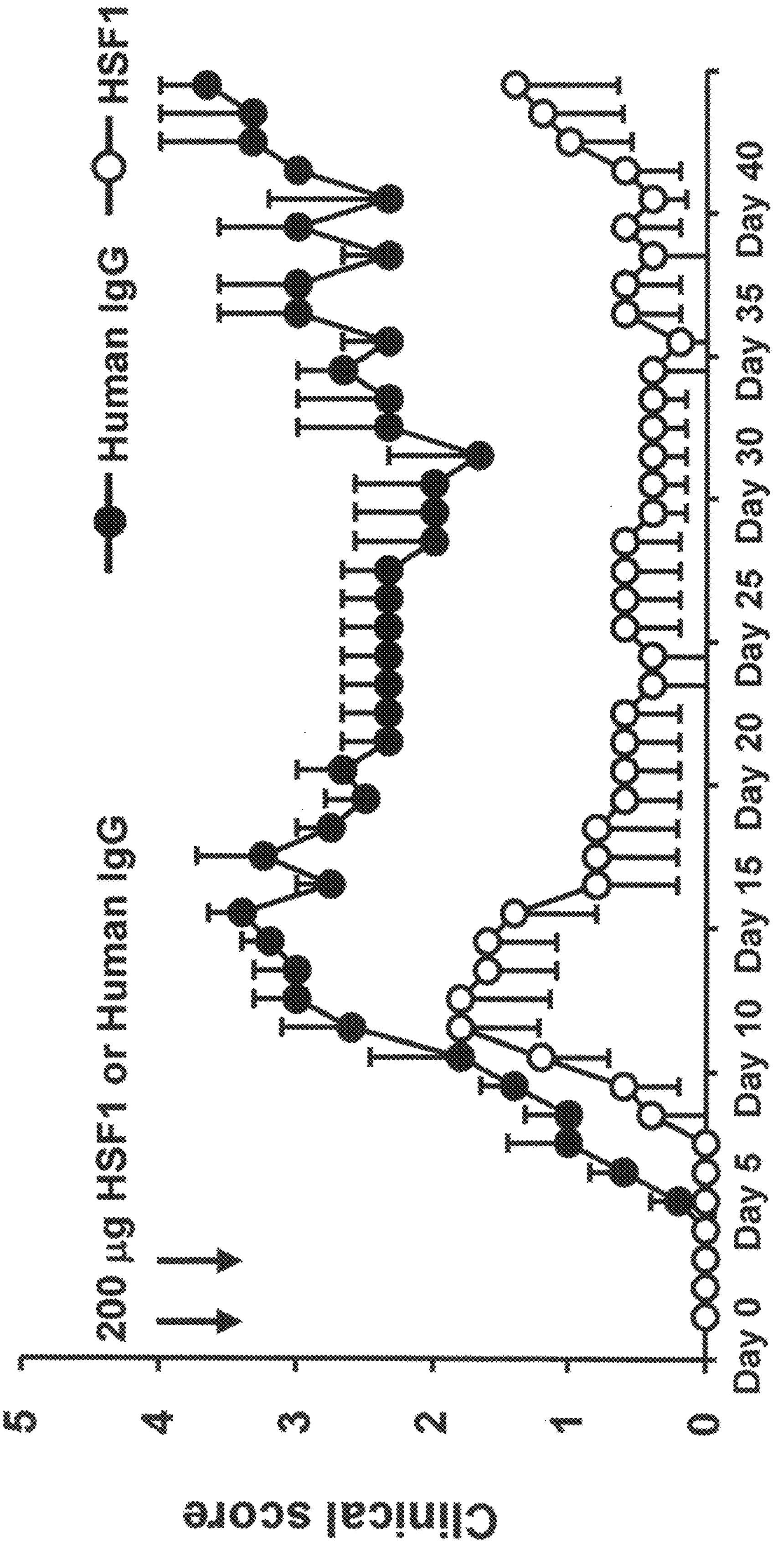
FIG. 28 is a graph showing the effect of administration of the humanized SF1 antibody (HSF1 antibody) during antigen sensitization on the EAE clinical score.

An experiment of suppressing the onset of EAE by the humanized SF1 antibody was performed. When the humanized SF1 antibody was administered to EAE model mice twice on Day 0 and Day 2 after sensitization with the MOG peptide, delay in onset, reduction in symptoms at peak, and reduction in symptoms at relapse were observed in the same manner as the mouse SF1 antibody (FIG. 28).

From this, it was found that the humanized SF1 antibody suppresses the onset of EAE.

17. Preparation of Humanized SF1 Antibody with Modified Fc Region Sequence

Further, a humanized SF1 antibody with a modified Fc region sequence was prepared. That is, a full-length amino acid sequence of a humanized SF1 heavy chain IgG1-LALA variant in which Leu234-Leu235 according to the Eu numbering were substituted with Ala234-Ala235 in the humanized SF1 heavy chain IgG1 constant region shown in FIG. 24 was designed (FIG. 29). Further, similarly, a full-length amino acid sequence of a humanized SF1 heavy chain IgG4-SPLE variant, in which after the humanized SF1 heavy chain IgG1 constant region shown in FIG. 24 was substituted with the IgG4 constant region, Ser228 and Leu235 according to the Eu numbering were substituted with Pro and Glu, respectively, was designed (FIG. 30). Each of the genes encoding the full-length amino acid sequences of the humanized SF1 heavy chains with the modified Fc region sequence was introduced into HEK 293T cells together with the gene encoding the humanized SF1 light chain full length amino acid sequence shown in FIG. 25, thereby producing a humanized SF1 antibody-IgG1-LALA variant (HSF1-LALA) and a humanized SF1 antibody-IgG4-SPLE variant (HSF1-G4PE).

The full amino acid sequence of the heavy chain IgG1-LALA variant of the humanized SF1 antibody is represented by SEQ ID NO: 27 and shown in FIG. 29. The sequences of CDRH1, CDRH2, and CDRH3 are shown in bold.

The full amino acid sequence of the heavy chain IgG4-SPLE variant of the humanized SF1 antibody is represented by SEQ ID NO: 28 and shown in FIG. 30. The sequences of CDRH1, CDRH2, and CDRH3 are shown in bold.

Figure 31:
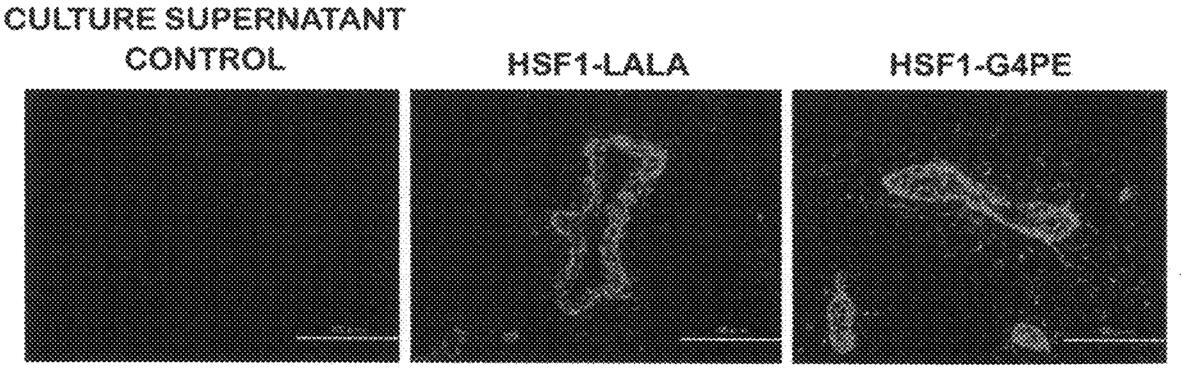
FIG. 31 shows the results of fluorescent immunostaining of mouse lymph nodes with a humanized SF1 antibody-IgG1-LALA variant (HSF1-LALA) and a humanized SF1 antibody-IgG4-SPLE variant (HSF1-G4PE) composed of the heavy chain modified variant of the humanized SF1 antibody shown in FIG. 29 or 30 and the light chain shown in FIG. 25.

Subsequently, fluorescent immunostaining of mouse lymph nodes was performed using a culture supernatant of 293T cells containing either of the humanized SF1 antibody-IgG1-LALA variant (HSF1-LALA) and the humanized SF1 antibody-IgG4-SPLE variant (HSF1-G4PE), each of which is formed from the heavy chain variant of the humanized SF1 antibody shown in FIG. 29 or 30 and the light chain shown in FIG. 25. As a result, no staining was observed only with the culture supernatant of 293T cells without gene transfer, but specific binding was observed in the mouse lymph node high endothelial venule by the HSF1-LALA-containing culture supernatant and the HSF1-G4PE-containing culture supernatant (FIG. 31).

From the above results, it was confirmed that the humanized SF1 antibody with a modified Fc region sequence also retains specific tissue binding affinity. It is known that such a humanized antibody with a modified Fc region sequence reduces the effector activity mediated by the Fc region of the antibody and reduces the risk of side effects. From the above, it is considered that the humanized SF1 antibody and the humanized SF1 antibody with a modified Fc region sequence have a highly efficient lymphocyte homing inhibitory effect due to specific tissue binding affinity in the same manner as the mouse SF1 antibody, and are useful as a therapeutic antibody that exhibits a therapeutic effect on an immune-related disease such as an autoimmune disease or an allergic disease.

SEQUENCE LISTING FREE TEXT

SEQ ID NO: 1: amino acid sequence of CDRH1 of SF1 antibody

SEQ ID NO: 2: amino acid sequence of CDRH2 of SF1 antibody

SEQ ID NO: 3: amino acid sequence of CDRH3 of SF1 antibody

SEQ ID NO: 4: amino acid sequence of CDRL1 of SF1 antibody

SEQ ID NO: 5: amino acid sequence of CDRL2 of SF1 antibody

SEQ ID NO: 6: amino acid sequence of CDRL3 of SF1 antibody

SEQ ID NO: 7: nucleotide sequence of CDRH1 of SF1 antibody

SEQ ID NO: 8: nucleotide sequence of CDRH2 of SF1 antibody

SEQ ID NO: 9: nucleotide sequence of CDRH3 of SF1 antibody

SEQ ID NO: 10: nucleotide sequence of CDRL1 of SF1 antibody

SEQ ID NO: 11: nucleotide sequence of CDRL2 of SF1 antibody

SEQ ID NO: 12: nucleotide sequence of CDRL3 of SF1 antibody

SEQ ID NO: 13: amino acid sequence of heavy chain variable region of SF1 antibody SEQ ID NO: 14: amino acid sequence of light chain variable region of SF1 antibody SEQ ID NO: 15: amino acid sequence of heavy chain variable region H1 of humanized SF1 antibody SEQ ID NO: 16: amino acid sequence of heavy chain variable region H2 of humanized SF1 antibody SEQ ID NO: 17: amino acid sequence of heavy chain variable region H3 of humanized SF1 antibody SEQ ID NO: 18: amino acid sequence of light chain variable region L1 of humanized SF1 antibody SEQ ID NO: 19: amino acid sequence of light chain variable region L2 of humanized SF1 antibody SEQ ID NO: 20: amino acid sequence of light chain variable region L3 of humanized SF1 antibody SEQ ID NO: 21: amino acid sequence of humanized SF1-scFv-H1L1

SEQ ID NO: 22: amino acid sequence of humanized SF1-scFv-H1L2

SEQ ID NO: 23: amino acid sequence of humanized SF1-scFv-H2L1

SEQ ID NO: 24: amino acid sequence of humanized SF1-scFv-H3L3

SEQ ID NO: 25: amino acid sequence of full-length heavy chain of humanized SF1 antibody SEQ ID NO: 26: amino acid sequence of full-length light chain of humanized SF1 antibody SEQ ID NO: 27: amino acid sequence of full-length heavy chain IgG1-LALA variant of humanized SF1 antibody SEQ ID NO: 28: amino acid sequence of full-length heavy chain IgG4-SPLE variant of humanized SF1 antibody SEQ ID NO: 29: amino acid sequence of G4S linker

The invention claimed is:

1. An antibody or a fragment thereof, which specifically binds to a 6-sulfosialyl Lewis X glycan, where the binding requires fucose, a sulfate group, and a sialic acid that form the 6-sulfosialyl Lewis X glycan, wherein the antibody or the fragment thereof comprises:

a heavy chain variable region comprising the following CDRs:

(a) CDRH1 comprising the amino acid sequence represented by SEQ ID NO: 1;

(b) CDRH2 comprising the amino acid sequence represented by SEQ ID NO: 2; and (c) CDRH3 comprising the amino acid sequence represented by SEQ ID NO: 3; and a light chain variable region comprising the following CDRs:

(d) CDRL1 comprising the amino acid sequence represented by SEQ ID NO: 4;

(e) CDRL2 comprising the amino acid sequence represented by SEQ ID NO: 5; and (f) CDRL3 comprising the amino acid sequence represented by SEQ ID NO: 6.

2. The antibody or the fragment thereof according to claim 1, wherein the heavy chain variable region comprises the amino acid sequence represented by any of SEQ ID NOS: 15 to 17 and the light chain variable region comprises the amino acid sequence represented by any of SEQ ID NOS: 18 to 20.

3. The antibody or the fragment thereof according to claim 1, which comprises any of the following combinations of the heavy chain variable region and the light chain variable region:

(1) the heavy chain variable region comprises the amino acid sequence represented by SEQ ID NO: 15 and the light chain variable region comprises the amino acid sequence represented by SEQ ID NO: 18;

(2) the heavy chain variable region comprises the amino acid sequence represented by SEQ ID NO: 15 and the light chain variable region comprises the amino acid sequence represented by SEQ ID NO: 19;

(3) the heavy chain variable region comprises the amino acid sequence represented by SEQ ID NO: 16 and the light chain variable region comprises the amino acid sequence represented by SEQ ID NO: 18; and (4) the heavy chain variable region comprises the amino acid sequence represented by SEQ ID NO: 17 and the light chain variable region comprises the amino acid sequence represented by SEQ ID NO: 20.

4. The antibody or the fragment thereof according to claim 1, which comprises the heavy chain variable region comprises the amino acid sequence represented by SEQ ID NO: 13 and the light chain variable region comprises the amino acid sequence represented by SEQ ID NO: 14.

5. The antibody or the fragment thereof according to claim 1, which comprises any of the following combinations of a heavy chain and a light chain:

(1) the heavy chain comprises the amino acid sequence represented by SEQ ID NO: 25 and the light chain comprises the amino acid sequence represented by SEQ ID NO: 26;

(2) the heavy chain comprises the amino acid sequence represented by SEQ ID NO: 27 and the light chain comprises the amino acid sequence represented by SEQ ID NO: 26; and (3) the heavy chain comprises the amino acid sequence represented by SEQ ID NO: 28 and the light chain comprises the amino acid sequence represented by SEQ ID NO: 26.

6. The antibody or the fragment thereof according to claim 1, which inhibits binding of a high endothelial venule expressing a 6-sulfosialyl Lewis X glycan to L-selectin.

7. The antibody or the fragment thereof according to claim 1, wherein a constant region is derived from a human.

8. The antibody or the fragment thereof according to claim 1, which is humanized.

9. The antibody or the fragment thereof according to claim 1, which is selected from the group consisting of Fab, F(ab')2, Fab', Fv, and a single-chain antibody.

10. The antibody or the fragment thereof according to claim 9, wherein the single-chain antibody comprises the amino acid sequence represented by any of SEQ ID NOS: 21 to 24.

11. The antibody or the fragment thereof according to claim 1, wherein the antibody or the fragment thereof exhibits a dissociation constant ($K_D$ value) of $1\times10^{-6}$ M or less for the 6-sulfosialyl Lewis X glycan.

12. A polynucleotide encoding the antibody or the fragment thereof according to claim 1.

13. An expression vector, comprising the polynucleotide according to claim 12.

14. A host cell transfected with the expression vector according to claim 13.

15. The host cell according to claim 14, which is a eukaryotic cell.

16. A hybridoma producing the antibody according to claim 1.

17. A lymphocyte homing inhibitor, comprising the antibody or the fragment thereof according to claim 1, the polynucleotide encoding the antibody or the fragment thereof according to claim 1, or the expression vector comprising the polynucleotide encoding the antibody or the fragment thereof according to claim 1.

18. A pharmaceutical composition, comprising the antibody or the fragment thereof according to claim 1, the polynucleotide encoding the antibody or the fragment thereof according to claim 1, or the expression vector comprising the polynucleotide encoding the antibody or the fragment thereof according to claim 1.

19. A method for treating a disease, or inhibiting the development or relapse of a disease, caused by an overactive immune response mediated by lymphocyte homing, the method comprises administering to a subject in need thereof the pharmaceutical composition according to claim 18.

20. The method according to claim 19, wherein the disease caused by an overactive immune response mediated by lymphocyte homing is an immune-related disease.

21. The method according to claim 20, wherein the immune-related disease is an allergic disease or an autoimmune disease.

22. The method according to claim 21, wherein the immune-related disease is an allergic disease selected from the group consisting of allergic rhinitis, atopic dermatitis, food allergy, oral allergy syndrome, drug allergy, pollen allergy, allergic conjunctivitis, eosinophilic pneumonia, allergic gastroenteritis, urticaria, photosensitive disorder, metal allergy, cat allergy, mite allergy, and asthma.

23. The method according to claim 21, wherein the immune-related disease is an autoimmune disease selected from the group consisting of multiple sclerosis including relapsing-remitting multiple sclerosis, primary progressive multiple sclerosis, and secondary progressive multiple sclerosis; psoriasis; rheumatoid arthritis; psoriatic arthritis; systemic lupus erythematosus (SLE); ulcerative colitis; Crohn's disease; benign lymphocytic vasculitis; thrombocytopenia purpura; sudden thrombocytopenia; idiopathic autoimmune hemolytic anemia; pure red-cell aplasia; Sjogren's syndrome; a rheumatic disease; a connective tissue disease; inflammatory rheumatism; degenerative rheumatism; non-articular rheumatism; juvenile rheumatoid arthritis; muscle rheumatism; chronic polyarthritis; cryoglobulin vasculitis; ANCA-associated vasculitis; antiphospholipid syndrome; myasthenia gravis; autoimmune hemolytic anemia; Guillain-Barre syndrome; chronic immune polyneuropathy; autoimmune thyroiditis; insulin-dependent diabetes mellitus; type 1 diabetes mellitus; Addison's disease; membranous glomerulonephropathy; Goodpasture's disease; autoimmune gastritis; autoimmune atrophic gastritis; pernicious anemia; pemphigus; pemphigus vulgaris; hepatic cirrhosis; primary biliary cirrhosis; dermatomyositis; polymyositis; fibromyositis; muscle sclerosis; celiac disease; immunoglobulin A nephropathy; Henoch-Schonlein purpura; Evans' syndrome; psoriasis arthropathica; Graves' disease; Graves' ophthalmopathy; scleroderma; systemic scleroderma; progressive systemic scleroderma; primary biliary cirrhosis; Hashimoto's thyroiditis; primary myxedema; sympathetic ophthalmia; autoimmune uveitis; hepatitis; chronic active hepatitis; a collagen disease; ankylosing spondylitis; shoulder periarthritis; nodular panarteritis; chondrocalcinosis; Wegener's granulomatosis; microscopic polyangiitis; chronic urticaria; a bullous skin disease; pemphigoid; Devic's disease; pediatric autoimmune hemolytic anemia; refractory or chronic autoimmune cytopenia; acquired hemophilia A; cold agglutinin disease; neuromyelitis optica; stiff-person syndrome; pancreatitis; myocarditis; vasculitis; gastritis; gout; gouty arthritis; normocomplementemic urticarial vasculitis; pericarditis; myositis; anti-synthetase syndrome; scleritis; macrophage activation syndrome; Behcet's syndrome; PAPA syndrome; Blau syndrome; adult and juvenile Still's disease; cryopyrin-associated periodic syndrome; Muckle-Wells syndrome; familial cold autoinflammatory syndrome; neonatal-onset multisystem inflammatory disease; familial Mediterranean fever; chronic infantile neurological cutaneous and articular syndrome; systemic-onset juvenile idiopathic arthritis; hyper IgD syndrome; Schnitzler's syndrome; autoimmune retinopathy; atherosclerosis; chronic prostatitis; and TNF receptor-associated periodic syndrome (TRAPS).

24. The method according to claim 23, wherein the autoimmune disease is multiple sclerosis or a collagen disease.

25. The method according to claim 24, wherein the collagen disease is one or multiple diseases selected from the group consisting of rheumatoid arthritis, systemic lupus erythematosus, scleroderma, dermatomyositis, polyarteritis nodosa, a mixed connective tissue disease, Sjogren's syndrome, microscopic polyangiitis, eosinophilic granulomatosis with polyangiitis, hypersensitivity vasculitis, Behcet's disease, Cogan's syndrome, RS3PE, giant cell arteritis, adult-onset Still's disease, polymyalgia rheumatica, fibromyalgia, and SAPHO syndrome.

26. The method according to claim 19, wherein the composition further comprises an agent for treating a disease, or inhibiting the development or relapse of a disease, caused by an overactive immune response mediated by lymphocyte homing.

27. A method for producing the antibody or the fragment thereof according to claim 1, comprising a step of culturing the host cell transfected with the expression vector comprising the polynucleotide encoding the antibody or the fragment thereof according to claim 1, or the hybridoma producing the antibody according to claim 1.

* * * * *

SEQUENCE LISTING

```
<160> NUMBER OF SEQ ID NOS: 31

<210> SEQ ID NO 1
<211> LENGTH: 8
<212> TYPE: PRT
<213> ORGANISM: Mus musculus

<400> SEQUENCE: 1

Gly Phe Ser Leu Thr Ser Tyr Ala
1               5


<210> SEQ ID NO 2
<211> LENGTH: 7
<212> TYPE: PRT
<213> ORGANISM: Mus musculus

<400> SEQUENCE: 2

Ile Trp Gly Gly Gly Ser Thr
1               5


<210> SEQ ID NO 3
<211> LENGTH: 11
<212> TYPE: PRT
<213> ORGANISM: Mus musculus

<400> SEQUENCE: 3

Ala Lys His Glu Lys Leu Gly Arg Phe Pro Tyr
1               5                   10


<210> SEQ ID NO 4
<211> LENGTH: 5
<212> TYPE: PRT
<213> ORGANISM: Mus musculus

<400> SEQUENCE: 4

Ser Ser Val Ser Tyr
1               5


<210> SEQ ID NO 5
<211> LENGTH: 3
<212> TYPE: PRT
<213> ORGANISM: Mus musculus

<400> SEQUENCE: 5

Glu Ile Ser
1


<210> SEQ ID NO 6
<211> LENGTH: 9
<212> TYPE: PRT
<213> ORGANISM: Mus musculus

<400> SEQUENCE: 6

Gln Gln Trp Asn Tyr Pro Leu Ala Thr
1               5


<210> SEQ ID NO 7
<211> LENGTH: 24
<212> TYPE: DNA
```

<213> ORGANISM: Mus musculus

<400> SEQUENCE: 7
gggttttcat taaccagcta tgct 24

<210> SEQ ID NO 8
<211> LENGTH: 21
<212> TYPE: DNA
<213> ORGANISM: Mus musculus

<400> SEQUENCE: 8
atatggggtg gtggaagcac a 21

<210> SEQ ID NO 9
<211> LENGTH: 33
<212> TYPE: DNA
<213> ORGANISM: Mus musculus

<400> SEQUENCE: 9
gccaaacatg aaaaactggg acgttttcct tac 33

<210> SEQ ID NO 10
<211> LENGTH: 15
<212> TYPE: DNA
<213> ORGANISM: Mus musculus

<400> SEQUENCE: 10
tcgagtgtaa gttac 15

<210> SEQ ID NO 11
<211> LENGTH: 9
<212> TYPE: DNA
<213> ORGANISM: Mus musculus

<400> SEQUENCE: 11 gaaatatcc 9

<210> SEQ ID NO 12
<211> LENGTH: 27
<212> TYPE: DNA
<213> ORGANISM: Mus musculus

<400> SEQUENCE: 12
cagcagtgga attatcctct ggccacg 27

<210> SEQ ID NO 13
<211> LENGTH: 117
<212> TYPE: PRT
<213> ORGANISM: Mus musculus

<400> SEQUENCE: 13

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80
```

```
Lys Met Asn Ser Leu Gln Thr Asp Asp Thr Ala Met Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ala
        115


<210> SEQ ID NO 14
<211> LENGTH: 106
<212> TYPE: PRT
<213> ORGANISM: Mus musculus

<400> SEQUENCE: 14

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ala Thr
                85                  90                  95

Phe Gly Gly Gly Thr Lys Leu Glu Ile Lys
            100                 105


<210> SEQ ID NO 15
<211> LENGTH: 117
<212> TYPE: PRT
<213> ORGANISM: Artificial Sequence
<220> FEATURE:
<223> OTHER INFORMATION: Humanized SF1 Heavy Chain Variable Region H1

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser
        115


<210> SEQ ID NO 16
<211> LENGTH: 117
<212> TYPE: PRT
<213> ORGANISM: Artificial Sequence
<220> FEATURE:
<223> OTHER INFORMATION: Humanized SF1 Heavy Chain Variable Region H2
```

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Ile Arg Gln Pro Pro Gly Lys Gly Leu Glu Trp Ile
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: Artificial Sequence
<220> FEATURE:
<223> OTHER INFORMATION: Humanized SF1 Heavy Chain Variable Region H3

<400> SEQUENCE: 17

Gln Val Gln Leu Val Glu Ser Gly Gly Gly Val Val Gln Pro Gly Gly
1               5                   10                  15

Ser Leu Arg Leu Ser Cys Ala Val Ser Gly Phe Ser Leu Thr Ser Tyr
            20                  25                  30

Ala Val His Trp Val Arg Gln Ala Pro Gly Lys Gly Leu Glu Trp Leu
        35                  40                  45

Gly Ile Ile Trp Gly Gly Gly Ser Thr Asn Tyr Asn Ser Ala Val Lys
    50                  55                  60

Gly Arg Phe Thr Ile Ser Lys Asp Asn Ser Lys Ser Ser Val Tyr Leu
65                  70                  75                  80

Gln Met Asn Ser Leu Arg Thr Glu Asp Thr Ala Leu Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Humanized SF1 Heavy Chain Variable Region L1

<400> SEQUENCE: 18

Glu Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

```
Glu Ile Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Asn Tyr Pro Leu Ala Thr
                85                  90                  95

Phe Gly Gly Gly Thr Lys Leu Glu Ile Lys
            100                 105


<210> SEQ ID NO 19
<211> LENGTH: 106
<212> TYPE: PRT
<213> ORGANISM: Artificial Sequence
<220> FEATURE:
<223> OTHER INFORMATION: Humanized SF1 Heavy Chain Variable Region L2

<400> SEQUENCE: 19

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Glu Ile Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Asn Tyr Pro Leu Ala Thr
                85                  90                  95

Phe Gly Gly Gly Thr Lys Leu Glu Ile Lys
            100                 105


<210> SEQ ID NO 20
<211> LENGTH: 106
<212> TYPE: PRT
<213> ORGANISM: Artificial Sequence
<220> FEATURE:
<223> OTHER INFORMATION: Humanized SF1 Heavy Chain Variable Region L3

<400> SEQUENCE: 20

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ser Pro Lys Pro Leu Ile Tyr
        35                  40                  45

Glu Ile Ser Lys Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Trp Asn Tyr Pro Leu Ala Thr
                85                  90                  95

Phe Gly Gly Gly Thr Lys Leu Glu Ile Lys
            100                 105


<210> SEQ ID NO 21
<211> LENGTH: 251
<212> TYPE: PRT
```

```
<213> ORGANISM: Artificial Sequence
<220> FEATURE:
<223> OTHER INFORMATION: Humanized SF1-scFv-H1L1

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Gln Leu Thr Gln Ser Pro Ser Ser Leu Ser
    130                 135                 140

Ala Ser Val Gly Asp Arg Val Thr Ile Thr Cys Arg Ala Ser Ser Ser
145                 150                 155                 160

Val Ser Tyr Met His Trp Tyr Gln Gln Lys Pro Gly Lys Ala Pro Lys
                165                 170                 175

Pro Leu Ile Tyr Glu Ile Ser Lys Leu Ala Ser Gly Val Pro Ser Arg
            180                 185                 190

Phe Ser Gly Ser Gly Ser Gly Thr Asp Tyr Thr Leu Thr Ile Ser Ser
        195                 200                 205

Leu Gln Pro Glu Asp Phe Ala Thr Tyr Tyr Cys Gln Gln Trp Asn Tyr
    210                 215                 220

Pro Leu Ala Thr Phe Gly Gly Gly Thr Lys Leu Glu Ile Lys Gly Leu
225                 230                 235                 240

Gln Gln Gly Gly Thr His His His His His His
                245                 250


<210> SEQ ID NO 22
<211> LENGTH: 251
<212> TYPE: PRT
<213> ORGANISM: Artificial Sequence
<220> FEATURE:
<223> OTHER INFORMATION: Humanized SF1-scFv-H1L2

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80
```

```
Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Gln Leu Thr Gln Ser Pro Ser Ser Leu Ser
    130                 135                 140

Ala Ser Val Gly Asp Arg Val Thr Ile Thr Cys Arg Ala Ser Ser Ser
145                 150                 155                 160

Val Ser Tyr Met His Trp Tyr Gln Gln Lys Pro Gly Lys Ala Pro Lys
                165                 170                 175

Pro Leu Ile Tyr Glu Ile Ser Lys Leu Ala Ser Gly Val Pro Ser Arg
            180                 185                 190

Phe Ser Gly Ser Gly Ser Gly Thr Asp Tyr Thr Leu Thr Ile Ser Ser
        195                 200                 205

Leu Gln Pro Glu Asp Phe Ala Thr Tyr Tyr Cys Gln Gln Trp Asn Tyr
    210                 215                 220

Pro Leu Ala Thr Phe Gly Gly Gly Thr Lys Leu Glu Ile Lys Gly Leu
225                 230                 235                 240

Gln Gln Gly Gly Thr His His His His His His
                245                 250


<210> SEQ ID NO 23
<211> LENGTH: 251
<212> TYPE: PRT
<213> ORGANISM: Artificial Sequence
<220> FEATURE:
<223> OTHER INFORMATION: Humanized SF1-scFv-H2L1

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Ile Arg Gln Pro Pro Gly Lys Gly Leu Glu Trp Ile
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Gln Leu Thr Gln Ser Pro Ser Ser Leu Ser
    130                 135                 140

Ala Ser Val Gly Asp Arg Val Thr Ile Thr Cys Arg Ala Ser Ser Ser
145                 150                 155                 160

Val Ser Tyr Met His Trp Tyr Gln Gln Lys Pro Gly Lys Ala Pro Lys
                165                 170                 175

Pro Leu Ile Tyr Glu Ile Ser Lys Leu Ala Ser Gly Val Pro Ser Arg
            180                 185                 190
```

```
Phe Ser Gly Ser Gly Ser Gly Thr Asp Tyr Thr Leu Thr Ile Ser Ser
        195                 200                 205

Leu Gln Pro Glu Asp Phe Ala Thr Tyr Tyr Cys Gln Gln Trp Asn Tyr
    210                 215                 220

Pro Leu Ala Thr Phe Gly Gly Gly Thr Lys Leu Glu Ile Lys Gly Leu
225                 230                 235                 240

Gln Gln Gly Gly Thr His His His His His His
                245                 250
```

<210> SEQ ID NO 24
<211> LENGTH: 251
<212> TYPE: PRT
<213> ORGANISM: Artificial Sequence
<220> FEATURE:
<223> OTHER INFORMATION: Humanized SF1-scFv-H3L3

<400> SEQUENCE: 24

```
Gln Val Gln Leu Val Glu Ser Gly Gly Gly Val Val Gln Pro Gly Gly
1               5                   10                  15

Ser Leu Arg Leu Ser Cys Ala Val Ser Gly Phe Ser Leu Thr Ser Tyr
            20                  25                  30

Ala Val His Trp Val Arg Gln Ala Pro Gly Lys Gly Leu Glu Trp Leu
        35                  40                  45

Gly Ile Ile Trp Gly Gly Gly Ser Thr Asn Tyr Asn Ser Ala Val Lys
    50                  55                  60

Gly Arg Phe Thr Ile Ser Lys Asp Asn Ser Lys Ser Ser Val Tyr Leu
65                  70                  75                  80

Gln Met Asn Ser Leu Arg Thr Glu Asp Thr Ala Leu Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Asp Phe Gln Ser
    130                 135                 140

Val Thr Pro Lys Glu Lys Val Thr Ile Thr Cys Arg Ala Ser Ser Ser
145                 150                 155                 160

Val Ser Tyr Met His Trp Tyr Gln Gln Lys Pro Asp Gln Ser Pro Lys
                165                 170                 175

Pro Leu Ile Tyr Glu Ile Ser Lys Leu Ala Ser Gly Val Pro Ser Arg
            180                 185                 190

Phe Ser Gly Ser Gly Ser Gly Thr Asp Tyr Thr Leu Thr Ile Asn Ser
        195                 200                 205

Leu Glu Ala Glu Asp Ala Ala Thr Tyr Tyr Cys Gln Gln Trp Asn Tyr
    210                 215                 220

Pro Leu Ala Thr Phe Gly Gly Gly Thr Lys Leu Glu Ile Lys Gly Leu
225                 230                 235                 240

Gln Gln Gly Gly Thr His His His His His His
                245                 250
```

<210> SEQ ID NO 25
<211> LENGTH: 447
<212> TYPE: PRT
<213> ORGANISM: Artificial Sequence
<220> FEATURE:
<223> OTHER INFORMATION: Full Length Humanized SF1 Heavy Chain

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 26
<211> LENGTH: 213
<212> TYPE: PRT
<213> ORGANISM: Artificial Sequence
<220> FEATURE:
<223> OTHER INFORMATION: Full Length Humanized SF1 Light Chain

<400> SEQUENCE: 26

Glu Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Glu Ile Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Asn Tyr Pro Leu Ala Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 27
<211> LENGTH: 447
<212> TYPE: PRT
<213> ORGANISM: Artificial Sequence
<220> FEATURE:
<223> OTHER INFORMATION: Full Length Humanized SF1 Heavy Chain IgG1-LALA

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30
```

-continued

```
Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 28
<211> LENGTH: 444
<212> TYPE: PRT
<213> ORGANISM: Artificial Sequence
<220> FEATURE:
<223> OTHER INFORMATION: Full Length Humanized SF1 Heavy Chain IgG4-SPLE

<400> SEQUENCE: 28

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Val His Trp Val Arg Gln Pro Pro Gly Lys Gly Leu Glu Trp Leu
        35                  40                  45

Gly Ile Ile Trp Gly Gly Gly Ser Thr Asn Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Glu Lys Leu Gly Arg Phe Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

-continued

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 29
<211> LENGTH: 15
<212> TYPE: PRT
<213> ORGANISM: Artificial Sequence
<220> FEATURE:
<223> OTHER INFORMATION: G4S Linker

<400> SEQUENCE: 29

Gly Gly Gly Gly Ser Gly Gly Gly Gly Ser Gly Gly Gly Gly Ser
1               5                   10                  15


<210> SEQ ID NO 30
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 30

Gly Leu Gln Gln Gly Gly Thr His His His His His His
1               5                   10


<210> SEQ ID NO 31
<211> LENGTH: 6
<212> TYPE: PRT
<213> ORGANISM: Artificial Sequence
<220> FEATURE:
<223> OTHER INFORMATION: The sequence is artificially synthesized

<400> SEQUENCE: 31

His His His His His His
1               5
```